US008029797B2

(12) United States Patent
Torres et al.

(10) Patent No.: US 8,029,797 B2
(45) Date of Patent: Oct. 4, 2011

(54) MULTIVALENT HIV IMMUNOGENIC COMPOSITIONS COMPRISING A POOL OF LIPIDATED AND NONLIPIDATED PEPTIDES REPRESENTING GAG AND ENV VARIABLE REGIONS

(75) Inventors: José Vidal Torres, Davis, CA (US); David Evander Anderson, Brookline, MA (US); Franscisco J. Diaz-Mitoma, Ottawa (CA)

(73) Assignee: Variation Biotechnologies Inc., Gatineau (CA)

( * ) Notice: Subject to any disclaimer, the term of this patent is extended or adjusted under 35 U.S.C. 154(b) by 282 days.

(21) Appl. No.: 11/817,640

(22) PCT Filed: Feb. 28, 2006

(86) PCT No.: PCT/CA2006/000295
§ 371 (c)(1),
(2), (4) Date: Sep. 2, 2008

(87) PCT Pub. No.: WO2006/092046
PCT Pub. Date: Sep. 8, 2006

(65) Prior Publication Data
US 2009/0117141 A1    May 7, 2009

Related U.S. Application Data

(60) Provisional application No. 60/656,908, filed on Mar. 1, 2005.

(51) Int. Cl.
*A61K 39/21*    (2006.01)
*A61K 39/385*    (2006.01)
(52) U.S. Cl. .............. 424/188.1; 424/208.1; 424/196.11
(58) Field of Classification Search .................. None
See application file for complete search history.

(56) References Cited

U.S. PATENT DOCUMENTS
2002/0183484 A1    12/2002    Torres

FOREIGN PATENT DOCUMENTS
WO    WO 01/24810 A1    4/2001

OTHER PUBLICATIONS

Walker, B. D., and D. R. Burton, 2008, Toward an AIDS vacine, Science 320:760-764.*
Haigwood, N. L., 2004, Predictive value of primate models for AIDS, AIDS Reviews 6:187-198.*
Gallo, R. C., 2005, The end or the beginning of the drive to an HIV-preventive vaccine: a view from over 20 years, The Lancet, 266:1894-1898.*
Desrosiers, R. C., 2004, Prospects for an AIDS vaccine, Nat. Med. 10(3):221-223.*
Carlos, M. P., et al., 2000, Immunogenicity of a vaccine preparation representing the variable reigons of the HIV type 1 envelope glycoprotein, AIDS Res. Human Retrovir. 16(2):153-161.*
Gahery-Segard, H., et al., 2000, Multiepitopic B- and T-cell responses induced in humans by a human immunodeficiency virus type 1 lipopeptide vaccine, J. Virol. 74(4):1694-1703.*
HIV Sequence Compendium, 2003, Leitner, T., et al., eds., Published by Theoretical Biology and Biophysics Group, Los Alamos National Laboratory, NM, LA-UR 04-7420 (http://www.hiv.lanl.gov./).*
Azizi et al., "Induction of broad cross-subtype-specific HIV-1 immune responses by a novel multivalent HIV-1 peptide vaccine in cynomolgus macaques", Journal of Immunology, vol. 180, No. 4, Feb. 2008, pp. 2174-2186.
European Search Report dated Dec. 29, 2008, from European Patent Application No. 06705249.8.
Carlos et al., "Immunogenicity of a vaccine preparation representing the variable regions of the HIV type 1 envelope glycoprotein", *AIDS Res & Human Retroviruses* 16 (2), pp. 153-161 (2000).
Gahery-Segard et al.,"Multiepitopic B- and T-cell responses induced in humans by a human immunodeficiency virus type 1 lipopeptide vaccine", *J. Virol.* 74 (4) pp. 1694-1703 (2000).
Marcus Altfeld et al., Enhanced Detection of Human Immunodeficiency Virus Type 1-Specific T-Cell Responses to Highly Variable Regions by Using Peptides Based on Autologous Virus Sequences, Journal of Virology, Jul. 2003, pp. 7330-7340, vol. 77, No. 13, American Society for Microbiology, Washington D.C., USA.

* cited by examiner

*Primary Examiner* — Jeffrey Parkin
(74) *Attorney, Agent, or Firm* — Choate Hall & Stewart LLP; Charles E. Lyon; Jessica Russell Colantonio

(57) ABSTRACT

An anti-HIV vaccine composition is disclosed. The vaccine comprises an combination of immunogenic peptide mixtures, which mixtures may be prepared in a single synthesis. The composition collectively represents the in vivo variability seen in immunogenic epitopes from highly variable regions of HIV. Immunization with the vaccine elicits broadly reactive immunity (CTL and T helper cell responses) against the divergent strains of HIV upon which it is based. The vaccine may be formulated to target regionally distinct variability based on an HIV clade predominant in a geographical region.

9 Claims, 32 Drawing Sheets

HIV-I-V1 peptide variants

| 1 | T | D | A | K | N | N | N | T | N | T | T | T | N | N | S | N | I | I | G | N | E | K | G | E | I | K | N | 2920.023 |
|---|---|---|---|---|---|---|---|---|---|---|---|---|---|---|---|---|---|---|---|---|---|---|---|---|---|---|---|----------|
| 2 | T | D | A | K | N | N | N | T | N | T | T | T | N | N | S | N | I | I | G | M | E | K | G | E | I | K | N | 2937.118 |
| 3 | T | D | A | K | N | T | N | T | N | T | T | T | N | N | S | N | I | I | G | N | E | K | G | E | I | K | N | 2907.024 |
| 4 | T | D | A | K | N | T | N | T | N | T | T | T | N | N | S | N | I | I | G | M | E | K | G | E | I | K | N | 2924.119 |
| 5 | T | D | A | N | N | N | N | T | N | T | T | T | N | N | S | N | I | I | G | N | E | K | G | E | I | K | N | 2905.954 |
| 6 | T | D | A | N | N | N | N | T | N | T | T | T | N | N | S | N | I | I | G | M | E | K | G | E | I | K | N | 2923.048 |
| 7 | T | D | A | N | N | T | N | T | N | T | T | T | N | N | S | N | I | I | G | N | E | K | G | E | I | K | N | 2892.955 |
| 8 | T | D | A | N | N | T | N | T | N | T | T | T | N | N | S | N | I | I | G | M | E | K | G | E | I | K | N | 2910.049 |
| 9 | T | N | A | K | N | N | N | T | N | T | T | T | N | N | S | N | I | I | G | N | E | K | G | E | I | K | N | 2919.039 |
| 10 | T | N | A | K | N | N | N | T | N | T | T | T | N | N | S | N | I | I | G | M | E | K | G | E | I | K | N | 2936.133 |
| 11 | T | N | A | K | N | T | N | T | N | T | T | T | N | N | S | N | I | I | G | N | E | K | G | E | I | K | N | 2906.04 |
| 12 | T | N | A | K | N | T | N | T | N | T | T | T | N | N | S | N | I | I | G | M | E | K | G | E | I | K | N | 2923.134 |
| 13 | T | N | A | N | N | N | N | T | N | T | T | T | N | N | S | N | I | I | G | N | E | K | G | E | I | K | N | 2904.969 |
| 14 | T | N | A | N | N | N | N | T | N | T | T | T | N | N | S | N | I | I | G | M | E | K | G | E | I | K | N | 2922.063 |
| 15 | T | N | A | N | N | T | N | T | N | T | T | T | N | N | S | N | I | I | G | N | E | K | G | E | I | K | N | 2891.97 |
| 16 | T | N | A | N | N | T | N | T | N | T | T | T | N | N | S | N | I | I | G | M | E | K | G | E | I | K | N | 2909.064 |
|   | * |   | * |   | * |   |   |   |   |   |   |   |   |   |   |   |   |   |   | * |   |   |   |   |   |   |   | MW |

Figure 2

| AA | T | A | K | S | I | G | M | E | D | N | Total |
|----|---|---|---|---|---|---|---|---|---|---|-------|
| Qnt. | 88 | 16 | 40 | 16 | 48 | 32 | 8 | 32 | 8 | 144 | 432 |
| % | 20 | 4 | 9 | 4 | 11 | 7 | 2 | 7 | 2 | 33 | 100 |

Figure 3

| Counter Ion | Molecular weight* | Counter Ion content, % | Lipid content, % | Protein content, % |
|-------------|-------------------|------------------------|------------------|---------------------|
| Free form | 46632.7 | n/a | n/a | 100 |
| Acetate | 49992.7 | 7 | n/a | 93 |

*MW of acetylated form is calculated according to the formula
$MW = MW_{free} + MW_{AcOH} \times (N_{var} + N_K + N_H + N_R)$, where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 4

HIV-I-V2 peptide variants

| | | | | | | | | | | | | | | | | | | | | |
|---|---|---|---|---|---|---|---|---|---|---|---|---|---|---|---|---|---|---|---|---|
| 1 | S | F | N | M | T | T | E | I | R | D | K | K | Q | K | V | H | A | L | F | Y | K | L | D | 2813.237 |
| 2 | S | F | N | M | T | T | E | I | R | D | K | K | Q | K | V | Y | A | L | F | Y | K | L | D | 2839.271 |
| 3 | S | F | N | M | T | T | E | I | R | D | K | K | Q | K | E | H | A | L | F | Y | K | L | D | 2843.22 |
| 4 | S | F | N | M | T | T | E | I | R | D | K | K | Q | K | E | Y | A | L | F | Y | K | L | D | 2869.253 |
| 5 | S | F | N | M | T | T | S | I | R | D | K | K | Q | K | V | H | A | L | F | Y | K | L | D | 2771.2 |
| 6 | S | F | N | M | T | T | S | I | R | D | K | K | Q | K | V | Y | A | L | F | Y | K | L | D | 2797.234 |
| 7 | S | F | N | M | T | T | S | I | R | D | K | K | Q | K | E | H | A | L | F | Y | K | L | D | 2801.183 |
| 8 | S | F | N | M | T | T | S | I | R | D | K | K | Q | K | E | Y | A | L | F | Y | K | L | D | 2827.217 |
| 9 | S | F | N | I | T | T | E | I | R | D | K | K | Q | K | V | H | A | L | F | Y | K | L | D | 2795.197 |
| 10 | S | F | N | I | T | T | E | I | R | D | K | K | Q | K | V | Y | A | L | F | Y | K | L | D | 2821.231 |
| 11 | S | F | N | I | T | T | E | I | R | D | K | K | Q | K | E | H | A | L | F | Y | K | L | D | 2825.18 |
| 12 | S | F | N | I | T | T | E | I | R | D | K | K | Q | K | E | Y | A | L | F | Y | K | L | D | 2851.214 |
| 13 | S | F | N | I | T | T | S | I | R | D | K | K | Q | K | V | H | A | L | F | Y | K | L | D | 2753.161 |
| 14 | S | F | N | I | T | T | S | I | R | D | K | K | Q | K | V | Y | A | L | F | Y | K | L | D | 2779.194 |
| 15 | S | F | N | I | T | T | S | I | R | D | K | K | Q | K | E | H | A | L | F | Y | K | L | D | 2783.143 |
| 16 | S | F | N | I | T | T | S | I | R | D | K | K | Q | K | E | Y | A | L | F | Y | K | L | D | 2809.177 |
| | | | * | | * | | | | | | | | | | * | * | | | | | | | | MW |

Figure 5

| AA | S | F | N | M | I | T | E | R | D | K | Q | V | H | Y | A | L | Total |
|---|---|---|---|---|---|---|---|---|---|---|---|---|---|---|---|---|---|
| Qnt. | 24 | 32 | 16 | 8 | 24 | 32 | 16 | 16 | 32 | 64 | 16 | 8 | 8 | 24 | 16 | 32 | 368 |
| % | 7 | 9 | 4 | 2 | 7 | 9 | 4 | 4 | 9 | 17 | 4 | 2 | 2 | 7 | 4 | 9 | 100 |

Figure 6

| Counter Ion | Molecular weight* | Counter Ion content, % | Lipid content, % | Protein content, % |
|---|---|---|---|---|
| Free form | 44979.31 | n/a | n/a | 100 |
| Acetate | 51219.31 | 12 | n/a | 88 |

*MW of acetylated form is calculated according to the formula
MW = MW$_{free}$ + MW$_{AcOH}$ x (N$_{var}$ ÷ N$_K$ + N$_H$ + N$_R$), where MW$_{free}$ is total MW of desalted peptides, MW$_{AcOH}$ is MW of acetate ion (60 m.u.), N$_{var}$, N$_K$, N$_H$ and N$_R$ are numbers of peptide variants, Lys, His and Arg residues correspondingly.

Figure 7

HIV-I-V3 peptide variants

| 1  | R | K | S | I | R | I | G | P | G | Q | A | F | Y | A | T | G | D | I | 1950.203 |
|----|---|---|---|---|---|---|---|---|---|---|---|---|---|---|---|---|---|---|----------|
| 2  | R | K | S | I | R | I | G | P | G | Q | A | F | Y | A | T | G | E | I | 1964.23  |
| 3  | R | K | S | I | R | I | G | P | G | Q | A | F | Y | T | T | G | D | I | 1980.229 |
| 4  | R | K | S | I | R | I | G | P | G | Q | A | F | Y | T | T | G | E | I | 1994.256 |
| 5  | R | K | S | I | R | I | G | P | G | R | A | F | Y | A | T | G | D | I | 1978.26  |
| 6  | R | K | S | I | R | I | G | P | G | R | A | F | Y | A | T | G | E | I | 1992.286 |
| 7  | R | K | S | I | R | I | G | P | G | R | A | F | Y | T | T | G | D | I | 2008.286 |
| 8  | R | K | S | I | R | I | G | P | G | R | A | F | Y | T | T | G | E | I | 2022.312 |
| 9  | R | K | S | I | H | I | G | P | G | Q | A | F | Y | A | T | G | D | I | 1931.157 |
| 10 | R | K | S | I | H | I | G | P | G | Q | A | F | Y | A | T | G | E | I | 1945.183 |
| 11 | R | K | S | I | H | I | G | P | G | Q | A | F | Y | T | T | G | D | I | 1961.183 |
| 12 | R | K | S | I | H | I | G | P | G | Q | A | F | Y | T | T | G | E | I | 1975.209 |
| 13 | R | K | S | I | H | I | G | P | G | R | A | F | Y | A | T | G | D | I | 1959.213 |
| 14 | R | K | S | I | H | I | G | P | G | R | A | F | Y | A | T | G | E | I | 1973.24  |
| 15 | R | K | S | I | H | I | G | P | G | R | A | F | Y | T | T | G | D | I | 1989.239 |
| 16 | R | K | S | I | H | I | G | P | G | R | A | F | Y | T | T | G | E | I | 2003.266 |
|    |   |   |   | * |   |   |   |   |   | * |   |   |   | * |   |   | * |   | MW       |

Figure 8

| AA   | R  | K  | S  | I  | H | G  | P  | Q  | A  | F  | Y  | T  | D | E | Total |
|------|----|----|----|----|---|----|----|----|----|----|----|----|---|---|-------|
| Qnt. | 32 | 16 | 16 | 48 | 8 | 48 | 16 | 8  | 24 | 16 | 16 | 24 | 8 | 8 | 288   |
| %    | 11 | 6  | 6  | 17 | 3 | 17 | 6  | 3  | 8  | 6  | 6  | 8  | 3 | 3 | 100   |

Figure 9

| Counter Ion | Molecular weight* | Counter Ion content, % | Lipid content, % | Protein content, % |
|-------------|-------------------|------------------------|------------------|--------------------|
| Free form   | 31627.75          | n/a                    | n/a              | 100                |
| Acetate     | 35947.75          | 12                     | n/a              | 88                 |

*MW of acetylated form is calculated according to the formula
MW = $MW_{free}$ + $MW_{AcOH}$ × ($N_{var}$ + $N_K$ + $N_H$ + $N_R$), where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 10

HIV-I-V4 peptide variants

| # | 1 | 2 | 3 | 4 | 5 | 6 | 7 | 8 | 9 | 10 | 11 | 12 | 13 | 14 | 15 | 16 | 17 | 18 | 19 | 20 | MW |
|---|---|---|---|---|---|---|---|---|---|----|----|----|----|----|----|----|----|----|----|----|-----|
| 1 | N | T | T | G | L | F | N | S | T | N | G | N | T | T | S | T | N | N | N | G | T | I | T | L | 2457.522 |
| 2 | N | T | T | G | L | F | N | S | T | N | G | N | T | T | S | N | N | N | G | T | I | T | L | 2470.52 |
| 3 | N | T | T | G | L | F | N | S | T | N | G | N | T | T | N | T | N | N | G | T | I | T | L | 2484.547 |
| 4 | N | T | T | G | L | F | N | S | T | N | G | N | T | T | N | N | N | N | G | T | I | T | L | 2497.546 |
| 5 | N | T | T | G | L | F | N | S | T | N | N | T | T | S | T | N | N | G | T | I | T | L | 2514.573 |
| 6 | N | T | T | G | L | F | N | S | T | N | N | T | T | S | N | N | N | G | T | I | T | L | 2527.572 |
| 7 | N | T | T | G | L | F | N | S | T | N | N | T | T | N | T | N | N | G | T | I | T | L | 2541.598 |
| 8 | N | T | T | G | L | F | N | S | T | N | N | T | T | N | N | N | N | G | T | I | T | L | 2554.597 |
| 9 | N | T | T | Q | L | F | N | S | T | N | G | N | T | T | S | T | N | N | G | T | I | T | L | 2528.6 |
| 10 | N | T | T | Q | L | F | N | S | T | N | G | N | T | T | S | N | N | N | G | T | I | T | L | 2541.598 |
| 11 | N | T | T | Q | L | F | N | S | T | N | G | N | T | T | N | T | N | N | G | T | I | T | L | 2555.625 |
| 12 | N | T | T | Q | L | F | N | S | T | N | G | N | T | T | N | N | N | N | G | T | I | T | L | 2568.624 |
| 13 | N | T | T | Q | L | F | N | S | T | N | N | T | T | S | T | N | N | G | T | I | T | L | 2585.651 |
| 14 | N | T | T | Q | L | F | N | S | T | N | N | T | T | S | N | N | N | G | T | I | T | L | 2598.65 |
| 15 | N | T | T | Q | L | F | N | S | T | N | N | T | T | N | T | N | N | G | T | I | T | L | 2612.676 |
| 16 | N | T | T | Q | L | F | N | S | T | N | N | T | T | N | N | N | N | G | T | I | T | L | 2625.675 |

Figure 11

| AA | N | T | G | L | Q | F | S | I | Total |
|----|---|---|---|---|---|---|---|---|-------|
| Qnt. | 136 | 120 | 32 | 32 | 8 | 16 | 24 | 16 | 384 |
| % | 35 | 31 | 8 | 8 | 2 | 4 | 6 | 4 | 100 |

Figure 12

| Counter Ion | Molecular weight* | Counter Ion content, % | Lipid content, % | Protein content, % |
|---|---|---|---|---|
| Free form | 40665.57 | n/a | n/a | 100 |
| Acetate | 41625.57 | 2 | n/a | 98 |

*MW of acetylated form is calculated according to the formula
MW = MW$_{free}$ + MW$_{AcOH}$ × (N$_{var}$ + N$_K$ + N$_H$ + N$_R$), where MW$_{free}$ is total MW of desalted peptides, MW$_{AcOH}$ is MW of acetate ion (60 m.u.), N$_{var}$, N$_K$, N$_H$ and N$_R$ are numbers of peptide variants, Lys, His and Arg residues correspondingly.

Figure 13

HIV-I-V5 peptide variants

| | | | | | | | | | | | | | | | |
|---|---|---|---|---|---|---|---|---|---|---|---|---|---|---|---|
| 1 | G | N | N | N | N | T | T | E | T | F | R | P | G | G | G | 1535.532 |
| 2 | G | N | N | N | N | T | N | E | T | F | R | P | G | G | G | 1548.531 |
| 3 | G | N | N | N | S | T | T | E | T | F | R | P | G | G | G | 1508.507 |
| 4 | G | N | N | N | S | T | N | E | T | F | R | P | G | G | G | 1521.506 |
| 5 | G | N | N | T | N | T | T | E | T | F | R | P | G | G | G | 1522.534 |
| 6 | G | N | N | T | N | T | N | E | T | F | R | P | G | G | G | 1535.532 |
| 7 | G | N | N | T | S | T | T | E | T | F | R | P | G | G | G | 1495.508 |
| 8 | G | N | N | T | S | T | N | E | T | F | R | P | G | G | G | 1508.507 |
| 9 | G | A | N | N | N | T | T | E | T | F | R | P | G | G | G | 1492.508 |
| 10 | G | A | N | N | N | T | N | E | T | F | R | P | G | G | G | 1505.506 |
| 11 | G | A | N | N | S | T | T | E | T | F | R | P | G | G | G | 1465.482 |
| 12 | G | A | N | N | S | T | N | E | T | F | R | P | G | G | G | 1478.481 |
| 13 | G | A | N | T | N | T | T | E | T | F | R | P | G | G | G | 1479.509 |
| 14 | G | A | N | T | N | T | N | E | T | F | R | P | G | G | G | 1492.508 |
| 15 | G | A | N | T | S | T | T | E | T | F | R | P | G | G | G | 1452.483 |
| 16 | G | A | N | T | S | T | N | E | T | F | R | P | G | G | G | 1465.482 |
| | * | | * | * | | * | | | | | | | | | | MW |

Figure 14

| AA | G | N | A | T | S | E | F | R | P | Total |
|---|---|---|---|---|---|---|---|---|---|---|
| Qnt. | 64 | 48 | 8 | 48 | 8 | 16 | 16 | 16 | 16 | 240 |
| % | 27 | 20 | 3 | 20 | 3 | 7 | 7 | 7 | 7 | 100 |

Figure 15

| Counter Ion | Molecular weight* | Counter Ion content, % | Lipid content, % | Protein content, % |
|---|---|---|---|---|
| Free form | 24008.12 | n/a | n/a | 100 |
| Acetate | 25928.12 | 7 | n/a | 93 |

*MW of acetylated form is calculated according to the formula
MW = MW$_{free}$ + MW$_{AcOH}$ x (N$_{var}$ + N$_K$ + N$_H$ + N$_R$), where MW$_{free}$ is total MW of desalted peptides, MW$_{AcOH}$ is MW of acetate ion (60 m.u.), N$_{var}$, N$_K$, N$_H$ and N$_R$ are numbers of peptide variants, Lys, His and Arg residues correspondingly.

Figure 16

HIV-I-V6 peptide variants

| | | | | | | | | | | | | | | | | | | | | | | | |
|---|---|---|---|---|---|---|---|---|---|---|---|---|---|---|---|---|---|---|---|---|---|---|---|
| 1 | | T | D | A | K | N | N | N | T | N | T | T | T | N | N | S | N | I | I | G | N | E | K | G | E | I | K | N | 3699.179 |
| 2 | | T | D | A | K | N | N | N | T | N | T | T | T | N | N | S | N | I | I | G | M | E | K | G | E | I | K | N | 3716.274 |
| 3 | | T | D | A | K | N | T | N | T | N | T | T | T | N | N | S | N | I | I | G | N | E | K | G | E | I | K | N | 3686.18 |
| 4 | | T | D | A | K | N | T | N | T | N | T | T | T | N | N | S | N | I | I | G | M | E | K | G | E | I | K | N | 3703.275 |
| 5 | | T | D | A | N | N | N | N | T | N | T | T | T | N | N | S | N | I | I | G | N | E | K | G | E | I | K | N | 3685.11 |
| 6 | diPalmitoyl-KSS- | T | D | A | N | N | N | N | T | N | T | T | T | N | N | S | N | I | I | G | M | E | K | G | E | I | K | N | 3702.204 |
| 7 | | T | D | A | N | N | T | N | T | N | T | T | T | N | N | S | N | I | I | G | N | E | K | G | E | I | K | N | 3672.111 |
| 8 | | T | D | A | N | N | T | N | T | N | T | T | T | N | N | S | N | I | I | G | M | E | K | G | E | I | K | N | 3689.205 |
| 9 | | T | N | A | K | N | N | N | T | N | T | T | T | N | N | S | N | I | I | G | N | E | K | G | E | I | K | N | 3698.195 |
| 10 | | T | N | A | K | N | N | N | T | N | T | T | T | N | N | S | N | I | I | G | M | E | K | G | E | I | K | N | 3715.289 |
| 11 | | T | N | A | K | N | T | N | T | N | T | T | T | N | N | S | N | I | I | G | N | E | K | G | E | I | K | N | 3685.196 |
| 12 | | T | N | A | K | N | T | N | T | N | T | T | T | N | N | S | N | I | I | G | M | E | K | G | E | I | K | N | 3702.29 |
| 13 | | T | N | A | N | N | N | N | T | N | T | T | T | N | N | S | N | I | I | G | N | E | K | G | E | I | K | N | 3684.125 |
| 14 | | T | N | A | N | N | N | N | T | N | T | T | T | N | N | S | N | I | I | G | M | E | K | G | E | I | K | N | 3701.219 |
| 15 | | T | N | A | N | N | T | N | T | N | T | T | T | N | N | S | N | I | I | G | N | E | K | G | E | I | K | N | 3671.126 |
| 16 | | T | N | A | N | N | T | N | T | N | T | T | T | N | N | S | N | I | I | G | M | E | K | G | E | I | K | N | 3688.22 |
| | | * | * | * | | | | | | | | | | | | | | | | | * | | | | | | | | MW |

Figure 17

| AA | T | A | K | S | I | G | M | E | D | N | Total |
|---|---|---|---|---|---|---|---|---|---|---|---|
| Qnt. | 88 | 16 | 56 | 48 | 48 | 32 | 8 | 32 | 8 | 144 | 480 |
| % | 18 | 3 | 12 | 10 | 10 | 7 | 2 | 7 | 2 | 30 | 100 |

Figure 18

| Counter Ion | Molecular weight* | Counter Ion content, % | Lipid content, % | Protein content, % |
|---|---|---|---|---|
| Free form | 59099.2 | n/a | 13 | 87 |
| Acetate | 61499.2 | 4 | 12 | 88 |

*MW of acetylated form is calculated according to the formula
MW = $MW_{free}$ + $MW_{AcOH}$ × ($N_{var}$ + $N_K$ + $N_H$ + $N_R$), where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 19

HIV-I-V7 peptide variants

| | | | | | | | | | | | | | | | | | | | | | |
|---|---|---|---|---|---|---|---|---|---|---|---|---|---|---|---|---|---|---|---|---|---|
| 1 | | S | F | N | M | T | T | E | I | R | D | K | K | Q | K | V | H | A | L | F | Y | K | L | D | 3592.393 |
| 2 | | S | F | N | M | T | T | E | I | R | D | K | K | Q | K | V | Y | A | L | F | Y | K | L | D | 3618.427 |
| 3 | | S | F | N | M | T | T | E | I | R | D | K | K | Q | K | E | H | A | L | F | Y | K | L | D | 3622.376 |
| 4 | | S | F | N | M | T | T | E | I | R | D | K | K | Q | K | E | Y | A | L | F | Y | K | L | D | 3648.409 |
| 5 | | S | F | N | M | T | T | S | I | R | D | K | K | Q | K | V | H | A | L | F | Y | K | L | D | 3550.356 |
| 6 | | S | F | N | M | T | T | S | I | R | D | K | K | Q | K | V | Y | A | L | F | Y | K | L | D | 3576.39 |
| 7 | diPalmitoyl-KSS- | S | F | N | M | T | T | S | I | R | D | K | K | Q | K | E | H | A | L | F | Y | K | L | D | 3580.339 |
| 8 | | S | F | N | M | T | T | S | I | R | D | K | K | Q | K | E | Y | A | L | F | Y | K | L | D | 3606.373 |
| 9 | | S | F | N | I | T | T | E | I | R | D | K | K | Q | K | V | H | A | L | F | Y | K | L | D | 3574.353 |
| 10 | | S | F | N | I | T | T | E | I | R | D | K | K | Q | K | V | Y | A | L | F | Y | K | L | D | 3600.387 |
| 11 | | S | F | N | I | T | T | E | I | R | D | K | K | Q | K | E | H | A | L | F | Y | K | L | D | 3604.336 |
| 12 | | S | F | N | I | T | T | E | I | R | D | K | K | Q | K | E | Y | A | L | F | Y | K | L | D | 3630.37 |
| 13 | | S | F | N | I | T | T | S | I | R | D | K | K | Q | K | V | H | A | L | F | Y | K | L | D | 3532.317 |
| 14 | | S | F | N | I | T | T | S | I | R | D | K | K | Q | K | V | Y | A | L | F | Y | K | L | D | 3558.35 |
| 15 | | S | F | N | I | T | T | S | I | R | D | K | K | Q | K | E | H | A | L | F | Y | K | L | D | 3562.299 |
| 16 | | S | F | N | I | T | T | S | I | R | D | K | K | Q | K | E | Y | A | L | F | Y | K | L | D | 3588.333 |
| | | | | | * | | * | | | | | | | | * | * | | | | | | | | | MW |

Figure 20

| AA | S | F | N | M | I | T | E | R | D | K | Q | V | H | Y | A | L | Total |
|---|---|---|---|---|---|---|---|---|---|---|---|---|---|---|---|---|---|
| Qnt. | 56 | 32 | 16 | 8 | 24 | 32 | 16 | 16 | 32 | 80 | 16 | 8 | 8 | 24 | 16 | 32 | 416 |
| % | 13 | 8 | 4 | 2 | 6 | 8 | 4 | 4 | 8 | 19 | 4 | 2 | 2 | 6 | 4 | 8 | 100 |

Figure 21

| Counter Ion | Molecular weight* | Counter Ion content, % | Lipid content, % | Protein content, % |
|---|---|---|---|---|
| Free form | 57445.81 | n/a | 13 | 87 |
| Acetate | 62725.81 | 8 | 12 | 88 |

*MW of acetylated form is calculated according to the formula
$MW = MW_{free} + MW_{AcOH} \times (N_{var} + N_K + N_H + N_R)$, where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 22

HIV-I-V8 peptide variants

| # | | | | | | | | | | | | | | | | | MW |
|---|---|---|---|---|---|---|---|---|---|---|---|---|---|---|---|---|---|
| 1 |  | R | K | S | I | R | I | G | P | G | Q | A | F | Y | A | T | G | D | I | 2729.36 |
| 2 |  | R | K | S | I | R | I | G | P | G | Q | A | F | Y | A | T | G | E | I | 2743.387 |
| 3 |  | R | K | S | I | R | I | G | P | G | Q | A | F | Y | T | T | G | D | I | 2759.386 |
| 4 |  | R | K | S | I | R | I | G | P | G | Q | A | F | Y | T | T | G | E | I | 2773.413 |
| 5 |  | R | K | S | I | R | I | G | P | G | R | A | F | Y | A | T | G | D | I | 2757.417 |
| 6 |  | R | K | S | I | R | I | G | P | G | R | A | F | Y | A | T | G | E | I | 2771.443 |
| 7 | diPalmitoyl-KSS- | R | K | S | I | R | I | G | P | G | R | A | F | Y | T | T | G | D | I | 2787.443 |
| 8 |  | R | K | S | I | R | I | G | P | G | R | A | F | Y | T | T | G | E | I | 2801.469 |
| 9 |  | R | K | S | I | H | I | G | P | G | Q | A | F | Y | A | T | G | D | I | 2710.314 |
| 10 |  | R | K | S | I | H | I | G | P | G | Q | A | F | Y | A | T | G | E | I | 2724.34 |
| 11 |  | R | K | S | I | H | I | G | P | G | Q | A | F | Y | T | T | G | D | I | 2740.34 |
| 12 |  | R | K | S | I | H | I | G | P | G | Q | A | F | Y | T | T | G | E | I | 2754.366 |
| 13 |  | R | K | S | I | H | I | G | P | G | R | A | F | Y | A | T | G | D | I | 2738.37 |
| 14 |  | R | K | S | I | H | I | G | P | G | R | A | F | Y | A | T | G | E | I | 2752.397 |
| 15 |  | R | K | S | I | H | I | G | P | G | R | A | F | Y | T | T | G | D | I | 2768.396 |
| 16 |  | R | K | S | I | H | I | G | P | G | R | A | F | Y | T | T | G | E | I | 2782.423 |

Figure 23

| AA | R | K | S | I | H | G | P | Q | A | F | Y | T | D | E | Total |
|---|---|---|---|---|---|---|---|---|---|---|---|---|---|---|---|
| Qnt. | 32 | 32 | 48 | 48 | 8 | 48 | 16 | 8 | 24 | 16 | 16 | 24 | 8 | 8 | 336 |
| % | 10 | 10 | 14 | 14 | 2 | 14 | 5 | 2 | 7 | 5 | 5 | 7 | 2 | 2 | 100 |

Figure 24

| Counter Ion | Molecular weight* | Counter Ion content, % | Lipid content, % | Protein content, % |
|---|---|---|---|---|
| Free form | 44094.25 | n/a | 17 | 83 |
| Acetate | 47454.25 | 7 | 16 | 84 |

*MW of acetylated form is calculated according to the formula
MW = $MW_{free}$ + $MW_{AcOH}$ × ($N_{var}$ + $N_K$ + $N_H$ + $N_R$), where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 25

HIV-I-V9 peptide variants

| # | | | | | | | | | | | | | | | | | | | | | MW |
|---|---|---|---|---|---|---|---|---|---|---|---|---|---|---|---|---|---|---|---|---|---|
| 1 | | N | T | T | G | L | F | N | S | T | N | G | N | T | T | S | T | N | N | N | G | T | I | T | L | 3236.678 |
| 2 | | N | T | T | G | L | F | N | S | T | N | G | N | T | T | S | N | N | N | N | G | T | I | T | L | 3249.676 |
| 3 | | N | T | T | G | L | F | N | S | T | N | G | N | T | T | N | T | N | N | N | G | T | I | T | L | 3263.703 |
| 4 | | N | T | T | G | L | F | N | S | T | N | G | N | T | T | N | N | N | N | N | G | T | I | T | L | 3276.702 |
| 5 | | N | T | T | G | L | F | N | S | T | N | N | N | T | T | S | T | N | N | N | G | T | I | T | L | 3293.729 |
| 6 | diPalmitoyl-KSS- | N | T | T | G | L | F | N | S | T | N | N | N | T | T | S | N | N | N | N | G | T | I | T | L | 3306.728 |
| 7 | | N | T | T | G | L | F | N | S | T | N | N | N | T | T | N | T | N | N | N | G | T | I | T | L | 3320.754 |
| 8 | | N | T | T | G | L | F | N | S | T | N | N | N | T | T | N | N | N | N | N | G | T | I | T | L | 3333.753 |
| 9 | | N | T | T | Q | L | F | N | S | T | N | G | N | T | T | S | T | N | N | N | G | T | I | T | L | 3307.756 |
| 10 | | N | T | T | Q | L | F | N | S | T | N | G | N | T | T | S | N | N | N | N | G | T | I | T | L | 3320.754 |
| 11 | | N | T | T | Q | L | F | N | S | T | N | G | N | T | T | N | T | N | N | N | G | T | I | T | L | 3334.781 |
| 12 | | N | T | T | Q | L | F | N | S | T | N | G | N | T | T | N | N | N | N | N | G | T | I | T | L | 3347.78 |
| 13 | | N | T | T | Q | L | F | N | S | T | N | N | N | T | T | S | T | N | N | N | G | T | I | T | L | 3364.807 |
| 14 | | N | T | T | Q | L | F | N | S | T | N | N | N | T | T | S | N | N | N | N | G | T | I | T | L | 3377.806 |
| 15 | | N | T | T | Q | L | F | N | S | T | N | N | N | T | T | N | T | N | N | N | G | T | I | T | L | 3391.832 |
| 16 | | N | T | T | Q | L | F | N | S | T | N | N | N | T | T | N | N | N | N | N | G | T | I | T | L | 3404.831 |
| | | | | | * | | | | | | | | * | | | * | * | | | | | | | | | MW |

Figure 26

| AA | N | T | G | L | Q | F | S | I | K | Total |
|---|---|---|---|---|---|---|---|---|---|---|
| Qnt. | 136 | 120 | 32 | 32 | 8 | 16 | 56 | 16 | 16 | 432 |
| % | 31 | 28 | 7 | 7 | 2 | 4 | 13 | 4 | 4 | 100 |

Figure 27

| Counter Ion | Molecular weight* | Counter Ion content, % | Lipid content, % | Protein content, % |
|---|---|---|---|---|
| Free form | 53132.07 | n/a | 14 | 86 |
| Acetate | 53132.07 | 0 | 14 | 86 |

*MW of acetylated form is calculated according to the formula
MW = $MW_{free}$ + $MW_{AcOH}$ x ($N_{var}$ + $N_K$ + $N_H$ + $N_R$), where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 28

HIV-I-V10 peptide variants

| # | prefix | 1 | 2 | 3 | 4 | 5 | 6 | 7 | 8 | 9 | 10 | 11 | 12 | 13 | 14 | 15 | MW |
|---|---|---|---|---|---|---|---|---|---|---|---|---|---|---|---|---|---|
| 1 | diPalmitoyl-KSS- | G | N | N | N | N | T | T | E | T | F | R | P | G | G | G | 2314.689 |
| 2 | diPalmitoyl-KSS- | G | N | N | N | N | T | N | E | T | F | R | P | G | G | G | 2327.688 |
| 3 | diPalmitoyl-KSS- | G | N | N | N | S | T | T | E | T | F | R | P | G | G | G | 2287.664 |
| 4 | diPalmitoyl-KSS- | G | N | N | N | S | T | N | E | T | F | R | P | G | G | G | 2300.663 |
| 5 | diPalmitoyl-KSS- | G | N | N | T | N | T | T | E | T | F | R | P | G | G | G | 2301.691 |
| 6 | diPalmitoyl-KSS- | G | N | N | T | N | T | N | E | T | F | R | P | G | G | G | 2314.689 |
| 7 | diPalmitoyl-KSS- | G | N | N | T | S | T | T | E | T | F | R | P | G | G | G | 2274.665 |
| 8 | diPalmitoyl-KSS- | G | N | N | T | S | T | N | E | T | F | R | P | G | G | G | 2287.664 |
| 9 | diPalmitoyl-KSS- | G | A | N | N | N | T | T | E | T | F | R | P | G | G | G | 2271.665 |
| 10 | diPalmitoyl-KSS- | G | A | N | N | N | T | N | E | T | F | R | P | G | G | G | 2284.663 |
| 11 | diPalmitoyl-KSS- | G | A | N | N | S | T | T | E | T | F | R | P | G | G | G | 2244.639 |
| 12 | diPalmitoyl-KSS- | G | A | N | N | S | T | N | E | T | F | R | P | G | G | G | 2257.638 |
| 13 | diPalmitoyl-KSS- | G | A | N | T | N | T | T | E | T | F | R | P | G | G | G | 2258.666 |
| 14 | diPalmitoyl-KSS- | G | A | N | T | N | T | N | E | T | F | R | P | G | G | G | 2271.665 |
| 15 | diPalmitoyl-KSS- | G | A | N | T | S | T | T | E | T | F | R | P | G | G | G | 2231.64 |
| 16 | diPalmitoyl-KSS- | G | A | N | T | S | T | N | E | T | F | R | P | G | G | G | 2244.639 |
|   |   | * |   | * | * | * |   | * |   |   |   |   |   |   |   |   | MW |

Figure 29

| AA | G | N | A | T | S | E | F | R | P | K | Total |
|---|---|---|---|---|---|---|---|---|---|---|---|
| Qnt. | 64 | 48 | 8 | 48 | 40 | 16 | 16 | 16 | 16 | 16 | 288 |
| % | 22 | 17 | 3 | 17 | 14 | 6 | 6 | 6 | 6 | 6 | 100 |

Figure 30

| Counter Ion | Molecular weight* | Counter Ion content, % | Lipid content, % | Protein content, % |
|---|---|---|---|---|
| Free form | 36474.62 | n/a | 21 | 79 |
| Acetate | 37434.62 | 3 | 20 | 80 |

*MW of acetylated form is calculated according to the formula
$MW = MW_{free} + MW_{AcOH} \times (N_{var} + N_K + N_H + N_R)$, where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 31

HIV-I-V11 peptide variants

| 1 | | V | L | A | E | A | M | S | Q | V | T | N | S | N | T | M | M | 2506.15 |
|---|---|---|---|---|---|---|---|---|---|---|---|---|---|---|---|---|---|---|
| 2 | | V | L | A | E | A | M | S | Q | V | T | N | S | N | T | I | M | 2488.11 |
| 3 | diPalmitoyl-KSS- | V | L | A | E | A | M | S | Q | V | T | N | S | N | I | M | M | 2518.204 |
| 4 | | V | L | A | E | A | M | S | Q | V | T | N | S | N | I | I | M | 2500.164 |
| 5 | | V | L | A | E | A | M | S | Q | V | T | N | S | A | T | M | M | 2463.125 |
| 6 | | V | L | A | E | A | M | S | Q | V | T | N | S | A | T | I | M | 2445.086 |
| 7 | | V | L | A | E | A | M | S | Q | V | T | N | S | A | I | M | M | 2475.179 |
| 8 | | V | L | A | E | A | M | S | Q | V | T | N | S | A | I | I | M | 2457.139 |
| | | | | | | | | | | | | | | * | * | * | | MW |

Figure 32

| AA | V | L | A | E | M | S | Q | T | N | I | K | Total |
|---|---|---|---|---|---|---|---|---|---|---|---|---|
| Qnt. | 16 | 8 | 20 | 8 | 20 | 32 | 8 | 12 | 12 | 8 | 8 | 152 |
| % | 11 | 5 | 13 | 5 | 13 | 21 | 5 | 8 | 8 | 5 | 5 | 100 |

Figure 33

| Counter Ion | Molecular weight* | Counter Ion content, % | Lipid content, % | Protein content, % |
|---|---|---|---|---|
| Free form | 19853.16 | n/a | 19 | 81 |
| Acetate | 19853.16 | 0 | 19 | 81 |

*MW of acetylated form is calculated according to the formula
MW = MW$_{free}$ + MW$_{AcOH}$ x (N$_{var}$ + N$_K$ + N$_H$ + N$_R$), where MW$_{free}$ is total MW of desalted peptides, MW$_{AcOH}$ is MW of acetate ion (60 m.u.), N$_{var}$, N$_K$, N$_H$ and N$_R$ are numbers of peptide variants, Lys, His and Arg residues correspondingly.

Figure 34

HIV-I-V12 peptide variants

| | | | | | | | | | | | | | | | | | | | | |
|---|---|---|---|---|---|---|---|---|---|---|---|---|---|---|---|---|---|---|---|---|
| 1 | | E | S | F | R | F | G | E | E | T | T | T | P | P | Q | K | R | E | Q | Y | P | L | A | S | L | 3609.223 |
| 2 | diPalmitoyl-KSS- | E | S | F | R | F | G | E | E | T | T | T | P | P | Q | K | R | E | Q | Y | P | L | T | S | L | 3639.249 |
| 3 | | E | S | F | R | F | G | E | E | T | T | T | P | P | Q | K | R | E | L | Y | P | L | A | S | L | 3594.252 |
| 4 | | E | S | F | R | F | G | E | E | T | T | T | P | P | Q | K | R | E | L | Y | P | L | T | S | L | 3624.278 |
| 5 | | E | S | F | R | F | G | E | E | T | T | T | P | P | Q | K | K | E | Q | Y | P | L | A | S | L | 3581.21 |
| 6 | | E | S | F | R | F | G | E | E | T | T | T | P | P | Q | K | K | E | Q | Y | P | L | T | S | L | 3611.236 |
| 7 | | E | S | F | R | F | G | E | E | T | T | T | P | P | Q | K | K | E | L | Y | P | L | A | S | L | 3566.238 |
| 8 | | E | S | F | R | F | G | E | E | T | T | T | P | P | Q | K | K | E | L | Y | P | L | T | S | L | 3596.264 |
| | | | | | | | | | | | | | | | | * | | * | | * | | | | | MW |

Figure 35

| AA | E | S | F | R | G | T | P | Q | K | Y | L | A | Total |
|---|---|---|---|---|---|---|---|---|---|---|---|---|---|
| Qnt. | 32 | 32 | 16 | 12 | 8 | 28 | 24 | 12 | 20 | 8 | 20 | 4 | 216 |
| % | 15 | 15 | 7 | 6 | 4 | 13 | 11 | 6 | 9 | 4 | 9 | 2 | 100 |

Figure 36

| Counter Ion | Molecular weight* | Counter Ion content, % | Lipid content, % | Protein content, % |
|---|---|---|---|---|
| Free form | 28677.83 | n/a | 13 | 87 |
| Acetate | 30117.83 | 5 | 13 | 87 |

*MW of acetylated form is calculated according to the formula
MW = $MW_{free}$ + $MW_{AcOH}$ × ($N_{var}$ + $N_K$ + $N_H$ + $N_R$), where $MW_{free}$ is total MW of desalted peptides, $MW_{AcOH}$ is MW of acetate ion (60 m.u.), $N_{var}$, $N_K$, $N_H$ and $N_R$ are numbers of peptide variants, Lys, His and Arg residues correspondingly.

Figure 37

SEQUENCE LISTING

<160> NUMBER OF SEQ ID NOS: 176

<210> SEQ ID NO 1
<211> LENGTH: 27
<212> TYPE: PRT
<213> ORGANISM: HIV

<400> SEQUENCE: 1

Thr Asp Ala Lys Asn Asn Asn Thr Asn Thr Thr Thr Asn Asn Ser Asn
1               5                   10                  15

Ile Ile Gly Asn Glu Lys Gly Glu Ile Lys Asn
            20                  25

<210> SEQ ID NO 2
<211> LENGTH: 27
<212> TYPE: PRT
<213> ORGANISM: HIV

<400> SEQUENCE: 2

Thr Asp Ala Lys Asn Asn Asn Thr Asn Thr Thr Thr Asn Asn Ser Asn
1               5                   10                  15

Ile Ile Gly Met Glu Lys Gly Glu Ile Lys Asn
            20                  25

```
<210> SEQ ID NO 3
<211> LENGTH: 27
<212> TYPE: PRT
<213> ORGANISM: HIV

<400> SEQUENCE: 3

Thr Asp Ala Lys Asn Thr Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 4
<211> LENGTH: 27
<212> TYPE: PRT
<213> ORGANISM: HIV

<400> SEQUENCE: 4

Thr Asp Ala Lys Asn Thr Asn Thr Asn Thr Thr Asn Asn Ser Asn
1               5                   10                  15

Ile Ile Gly Met Glu Lys Gly Glu Ile Lys Asn
            20                  25

<210> SEQ ID NO 5
<211> LENGTH: 27
<212> TYPE: PRT
<213> ORGANISM: HIV

<400> SEQUENCE: 5

Thr Asp Ala Asn Asn Asn Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 6
<211> LENGTH: 27
<212> TYPE: PRT
<213> ORGANISM: HIV

<400> SEQUENCE: 6

Thr Asp Ala Asn Asn Asn Asn Thr Asn Thr Thr Asn Asn Ser Asn
1               5                   10                  15

Ile Ile Gly Met Glu Lys Gly Glu Ile Lys Asn
            20                  25

<210> SEQ ID NO 7
<211> LENGTH: 27
<212> TYPE: PRT
<213> ORGANISM: HIV

<400> SEQUENCE: 7

Thr Asp Ala Asn Asn Thr Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 8
<211> LENGTH: 27
<212> TYPE: PRT
<213> ORGANISM: HIV

<400> SEQUENCE: 8

Thr Asp Ala Asn Asn Thr Asn Thr Asn Thr Thr Asn Asn Ser Asn
```

```
                 1               5                  10                 15
Ile Ile Gly Met Glu Lys Gly Glu Ile Lys Asn
            20                  25

<210> SEQ ID NO 9
<211> LENGTH: 27
<212> TYPE: PRT
<213> ORGANISM: HIV

<400> SEQUENCE: 9

Thr Asn Ala Lys Asn Asn Asn Thr Asn Thr Thr Thr Asn Asn Ser Asn
1               5                  10                 15

Ile Ile Gly Asn Glu Lys Gly Glu Ile Lys Asn
            20                  25

<210> SEQ ID NO 10
<211> LENGTH: 27
<212> TYPE: PRT
<213> ORGANISM: HIV

<400> SEQUENCE: 10

Thr Asn Ala Lys Asn Asn Asn Thr Asn Thr Thr Thr Asn Asn Ser Asn
1               5                  10                 15

Ile Ile Gly Met Glu Lys Gly Glu Ile Lys Asn
            20                  25

<210> SEQ ID NO 11
<211> LENGTH: 27
<212> TYPE: PRT
<213> ORGANISM: HIV

<400> SEQUENCE: 11

Thr Asn Ala Lys Asn Thr Asn Thr Asn Thr Thr Asn Asn Ser Asn
1               5                  10                 15

Ile Ile Gly Asn Glu Lys Gly Glu Ile Lys Asn
            20                  25

<210> SEQ ID NO 12
<211> LENGTH: 27
<212> TYPE: PRT
<213> ORGANISM: HIV

<400> SEQUENCE: 12

Thr Asn Ala Lys Asn Thr Asn Thr Asn Thr Thr Asn Asn Ser Asn
1               5                  10                 15

Ile Ile Gly Met Glu Lys Gly Glu Ile Lys Asn
            20                  25

<210> SEQ ID NO 13
<211> LENGTH: 27
<212> TYPE: PRT
<213> ORGANISM: HIV

<400> SEQUENCE: 13

Thr Asn Ala Asn Asn Asn Asn Thr Asn Thr Thr Thr Asn Asn Ser Asn
1               5                  10                 15

Ile Ile Gly Asn Glu Lys Gly Glu Ile Lys Asn
            20                  25

<210> SEQ ID NO 14
<211> LENGTH: 27
<212> TYPE: PRT
<213> ORGANISM: HIV
```

```
<400> SEQUENCE: 14

Thr Asn Ala Asn Asn Asn Thr Asn Thr Thr Asn Asn Ser Asn
1               5                   10                  15

Ile Ile Gly Met Glu Lys Gly Glu Ile Lys Asn
            20                  25

<210> SEQ ID NO 15
<211> LENGTH: 27
<212> TYPE: PRT
<213> ORGANISM: HIV

<400> SEQUENCE: 15

Thr Asn Ala Asn Asn Thr Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 16
<211> LENGTH: 27
<212> TYPE: PRT
<213> ORGANISM: HIV

<400> SEQUENCE: 16

Thr Asn Ala Asn Asn Thr Asn Thr Asn Thr Thr Asn Asn Ser Asn
1               5                   10                  15

Ile Ile Gly Met Glu Lys Gly Glu Ile Lys Asn
            20                  25

<210> SEQ ID NO 17
<211> LENGTH: 23
<212> TYPE: PRT
<213> ORGANISM: HIV

<400> SEQUENCE: 17

Ser Phe Asn Met Thr Thr Glu Ile Arg Asp Lys Lys Gln Lys Val His
1               5                   10                  15

Ala Leu Phe Tyr Lys Leu Asp
            20

<210> SEQ ID NO 18
<211> LENGTH: 23
<212> TYPE: PRT
<213> ORGANISM: HIV

<400> SEQUENCE: 18

Ser Phe Asn Met Thr Thr Glu Ile Arg Asp Lys Lys Gln Lys Glu Tyr
1               5                   10                  15

Ala Leu Phe Tyr Lys Leu Asp
            20

<210> SEQ ID NO 19
<211> LENGTH: 23
<212> TYPE: PRT
<213> ORGANISM: HIV

<400> SEQUENCE: 19

Ser Phe Asn Ile Thr Thr Glu Ile Arg Asp Lys Lys Gln Lys Glu Tyr
1               5                   10                  15

Ala Leu Phe Tyr Lys Leu Asp
            20
```

```
<210> SEQ ID NO 20
<211> LENGTH: 23
<212> TYPE: PRT
<213> ORGANISM: HIV

<400> SEQUENCE: 20

Ser Phe Asn Met Thr Thr Glu Ile Arg Asp Lys Lys Gln Lys Glu His
1               5                   10                  15

Ala Leu Phe Tyr Lys Leu Asp
            20

<210> SEQ ID NO 21
<211> LENGTH: 23
<212> TYPE: PRT
<213> ORGANISM: HIV

<400> SEQUENCE: 21

Ser Phe Asn Met Thr Thr Glu Ile Arg Asp Lys Lys Gln Lys Val Tyr
1               5                   10                  15

Ala Leu Phe Tyr Lys Leu Asp
            20

<210> SEQ ID NO 22
<211> LENGTH: 23
<212> TYPE: PRT
<213> ORGANISM: HIV

<400> SEQUENCE: 22

Ser Phe Asn Met Thr Thr Ser Ile Arg Asp Lys Lys Gln Lys Glu Tyr
1               5                   10                  15

Ala Leu Phe Tyr Lys Leu Asp
            20

<210> SEQ ID NO 23
<211> LENGTH: 23
<212> TYPE: PRT
<213> ORGANISM: HIV

<400> SEQUENCE: 23

Ser Phe Asn Ile Thr Thr Glu Ile Arg Asp Lys Lys Gln Lys Glu His
1               5                   10                  15

Ala Leu Phe Tyr Lys Leu Asp
            20

<210> SEQ ID NO 24
<211> LENGTH: 23
<212> TYPE: PRT
<213> ORGANISM: HIV

<400> SEQUENCE: 24

Ser Phe Asn Ile Thr Thr Glu Ile Arg Asp Lys Lys Gln Lys Val Tyr
1               5                   10                  15

Ala Leu Phe Tyr Lys Leu Asp
            20

<210> SEQ ID NO 25
<211> LENGTH: 23
<212> TYPE: PRT
<213> ORGANISM: HIV

<400> SEQUENCE: 25

Ser Phe Asn Ile Thr Thr Ser Ile Arg Asp Lys Lys Gln Lys Glu Tyr
1               5                   10                  15
```

Ala Leu Phe Tyr Lys Leu Asp
            20

<210> SEQ ID NO 26
<211> LENGTH: 23
<212> TYPE: PRT
<213> ORGANISM: HIV

<400> SEQUENCE: 26

Ser Phe Asn Met Thr Thr Ser Ile Arg Asp Lys Lys Gln Lys Glu His
1               5                   10                  15

Ala Leu Phe Tyr Lys Leu Asp
            20

<210> SEQ ID NO 27
<211> LENGTH: 23
<212> TYPE: PRT
<213> ORGANISM: HIV

<400> SEQUENCE: 27

Ser Phe Asn Met Thr Thr Ser Ile Arg Asp Lys Lys Gln Lys Val Tyr
1               5                   10                  15

Ala Leu Phe Tyr Lys Leu Asp
            20

<210> SEQ ID NO 28
<211> LENGTH: 23
<212> TYPE: PRT
<213> ORGANISM: HIV

<400> SEQUENCE: 28

Ser Phe Asn Ile Thr Thr Glu Ile Arg Asp Lys Lys Gln Lys Val His
1               5                   10                  15

Ala Leu Phe Tyr Lys Leu Asp
            20

<210> SEQ ID NO 29
<211> LENGTH: 23
<212> TYPE: PRT
<213> ORGANISM: HIV

<400> SEQUENCE: 29

Ser Phe Asn Ile Thr Thr Ser Ile Arg Asp Lys Lys Gln Lys Glu His
1               5                   10                  15

Ala Leu Phe Tyr Lys Leu Asp
            20

<210> SEQ ID NO 30
<211> LENGTH: 23
<212> TYPE: PRT
<213> ORGANISM: HIV

<400> SEQUENCE: 30

Ser Phe Asn Ile Thr Thr Ser Ile Arg Asp Lys Lys Gln Lys Val Tyr
1               5                   10                  15

Ala Leu Phe Tyr Lys Leu Asp
            20

<210> SEQ ID NO 31
<211> LENGTH: 23
<212> TYPE: PRT
<213> ORGANISM: HIV

<400> SEQUENCE: 31

```
Ser Phe Asn Met Thr Thr Ser Ile Arg Asp Lys Lys Gln Lys Val His
1               5                   10                  15

Ala Leu Phe Tyr Lys Leu Asp
            20
```

<210> SEQ ID NO 32
<211> LENGTH: 23
<212> TYPE: PRT
<213> ORGANISM: HIV

<400> SEQUENCE: 32

```
Ser Phe Asn Ile Thr Thr Ser Ile Arg Asp Lys Lys Gln Lys Val His
1               5                   10                  15

Ala Leu Phe Tyr Lys Leu Asp
            20
```

<210> SEQ ID NO 33
<211> LENGTH: 18
<212> TYPE: PRT
<213> ORGANISM: HIV

<400> SEQUENCE: 33

```
Arg Lys Ser Ile Arg Ile Gly Pro Gly Gln Ala Phe Tyr Ala Thr Gly
1               5                   10                  15

Asp Ile
```

<210> SEQ ID NO 34
<211> LENGTH: 18
<212> TYPE: PRT
<213> ORGANISM: HIV

<400> SEQUENCE: 34

```
Arg Lys Ser Ile His Ile Gly Pro Gly Gln Ala Phe Tyr Ala Thr Gly
1               5                   10                  15

Asp Ile
```

<210> SEQ ID NO 35
<211> LENGTH: 18
<212> TYPE: PRT
<213> ORGANISM: HIV

<400> SEQUENCE: 35

```
Arg Lys Ser Ile Arg Ile Gly Pro Gly Arg Ala Phe Tyr Ala Thr Gly
1               5                   10                  15

Asp Ile
```

<210> SEQ ID NO 36
<211> LENGTH: 18
<212> TYPE: PRT
<213> ORGANISM: HIV

<400> SEQUENCE: 36

```
Arg Lys Ser Ile His Ile Gly Pro Gly Arg Ala Phe Tyr Ala Thr Gly
1               5                   10                  15

Asp Ile
```

<210> SEQ ID NO 37
<211> LENGTH: 18
<212> TYPE: PRT
<213> ORGANISM: HIV

<400> SEQUENCE: 37

-continued

Arg Lys Ser Ile Arg Ile Gly Pro Gly Gln Ala Phe Tyr Thr Thr Gly
1               5                   10                  15

Asp Ile

<210> SEQ ID NO 38
<211> LENGTH: 18
<212> TYPE: PRT
<213> ORGANISM: HIV

<400> SEQUENCE: 38

Arg Lys Ser Ile His Ile Gly Pro Gly Gln Ala Phe Tyr Thr Thr Gly
1               5                   10                  15

Asp Ile

<210> SEQ ID NO 39
<211> LENGTH: 18
<212> TYPE: PRT
<213> ORGANISM: HIV

<400> SEQUENCE: 39

Arg Lys Ser Ile Arg Ile Gly Pro Gly Arg Ala Phe Tyr Thr Thr Gly
1               5                   10                  15

Asp Ile

<210> SEQ ID NO 40
<211> LENGTH: 18
<212> TYPE: PRT
<213> ORGANISM: HIV

<400> SEQUENCE: 40

Arg Lys Ser Ile His Ile Gly Pro Gly Arg Ala Phe Tyr Thr Thr Gly
1               5                   10                  15

Asp Ile

<210> SEQ ID NO 41
<211> LENGTH: 18
<212> TYPE: PRT
<213> ORGANISM: HIV

<400> SEQUENCE: 41

Arg Lys Ser Ile Arg Ile Gly Pro Gly Gln Ala Phe Tyr Ala Thr Gly
1               5                   10                  15

Glu Ile

<210> SEQ ID NO 42
<211> LENGTH: 18
<212> TYPE: PRT
<213> ORGANISM: HIV

<400> SEQUENCE: 42

Arg Lys Ser Ile His Ile Gly Pro Gly Gln Ala Phe Tyr Ala Thr Gly
1               5                   10                  15

Glu Ile

<210> SEQ ID NO 43
<211> LENGTH: 18
<212> TYPE: PRT
<213> ORGANISM: HIV

<400> SEQUENCE: 43

Arg Lys Ser Ile Arg Ile Gly Pro Gly Arg Ala Phe Tyr Ala Thr Gly

```
1               5                   10                  15

Glu Ile

<210> SEQ ID NO 44
<211> LENGTH: 18
<212> TYPE: PRT
<213> ORGANISM: HIV

<400> SEQUENCE: 44

Arg Lys Ser Ile His Ile Gly Pro Gly Arg Ala Phe Tyr Ala Thr Gly
1               5                   10                  15

Glu Ile

<210> SEQ ID NO 45
<211> LENGTH: 18
<212> TYPE: PRT
<213> ORGANISM: HIV

<400> SEQUENCE: 45

Arg Lys Ser Ile Arg Ile Gly Pro Gly Gln Ala Phe Tyr Thr Thr Gly
1               5                   10                  15

Glu Ile

<210> SEQ ID NO 46
<211> LENGTH: 18
<212> TYPE: PRT
<213> ORGANISM: HIV

<400> SEQUENCE: 46

Arg Lys Ser Ile His Ile Gly Pro Gly Gln Ala Phe Tyr Thr Thr Gly
1               5                   10                  15

Glu Ile

<210> SEQ ID NO 47
<211> LENGTH: 18
<212> TYPE: PRT
<213> ORGANISM: HIV

<400> SEQUENCE: 47

Arg Lys Ser Ile Arg Ile Gly Pro Gly Arg Ala Phe Tyr Thr Thr Gly
1               5                   10                  15

Glu Ile

<210> SEQ ID NO 48
<211> LENGTH: 18
<212> TYPE: PRT
<213> ORGANISM: HIV

<400> SEQUENCE: 48

Arg Lys Ser Ile His Ile Gly Pro Gly Arg Ala Phe Tyr Thr Thr Gly
1               5                   10                  15

Glu Ile

<210> SEQ ID NO 49
<211> LENGTH: 24
<212> TYPE: PRT
<213> ORGANISM: HIV

<400> SEQUENCE: 49

Asn Thr Thr Gly Leu Phe Asn Ser Thr Asn Gly Asn Thr Thr Ser Thr
1               5                   10                  15
```

Asn Asn Asn Gly Thr Ile Thr Leu
            20

<210> SEQ ID NO 50
<211> LENGTH: 24
<212> TYPE: PRT
<213> ORGANISM: HIV

<400> SEQUENCE: 50

Asn Thr Thr Gly Leu Phe Asn Ser Thr Asn Gly Asn Thr Ser Asn
1               5                   10                  15

Asn Asn Asn Gly Thr Ile Thr Leu
            20

<210> SEQ ID NO 51
<211> LENGTH: 24
<212> TYPE: PRT
<213> ORGANISM: HIV

<400> SEQUENCE: 51

Asn Thr Thr Gly Leu Phe Asn Ser Thr Asn Gly Asn Thr Thr Asn Thr
1               5                   10                  15

Asn Asn Asn Gly Thr Ile Thr Leu
            20

<210> SEQ ID NO 52
<211> LENGTH: 24
<212> TYPE: PRT
<213> ORGANISM: HIV

<400> SEQUENCE: 52

Asn Thr Thr Gly Leu Phe Asn Ser Thr Asn Gly Asn Thr Thr Asn Asn
1               5                   10                  15

Asn Asn Asn Gly Thr Ile Thr Leu
            20

<210> SEQ ID NO 53
<211> LENGTH: 24
<212> TYPE: PRT
<213> ORGANISM: HIV

<400> SEQUENCE: 53

Asn Thr Thr Gly Leu Phe Asn Ser Thr Asn Asn Asn Thr Ser Thr
1               5                   10                  15

Asn Asn Asn Gly Thr Ile Thr Leu
            20

<210> SEQ ID NO 54
<211> LENGTH: 24
<212> TYPE: PRT
<213> ORGANISM: HIV

<400> SEQUENCE: 54

Asn Thr Thr Gly Leu Phe Asn Ser Thr Asn Asn Asn Thr Ser Asn
1               5                   10                  15

Asn Asn Asn Gly Thr Ile Thr Leu
            20

<210> SEQ ID NO 55
<211> LENGTH: 24
<212> TYPE: PRT
<213> ORGANISM: HIV

<400> SEQUENCE: 55

Asn Thr Thr Gly Leu Phe Asn Ser Thr Asn Asn Thr Thr Asn Thr
1               5                   10                  15

Asn Asn Asn Gly Thr Ile Thr Leu
            20

<210> SEQ ID NO 56
<211> LENGTH: 24
<212> TYPE: PRT
<213> ORGANISM: HIV

<400> SEQUENCE: 56

Asn Thr Thr Gly Leu Phe Asn Ser Thr Asn Asn Thr Thr Asn Asn
1               5                   10                  15

Asn Asn Asn Gly Thr Ile Thr Leu
            20

<210> SEQ ID NO 57
<211> LENGTH: 24
<212> TYPE: PRT
<213> ORGANISM: HIV

<400> SEQUENCE: 57

Asn Thr Thr Gln Leu Phe Asn Ser Thr Asn Gly Asn Thr Thr Ser Thr
1               5                   10                  15

Asn Asn Asn Gly Thr Ile Thr Leu
            20

<210> SEQ ID NO 58
<211> LENGTH: 24
<212> TYPE: PRT
<213> ORGANISM: HIV

<400> SEQUENCE: 58

Asn Thr Thr Gln Leu Phe Asn Ser Thr Asn Gly Asn Thr Thr Ser Asn
1               5                   10                  15

Asn Asn Asn Gly Thr Ile Thr Leu
            20

<210> SEQ ID NO 59
<211> LENGTH: 24
<212> TYPE: PRT
<213> ORGANISM: HIV

<400> SEQUENCE: 59

Asn Thr Thr Gln Leu Phe Asn Ser Thr Asn Gly Asn Thr Thr Asn Thr
1               5                   10                  15

Asn Asn Asn Gly Thr Ile Thr Leu
            20

<210> SEQ ID NO 60
<211> LENGTH: 24
<212> TYPE: PRT
<213> ORGANISM: HIV

<400> SEQUENCE: 60

Asn Thr Thr Gln Leu Phe Asn Ser Thr Asn Gly Asn Thr Thr Asn Asn
1               5                   10                  15

Asn Asn Asn Gly Thr Ile Thr Leu
            20

<210> SEQ ID NO 61
<211> LENGTH: 24

```
<212> TYPE: PRT
<213> ORGANISM: HIV

<400> SEQUENCE: 61

Asn Thr Thr Gln Leu Phe Asn Ser Thr Asn Asn Thr Thr Ser Thr
1               5                   10                  15

Asn Asn Asn Gly Thr Ile Thr Leu
            20

<210> SEQ ID NO 62
<211> LENGTH: 24
<212> TYPE: PRT
<213> ORGANISM: HIV

<400> SEQUENCE: 62

Asn Thr Thr Gln Leu Phe Asn Ser Thr Asn Asn Thr Thr Ser Asn
1               5                   10                  15

Asn Asn Asn Gly Thr Ile Thr Leu
            20

<210> SEQ ID NO 63
<211> LENGTH: 24
<212> TYPE: PRT
<213> ORGANISM: HIV

<400> SEQUENCE: 63

Asn Thr Thr Gln Leu Phe Asn Ser Thr Asn Asn Thr Thr Asn Thr
1               5                   10                  15

Asn Asn Asn Gly Thr Ile Thr Leu
            20

<210> SEQ ID NO 64
<211> LENGTH: 24
<212> TYPE: PRT
<213> ORGANISM: HIV

<400> SEQUENCE: 64

Asn Thr Thr Gln Leu Phe Asn Ser Thr Asn Asn Thr Thr Asn Asn
1               5                   10                  15

Asn Asn Asn Gly Thr Ile Thr Leu
            20

<210> SEQ ID NO 65
<211> LENGTH: 15
<212> TYPE: PRT
<213> ORGANISM: HIV

<400> SEQUENCE: 65

Gly Asn Asn Asn Asn Thr Thr Glu Thr Phe Arg Pro Gly Gly Gly
1               5                   10                  15

<210> SEQ ID NO 66
<211> LENGTH: 15
<212> TYPE: PRT
<213> ORGANISM: HIV

<400> SEQUENCE: 66

Gly Asn Asn Asn Asn Thr Asn Glu Thr Phe Arg Pro Gly Gly Gly
1               5                   10                  15

<210> SEQ ID NO 67
<211> LENGTH: 15
<212> TYPE: PRT
<213> ORGANISM: HIV
```

<400> SEQUENCE: 67

Gly Asn Asn Asn Ser Thr Thr Glu Thr Phe Arg Pro Gly Gly Gly
1               5                   10                  15

<210> SEQ ID NO 68
<211> LENGTH: 15
<212> TYPE: PRT
<213> ORGANISM: HIV

<400> SEQUENCE: 68

Gly Asn Asn Asn Ser Thr Asn Glu Thr Phe Arg Pro Gly Gly Gly
1               5                   10                  15

<210> SEQ ID NO 69
<211> LENGTH: 15
<212> TYPE: PRT
<213> ORGANISM: HIV

<400> SEQUENCE: 69

Gly Asn Asn Thr Asn Thr Thr Glu Thr Phe Arg Pro Gly Gly Gly
1               5                   10                  15

<210> SEQ ID NO 70
<211> LENGTH: 15
<212> TYPE: PRT
<213> ORGANISM: HIV

<400> SEQUENCE: 70

Gly Asn Asn Thr Asn Thr Asn Glu Thr Phe Arg Pro Gly Gly Gly
1               5                   10                  15

<210> SEQ ID NO 71
<211> LENGTH: 15
<212> TYPE: PRT
<213> ORGANISM: HIV

<400> SEQUENCE: 71

Gly Asn Asn Thr Ser Thr Thr Glu Thr Phe Arg Pro Gly Gly Gly
1               5                   10                  15

<210> SEQ ID NO 72
<211> LENGTH: 15
<212> TYPE: PRT
<213> ORGANISM: HIV

<400> SEQUENCE: 72

Gly Asn Asn Thr Ser Thr Asn Glu Thr Phe Arg Pro Gly Gly Gly
1               5                   10                  15

<210> SEQ ID NO 73
<211> LENGTH: 15
<212> TYPE: PRT
<213> ORGANISM: HIV

<400> SEQUENCE: 73

Gly Ala Asn Asn Asn Thr Thr Glu Thr Phe Arg Pro Gly Gly Gly
1               5                   10                  15

<210> SEQ ID NO 74
<211> LENGTH: 15
<212> TYPE: PRT
<213> ORGANISM: HIV

<400> SEQUENCE: 74

-continued

Gly Ala Asn Asn Thr Asn Glu Thr Phe Arg Pro Gly Gly Gly
1               5                   10                  15

<210> SEQ ID NO 75
<211> LENGTH: 15
<212> TYPE: PRT
<213> ORGANISM: HIV

<400> SEQUENCE: 75

Gly Ala Asn Asn Ser Thr Thr Glu Thr Phe Arg Pro Gly Gly Gly
1               5                   10                  15

<210> SEQ ID NO 76
<211> LENGTH: 15
<212> TYPE: PRT
<213> ORGANISM: HIV

<400> SEQUENCE: 76

Gly Ala Asn Asn Ser Thr Asn Glu Thr Phe Arg Pro Gly Gly Gly
1               5                   10                  15

<210> SEQ ID NO 77
<211> LENGTH: 15
<212> TYPE: PRT
<213> ORGANISM: HIV

<400> SEQUENCE: 77

Gly Ala Asn Thr Asn Thr Thr Glu Thr Phe Arg Pro Gly Gly Gly
1               5                   10                  15

<210> SEQ ID NO 78
<211> LENGTH: 15
<212> TYPE: PRT
<213> ORGANISM: HIV

<400> SEQUENCE: 78

Gly Ala Asn Thr Asn Thr Asn Glu Thr Phe Arg Pro Gly Gly Gly
1               5                   10                  15

<210> SEQ ID NO 79
<211> LENGTH: 15
<212> TYPE: PRT
<213> ORGANISM: HIV

<400> SEQUENCE: 79

Gly Ala Asn Thr Ser Thr Thr Glu Thr Phe Arg Pro Gly Gly Gly
1               5                   10                  15

<210> SEQ ID NO 80
<211> LENGTH: 15
<212> TYPE: PRT
<213> ORGANISM: HIV

<400> SEQUENCE: 80

Gly Ala Asn Thr Ser Thr Asn Glu Thr Phe Arg Pro Gly Gly Gly
1               5                   10                  15

<210> SEQ ID NO 81
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser- -continued

<400> SEQUENCE: 81

Thr Asp Ala Lys Asn Asn Asn Thr Asn Thr Thr Thr Asn Asn Ser Asn
1               5                   10                  15

Ile Ile Gly Asn Glu Lys Gly Glu Ile Lys Asn
            20                  25

<210> SEQ ID NO 82
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 82

Thr Asp Ala Lys Asn Asn Asn Thr Asn Thr Thr Thr Asn Asn Ser Asn
1               5                   10                  15

Ile Ile Gly Met Glu Lys Gly Glu Ile Lys Asn
            20                  25

<210> SEQ ID NO 83
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 83

Thr Asp Ala Lys Asn Thr Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 84
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 84

Thr Asp Ala Lys Asn Thr Asn Thr Asn Thr Thr Asn Asn Ser Asn
1               5                   10                  15

Ile Ile Gly Met Glu Lys Gly Glu Ile Lys Asn
            20                  25

<210> SEQ ID NO 85
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 85

Thr Asp Ala Asn Asn Asn Asn Thr Asn Thr Thr Thr Asn Asn Ser Asn
1               5                   10                  15

```
Ile Ile Gly Asn Glu Lys Gly Glu Ile Lys Asn
            20                  25
```

<210> SEQ ID NO 86
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 86

```
Thr Asp Ala Asn Asn Asn Asn Thr Asn Thr Thr Thr Asn Asn Ser Asn
1               5                   10                  15

Ile Ile Gly Met Glu Lys Gly Glu Ile Lys Asn
            20                  25
```

<210> SEQ ID NO 87
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 87

```
Thr Asp Ala Asn Asn Thr Asn Thr Asn Thr Thr Thr Asn Asn Ser Asn
1               5                   10                  15

Ile Ile Gly Asn Glu Lys Gly Glu Ile Lys Asn
            20                  25
```

<210> SEQ ID NO 88
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 88

```
Thr Asp Ala Asn Asn Thr Asn Thr Asn Thr Thr Asn Asn Ser Asn
1               5                   10                  15

Ile Ile Gly Met Glu Lys Gly Glu Ile Lys Asn
            20                  25
```

<210> SEQ ID NO 89
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 89

```
Thr Asn Ala Lys Asn Asn Asn Thr Asn Thr Thr Thr Asn Asn Ser Asn
1               5                   10                  15

Ile Ile Gly Asn Glu Lys Gly Glu Ile Lys Asn
            20                  25
```

```
<210> SEQ ID NO 90
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 90

Thr Asn Ala Lys Asn Asn Asn Thr Asn Thr Thr Thr Asn Asn Ser Asn
1               5                   10                  15

Ile Ile Gly Met Glu Lys Gly Glu Ile Lys Asn
            20                  25

<210> SEQ ID NO 91
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 91

Thr Asn Ala Lys Asn Thr Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 92
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 92

Thr Asn Ala Lys Asn Thr Asn Thr Asn Thr Thr Asn Asn Ser Asn
1               5                   10                  15

Ile Ile Gly Met Glu Lys Gly Glu Ile Lys Asn
            20                  25

<210> SEQ ID NO 93
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 93

Thr Asn Ala Asn Asn Asn Asn Thr Asn Thr Thr Asn Asn Ser Asn
1               5                   10                  15

Ile Ile Gly Asn Glu Lys Gly Glu Ile Lys Asn
            20                  25

<210> SEQ ID NO 94
<211> LENGTH: 27
<212> TYPE: PRT
```

```
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 94

Thr Asn Ala Asn Asn Asn Asn Thr Asn Thr Thr Thr Asn Asn Ser Asn
1               5                   10                  15

Ile Ile Gly Met Glu Lys Gly Glu Ile Lys Asn
            20                  25

<210> SEQ ID NO 95
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 95

Thr Asn Ala Asn Asn Thr Asn Thr Asn Thr Thr Thr Asn Asn Ser Asn
1               5                   10                  15

Ile Ile Gly Asn Glu Lys Gly Glu Ile Lys Asn
            20                  25

<210> SEQ ID NO 96
<211> LENGTH: 27
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 96

Thr Asn Ala Asn Asn Thr Asn Thr Asn Thr Thr Thr Asn Asn Ser Asn
1               5                   10                  15

Ile Ile Gly Met Glu Lys Gly Glu Ile Lys Asn
            20                  25

<210> SEQ ID NO 97
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 97

Ser Phe Asn Met Thr Thr Glu Ile Arg Asp Lys Lys Gln Lys Val His
1               5                   10                  15

Ala Leu Phe Tyr Lys Leu Asp
            20

<210> SEQ ID NO 98
<211> LENGTH: 23
<212> TYPE: PRT
<213> ORGANISM: HIV
<220> FEATURE:
<221> NAME/KEY: misc_feature
<222> LOCATION: 1
```

```
<223> OTHER INFORMATION: residue lipidated, for example with palmitoyl-
      Lys-Ser-Ser-

<400> SEQUENCE: 98

Ser Phe Asn Met Thr Thr Glu Ile Arg Asp Lys Lys Gln Lys Val Tyr
1               5                   10                  15

Ala Leu Phe Tyr Lys Leu Asp
            20

<210> SEQ ID NO 99
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 99

Ser Phe Asn Met Thr Thr Glu Ile Arg Asp Lys Lys Gln Lys Glu His
1               5                   10                  15

Ala Leu Phe Tyr Lys Leu Asp
            20

<210> SEQ ID NO 100
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 100

Ser Phe Asn Met Thr Thr Glu Ile Arg Asp Lys Lys Gln Lys Glu Tyr
1               5                   10                  15

Ala Leu Phe Tyr Lys Leu Asp
            20

<210> SEQ ID NO 101
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 101

Ser Phe Asn Met Thr Thr Ser Ile Arg Asp Lys Lys Gln Lys Val His
1               5                   10                  15

Ala Leu Phe Tyr Lys Leu Asp
            20

<210> SEQ ID NO 102
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 102
```

```
Ser Phe Asn Met Thr Thr Ser Ile Arg Asp Lys Lys Gln Lys Val Tyr
1               5                   10                  15

Ala Leu Phe Tyr Lys Leu Asp
            20

<210> SEQ ID NO 103
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 103

Ser Phe Asn Met Thr Thr Ser Ile Arg Asp Lys Lys Gln Lys Glu His
1               5                   10                  15

Ala Leu Phe Tyr Lys Leu Asp
            20

<210> SEQ ID NO 104
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 104

Ser Phe Asn Met Thr Thr Ser Ile Arg Asp Lys Lys Gln Lys Glu Tyr
1               5                   10                  15

Ala Leu Phe Tyr Lys Leu Asp
            20

<210> SEQ ID NO 105
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 105

Ser Phe Asn Ile Thr Thr Glu Ile Arg Asp Lys Lys Gln Lys Val His
1               5                   10                  15

Ala Leu Phe Tyr Lys Leu Asp
            20

<210> SEQ ID NO 106
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 106

Ser Phe Asn Ile Thr Thr Glu Ile Arg Asp Lys Lys Gln Lys Val Tyr
1               5                   10                  15
```

Ala Leu Phe Tyr Lys Leu Asp
            20

<210> SEQ ID NO 107
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 107

Ser Phe Asn Ile Thr Thr Glu Ile Arg Asp Lys Lys Gln Lys Glu His
1               5                   10                  15

Ala Leu Phe Tyr Lys Leu Asp
            20

<210> SEQ ID NO 108
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 108

Ser Phe Asn Ile Thr Thr Glu Ile Arg Asp Lys Lys Gln Lys Glu Tyr
1               5                   10                  15

Ala Leu Phe Tyr Lys Leu Asp
            20

<210> SEQ ID NO 109
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 109

Ser Phe Asn Ile Thr Thr Ser Ile Arg Asp Lys Lys Gln Lys Val His
1               5                   10                  15

Ala Leu Phe Tyr Lys Leu Asp
            20

<210> SEQ ID NO 110
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 110

Ser Phe Asn Ile Thr Thr Ser Ile Arg Asp Lys Lys Gln Lys Val Tyr
1               5                   10                  15

Ala Leu Phe Tyr Lys Leu Asp
            20

```
<210> SEQ ID NO 111
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 111

Ser Phe Asn Ile Thr Thr Ser Ile Arg Asp Lys Lys Gln Lys Glu His
1               5                   10                  15

Ala Leu Phe Tyr Lys Leu Asp
            20

<210> SEQ ID NO 112
<211> LENGTH: 23
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 112

Ser Phe Asn Ile Thr Thr Ser Ile Arg Asp Lys Lys Gln Lys Glu Tyr
1               5                   10                  15

Ala Leu Phe Tyr Lys Leu Asp
            20

<210> SEQ ID NO 113
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 113

Arg Lys Ser Ile Arg Ile Gly Pro Gly Gln Ala Phe Tyr Ala Thr Gly
1               5                   10                  15

Asp Ile

<210> SEQ ID NO 114
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 114

Arg Lys Ser Ile His Ile Gly Pro Gly Gln Ala Phe Tyr Ala Thr Gly
1               5                   10                  15

Asp Ile

<210> SEQ ID NO 115
<211> LENGTH: 18
<212> TYPE: PRT
<213> ORGANISM: HIV
<220> FEATURE:
<221> NAME/KEY: misc_feature
```

```
<222> LOCATION: 1
<223> OTHER INFORMATION: residue lipidated, for example with palmitoyl-
      Lys-Ser-Ser-

<400> SEQUENCE: 115

Arg Lys Ser Ile Arg Ile Gly Pro Gly Arg Ala Phe Tyr Ala Thr Gly
1               5                   10                  15

Asp Ile

<210> SEQ ID NO 116
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 116

Arg Lys Ser Ile His Ile Gly Pro Gly Arg Ala Phe Tyr Ala Thr Gly
1               5                   10                  15

Asp Ile

<210> SEQ ID NO 117
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 117

Arg Lys Ser Ile Arg Ile Gly Pro Gly Gln Ala Phe Tyr Thr Thr Gly
1               5                   10                  15

Asp Ile

<210> SEQ ID NO 118
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 118

Arg Lys Ser Ile His Ile Gly Pro Gly Gln Ala Phe Tyr Thr Thr Gly
1               5                   10                  15

Asp Ile

<210> SEQ ID NO 119
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 119

Arg Lys Ser Ile Arg Ile Gly Pro Gly Arg Ala Phe Tyr Thr Thr Gly
1               5                   10                  15
```

Asp Ile

<210> SEQ ID NO 120
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 120

Arg Lys Ser Ile His Ile Gly Pro Gly Arg Ala Phe Tyr Thr Thr Gly
1               5                   10                  15

Asp Ile

<210> SEQ ID NO 121
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 121

Arg Lys Ser Ile Arg Ile Gly Pro Gly Gln Ala Phe Tyr Ala Thr Gly
1               5                   10                  15

Glu Ile

<210> SEQ ID NO 122
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 122

Arg Lys Ser Ile His Ile Gly Pro Gly Gln Ala Phe Tyr Ala Thr Gly
1               5                   10                  15

Glu Ile

<210> SEQ ID NO 123
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 123

Arg Lys Ser Ile Arg Ile Gly Pro Gly Arg Ala Phe Tyr Ala Thr Gly
1               5                   10                  15

Glu Ile

<210> SEQ ID NO 124
<211> LENGTH: 18
<212> TYPE: PRT
<213> ORGANISM: HIV

```
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 124

Arg Lys Ser Ile His Ile Gly Pro Gly Arg Ala Phe Tyr Ala Thr Gly
1               5                   10                  15

Glu Ile

<210> SEQ ID NO 125
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 125

Arg Lys Ser Ile Arg Ile Gly Pro Gly Gln Ala Phe Tyr Thr Thr Gly
1               5                   10                  15

Glu Ile

<210> SEQ ID NO 126
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 126

Arg Lys Ser Ile His Ile Gly Pro Gly Gln Ala Phe Tyr Thr Thr Gly
1               5                   10                  15

Glu Ile

<210> SEQ ID NO 127
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 127

Arg Lys Ser Ile Arg Ile Gly Pro Gly Arg Ala Phe Tyr Thr Thr Gly
1               5                   10                  15

Glu Ile

<210> SEQ ID NO 128
<211> LENGTH: 18
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 128
```

Arg Lys Ser Ile His Ile Gly Pro Gly Arg Ala Phe Tyr Thr Thr Gly
1               5                   10                  15

Glu Ile

<210> SEQ ID NO 129
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 129

Asn Thr Thr Gly Leu Phe Asn Ser Thr Asn Gly Asn Thr Thr Ser Thr
1               5                   10                  15

Asn Asn Asn Gly Thr Ile Thr Leu
            20

<210> SEQ ID NO 130
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 130

Asn Thr Thr Gly Leu Phe Asn Ser Thr Asn Gly Asn Thr Thr Ser Asn
1               5                   10                  15

Asn Asn Asn Gly Thr Ile Thr Leu
            20

<210> SEQ ID NO 131
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 131

Asn Thr Thr Gly Leu Phe Asn Ser Thr Asn Gly Asn Thr Thr Asn Thr
1               5                   10                  15

Asn Asn Asn Gly Thr Ile Thr Leu
            20

<210> SEQ ID NO 132
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 132

Asn Thr Thr Gly Leu Phe Asn Ser Thr Asn Gly Asn Thr Thr Asn Asn
1               5                   10                  15

Asn Asn Asn Gly Thr Ile Thr Leu
            20

<210> SEQ ID NO 133
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 133

Asn Thr Thr Gly Leu Phe Asn Ser Thr Asn Asn Asn Thr Thr Ser Thr
1               5                   10                  15

Asn Asn Asn Gly Thr Ile Thr Leu
            20

<210> SEQ ID NO 134
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 134

Asn Thr Thr Gly Leu Phe Asn Ser Thr Asn Asn Asn Thr Thr Ser Asn
1               5                   10                  15

Asn Asn Asn Gly Thr Ile Thr Leu
            20

<210> SEQ ID NO 135
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 135

Asn Thr Thr Gly Leu Phe Asn Ser Thr Asn Asn Asn Thr Asn Thr
1               5                   10                  15

Asn Asn Asn Gly Thr Ile Thr Leu
            20

<210> SEQ ID NO 136
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 136

Asn Thr Thr Gly Leu Phe Asn Ser Thr Asn Asn Asn Thr Thr Asn Asn
1               5                   10                  15

Asn Asn Asn Gly Thr Ile Thr Leu
            20

<210> SEQ ID NO 137
<211> LENGTH: 24

```
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 137

Asn Thr Thr Gln Leu Phe Asn Ser Thr Asn Gly Asn Thr Thr Ser Thr
1               5                   10                  15

Asn Asn Asn Gly Thr Ile Thr Leu
            20

<210> SEQ ID NO 138
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 138

Asn Thr Thr Gln Leu Phe Asn Ser Thr Asn Gly Asn Thr Thr Ser Asn
1               5                   10                  15

Asn Asn Asn Gly Thr Ile Thr Leu
            20

<210> SEQ ID NO 139
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 139

Asn Thr Thr Gln Leu Phe Asn Ser Thr Asn Gly Asn Thr Thr Asn Thr
1               5                   10                  15

Asn Asn Asn Gly Thr Ile Thr Leu
            20

<210> SEQ ID NO 140
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 140

Asn Thr Thr Gln Leu Phe Asn Ser Thr Asn Gly Asn Thr Thr Asn Asn
1               5                   10                  15

Asn Asn Asn Gly Thr Ile Thr Leu
            20

<210> SEQ ID NO 141
<211> LENGTH: 24
<212> TYPE: PRT
<213> ORGANISM: HIV
<220> FEATURE:
<221> NAME/KEY: misc_feature
```

```
<222> LOCATION: 1
<223> OTHER INFORMATION: residue lipidated, for example with palmitoyl-
      Lys-Ser-Ser-

<400> SEQUENCE: 141

Asn Thr Thr Gln Leu Phe Asn Ser Thr Asn Asn Thr Thr Ser Thr
1               5                   10                  15

Asn Asn Asn Gly Thr Ile Thr Leu
            20

<210> SEQ ID NO 142
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 142

Asn Thr Thr Gln Leu Phe Asn Ser Thr Asn Asn Thr Thr Ser Asn
1               5                   10                  15

Asn Asn Asn Gly Thr Ile Thr Leu
            20

<210> SEQ ID NO 143
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 143

Asn Thr Thr Gln Leu Phe Asn Ser Thr Asn Asn Thr Thr Asn Thr
1               5                   10                  15

Asn Asn Asn Gly Thr Ile Thr Leu
            20

<210> SEQ ID NO 144
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 144

Asn Thr Thr Gln Leu Phe Asn Ser Thr Asn Asn Thr Thr Asn Asn
1               5                   10                  15

Asn Asn Asn Gly Thr Ile Thr Leu
            20

<210> SEQ ID NO 145
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-
```

-continued

```
<400> SEQUENCE: 145

Gly Asn Asn Asn Asn Thr Thr Glu Thr Phe Arg Pro Gly Gly Gly
1               5                   10                  15

<210> SEQ ID NO 146
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 146

Gly Asn Asn Asn Asn Thr Asn Glu Thr Phe Arg Pro Gly Gly Gly
1               5                   10                  15

<210> SEQ ID NO 147
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 147

Gly Asn Asn Asn Ser Thr Thr Glu Thr Phe Arg Pro Gly Gly Gly
1               5                   10                  15

<210> SEQ ID NO 148
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 148

Gly Asn Asn Asn Ser Thr Asn Glu Thr Phe Arg Pro Gly Gly Gly
1               5                   10                  15

<210> SEQ ID NO 149
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 149

Gly Asn Asn Thr Asn Thr Thr Glu Thr Phe Arg Pro Gly Gly Gly
1               5                   10                  15

<210> SEQ ID NO 150
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-
```

```
<400> SEQUENCE: 150

Gly Asn Asn Thr Asn Thr Asn Glu Thr Phe Arg Pro Gly Gly Gly
1               5                   10                  15

<210> SEQ ID NO 151
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 151

Gly Asn Asn Thr Ser Thr Thr Glu Thr Phe Arg Pro Gly Gly Gly
1               5                   10                  15

<210> SEQ ID NO 152
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 152

Gly Asn Asn Thr Ser Thr Asn Glu Thr Phe Arg Pro Gly Gly Gly
1               5                   10                  15

<210> SEQ ID NO 153
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 153

Gly Ala Asn Asn Asn Thr Thr Glu Thr Phe Arg Pro Gly Gly Gly
1               5                   10                  15

<210> SEQ ID NO 154
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 154

Gly Ala Asn Asn Asn Thr Asn Glu Thr Phe Arg Pro Gly Gly Gly
1               5                   10                  15

<210> SEQ ID NO 155
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-
```

```
<400> SEQUENCE: 155

Gly Ala Asn Asn Ser Thr Thr Glu Thr Phe Arg Pro Gly Gly Gly
1               5                   10                  15

<210> SEQ ID NO 156
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 156

Gly Ala Asn Asn Ser Thr Asn Glu Thr Phe Arg Pro Gly Gly Gly
1               5                   10                  15

<210> SEQ ID NO 157
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 157

Gly Ala Asn Thr Asn Thr Thr Glu Thr Phe Arg Pro Gly Gly Gly
1               5                   10                  15

<210> SEQ ID NO 158
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 158

Gly Ala Asn Thr Asn Thr Asn Glu Thr Phe Arg Pro Gly Gly Gly
1               5                   10                  15

<210> SEQ ID NO 159
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-

<400> SEQUENCE: 159

Gly Ala Asn Thr Ser Thr Thr Glu Thr Phe Arg Pro Gly Gly Gly
1               5                   10                  15

<210> SEQ ID NO 160
<211> LENGTH: 15
<212> TYPE: PRT
<213> ORGANISM: HIV
<220> FEATURE:
<221> NAME/KEY: misc_feature
<222> LOCATION: 1
<223> OTHER INFORMATION: residue lipidated, for example with palmitoyl-
      Lys-Ser-Ser-
```

<400> SEQUENCE: 160

Gly Ala Asn Thr Ser Thr Asn Glu Thr Phe Arg Pro Gly Gly Gly
1               5                   10                  15

<210> SEQ ID NO 161
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 161

Val Leu Ala Glu Ala Met Ser Gln Val Thr Asn Ser Asn Thr Met Met
1               5                   10                  15

<210> SEQ ID NO 162
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 162

Val Leu Ala Glu Ala Met Ser Gln Val Thr Asn Ser Asn Thr Ile Met
1               5                   10                  15

<210> SEQ ID NO 163
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 163

Val Leu Ala Glu Ala Met Ser Gln Val Thr Asn Ser Asn Ile Met Met
1               5                   10                  15

<210> SEQ ID NO 164
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 164

Val Leu Ala Glu Ala Met Ser Gln Val Thr Asn Ser Asn Ile Ile Met
1               5                   10                  15

<210> SEQ ID NO 165
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

```
<400> SEQUENCE: 165

Val Leu Ala Glu Ala Met Ser Gln Val Thr Asn Ser Ala Thr Met Met
1               5                   10                  15

<210> SEQ ID NO 166
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 166

Val Leu Ala Glu Ala Met Ser Gln Val Thr Asn Ser Ala Thr Ile Met
1               5                   10                  15

<210> SEQ ID NO 167
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 167

Val Leu Ala Glu Ala Met Ser Gln Val Thr Asn Ser Ala Ile Met Met
1               5                   10                  15

<210> SEQ ID NO 168
<211> LENGTH: 16
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 168

Val Leu Ala Glu Ala Met Ser Gln Val Thr Asn Ser Ala Ile Ile Met
1               5                   10                  15

<210> SEQ ID NO 169
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 169

Glu Ser Phe Arg Phe Gly Glu Glu Thr Thr Thr Pro Pro Gln Lys Arg
1               5                   10                  15

Glu Gln Tyr Pro Leu Ala Ser Leu
            20

<210> SEQ ID NO 170
<211> LENGTH: 24
<212> TYPE: PRT
<213> ORGANISM: HIV
<220> FEATURE:
<221> NAME/KEY: misc_feature
<222> LOCATION: 1
```

```
<223> OTHER INFORMATION: residue unlipidated or lipidated, for example
      with palmitoyl-Lys-Ser-Ser-

<400> SEQUENCE: 170

Glu Ser Phe Arg Phe Gly Glu Glu Thr Thr Thr Pro Pro Gln Lys Arg
1               5                   10                  15

Glu Gln Tyr Pro Leu Thr Ser Leu
            20

<210> SEQ ID NO 171
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 171

Glu Ser Phe Arg Phe Gly Glu Glu Thr Thr Thr Pro Pro Gln Lys Arg
1               5                   10                  15

Glu Leu Tyr Pro Leu Ala Ser Leu
            20

<210> SEQ ID NO 172
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 172

Glu Ser Phe Arg Phe Gly Glu Glu Thr Thr Thr Pro Pro Gln Lys Arg
1               5                   10                  15

Glu Leu Tyr Pro Leu Thr Ser Leu
            20

<210> SEQ ID NO 173
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 173

Glu Ser Phe Arg Phe Gly Glu Glu Thr Thr Thr Pro Pro Gln Lys Lys
1               5                   10                  15

Glu Gln Tyr Pro Leu Ala Ser Leu
            20

<210> SEQ ID NO 174
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 174
```

```
Glu Ser Phe Arg Phe Gly Glu Glu Thr Thr Thr Pro Pro Gln Lys Lys
1               5                   10                  15

Glu Gln Tyr Pro Leu Thr Ser Leu
            20

<210> SEQ ID NO 175
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 175

Glu Ser Phe Arg Phe Gly Glu Glu Thr Thr Thr Pro Pro Gln Lys Lys
1               5                   10                  15

Glu Leu Tyr Pro Leu Ala Ser Leu
            20

<210> SEQ ID NO 176
<211> LENGTH: 24
<212> TYPE: PRT
<213> ORGANISM: HIV
<220> FEATURE:
<221> NAME/KEY: misc_feature
<222> LOCATION: 1
<223> OTHER INFORMATION: residue unlipidated or lipidated, for example
      with palmitoyl-Lys-Ser-Ser-

<400> SEQUENCE: 176

Glu Ser Phe Arg Phe Gly Glu Glu Thr Thr Thr Pro Pro Gln Lys Lys
1               5                   10                  15

Glu Leu Tyr Pro Leu Thr Ser Leu
            20
```

MULTIVALENT HIV IMMUNOGENIC COMPOSITIONS COMPRISING A POOL OF LIPIDATED AND NONLIPIDATED PEPTIDES REPRESENTING GAG AND ENV VARIABLE REGIONS

This application is a national phase entry based on International Patent Application PCT/CA2006/000295, which is entitled to the benefit of and claims priority to U.S. provisional patent application Ser. No. 60/656,908, filed Mar. 1, 2005, which is herein incorporated by reference.

CROSS-REFERENCE TO RELATED APPLICATIONS

This application claims the benefit of and priority to U.S. Patent Application Ser. No. 60/656,908, filed on Mar. 1, 2005, the entirety of which is herein incorporated by reference.

FIELD OF THE INVENTION

The present invention relates generally to a vaccine composition, and more-specifically to an anti-HIV vaccine composition comprising a plurality of peptides.

BACKGROUND OF THE INVENTION

To date, no effective vaccine against HIV is commercially available. Different HIV clades predominate in certain regions of the world. For example, clade C is found predominantly in India, clade E in south east Asia, and clade B in North America. There is a need to develop vaccine that can be formulated either as broadly reactive against a variety of clades, or which is specifically tailored to a regional clade.

Infection of humans with HIV-1 results in immunity that while rarely protective, nonetheless creates strong negative pressure on viral replication in vivo manifested as antigenic variation. Indeed, a recent study has demonstrated that cellular immunity is directed against variable epitopes much more frequently than previously appreciated (Altfeld, M., et al., *J Virol* (2003), 77(13), 7330-7340).

A process for preparation of an immunogenic peptide mixture is described by Torres in co-owned U.S. patent application Ser. No. 10/072,084 (publication number 2002/0183484), herein incorporated by reference. According to this process, immunogenic eptitope sequences of a pathogen are assessed, and variability is evaluated. A peptide mixture is synthesized comprising different peptides representative of the frequency with which different amino acids are found at variable residues of selected epitopes of pathogenic proteins. Although this document teaches the specific method by which a peptide mixture can be formulated, there is still a need to formulate specific anti-HIV vaccine compositions.

SUMMARY OF THE INVENTION

It is an object of the present invention to obviate or mitigate at least one disadvantage of previous attempts at formulating HIV vaccines. Surprisingly, the inventive composition, which is directed to multi-clade HIV immunity and which targets only hypervariable HIV epitopes, elicits a broadly reactive CTL and T-helper cell response.

According to an embodiment of the invention, there is provided an anti-HIV vaccine composition comprising mixtures of isolated peptides, said mixtures being formulated on the basis of at least two HIV proteins having a hypervariable region, said isolated peptide mixtures representing variants of a hypervariable region of the HIV proteins, each of said hypervariable regions comprising a plurality of variable amino acid residues represented by two or more amino acids; in combination with a pharmaceutically acceptable carrier; wherein the composition comprises at least one of SEQ ID NO:1 to SEQ ID NO:176, or peptide analogues thereof.

According to another embodiment of the invention there is provided an anti-HIV vaccine composition comprising at least one of SEQ ID NO:1 to SEQ ID NO: 176, or peptide analogues thereof; in combination with a pharmaceutically acceptable carrier.

The inventive composition, which is directed to multi-clade HIV immunity, and which targets only hypervariable HIV epitopes, elicits a broadly reactive CTL and T-helper cell response.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 2 depicts the 16 peptides in the peptide mixture V1 (SEQ ID NO:1 to SEQ ID NO:16) based on HIV-1, indicating variable sites.

FIG. 3 illustrates the quantities of each of the amino acids in V1.

FIG. 4 provides characteristics of V1, such as molecular weight, protein, counter ion and lipid content.

FIG. 5 depicts the 16 peptides in the peptide mixture V2 (SEQ ID NO:17 to SEQ ID NO:32)) based on HIV-1, indicating variable sites.

FIG. 6 illustrates the quantities of each of the amino acids in V2.

FIG. 7 provides characteristics of V2.

FIG. 8 depicts 16 peptides in the peptide mixture V3 (SEQ ID NO:33 to SEQ ID NO:48) based on HIV-1, indicating variable sites.

FIG. 9 illustrates the quantities of each of the amino acids in V3.

FIG. 10 provides characteristics of V3, such as molecular weight, protein, counter ion and lipid content.

FIG. 11 depicts the 16 peptides in the peptide mixture V4 (SEQ ID NO:49 to SEQ ID NO:64) based on HIV-1, indicating variable sites.

FIG. 12 illustrates the quantities of each of the amino acid in V4.

FIG. 13 provides characteristics of V4, such as molecular weight, protein, counter ion and lipid content.

FIG. 14 depicts the 16 peptides in the peptide mixture V5 (SEQ ID NO:65 to SEQ ID NO:80) based on HIV-1, indicating variable sites.

FIG. 15 illustrates the quantities of each of the amino acids in V5.

FIG. 16 provides characteristics of V5.

FIG. 17 depicts the 16 peptides in the peptide mixture V6 (SEQ ID NO:81 to SEQ ID NO:96) based on HIV-1, indicating variable sites.

FIG. 18 illustrates the quantities of each of the amino acids in V6.

FIG. 19 provides characteristics of V6, such as molecular weight, protein, counter ion and lipid content.

FIG. 20 depicts the 16 peptides in the peptide mixture V7 (SEQ ID NO:97 to SEQ ID NO:112) based on HIV-1, indicating variable sites.

FIG. 21 illustrates the quantities of each of the amino acids in V7.

FIG. 22 provides characteristics of V7, such as molecular weight, protein, counter ion and lipid content.

FIG. 23 depicts the 16 peptides in the peptide mixture V8 (SEQ ID NO:113-SEQ ID NO:128) based on HIV-1, indicating variable sites.

FIG. 24 illustrates the quantities of each of the amino acids in V8.

FIG. 25 provides characteristics of V8, such as molecular weight, protein, counter ion and lipid content.

FIG. 26 depicts the 16 peptides in the peptide mixture V9 (SEQ ID NO:129 to SEQ ID NO:144) based on HIV-1, indicating variable sites.

FIG. 27 illustrates the quantities of each of the amino acids in V9.

FIG. 28 provides characteristics of V9, such as molecular weight, protein, counter ion and lipid content.

FIG. 29 depicts the 16 peptides in the peptide mixture V10 (SEQ ID NO:145 to SEQ ID NO:160) based on HIV-1, indicating variable sites.

FIG. 30 illustrates the quantities of each of the amino acids in V10.

FIG. 31 provides characteristics of V10, such as molecular weight, protein, counter ion and lipid content.

FIG. 32 depicts the 8 peptides in the peptide mixture V11 (SEQ ID NO:161 to SEQ ID NO:168) based on HIV-1, indicating variable sites.

FIG. 33 illustrates the quantities of each of the amino acids in V11.

FIG. 34 provides characteristics of V11, such as molecular weight, protein, counter ion and lipid content.

FIG. 35 depicts the 8 peptides in the peptide mixture V12 (SEQ ID NO:169 to SEQ ID NO:176) based on HIV-1, indicating variable sites.

FIG. 36 illustrates the quantities of each of the amino acids in V12.

FIG. 37 provides characteristics of V12, such as molecular weight, protein, counter ion and lipid content.

DETAILED DESCRIPTION

Figure 1:
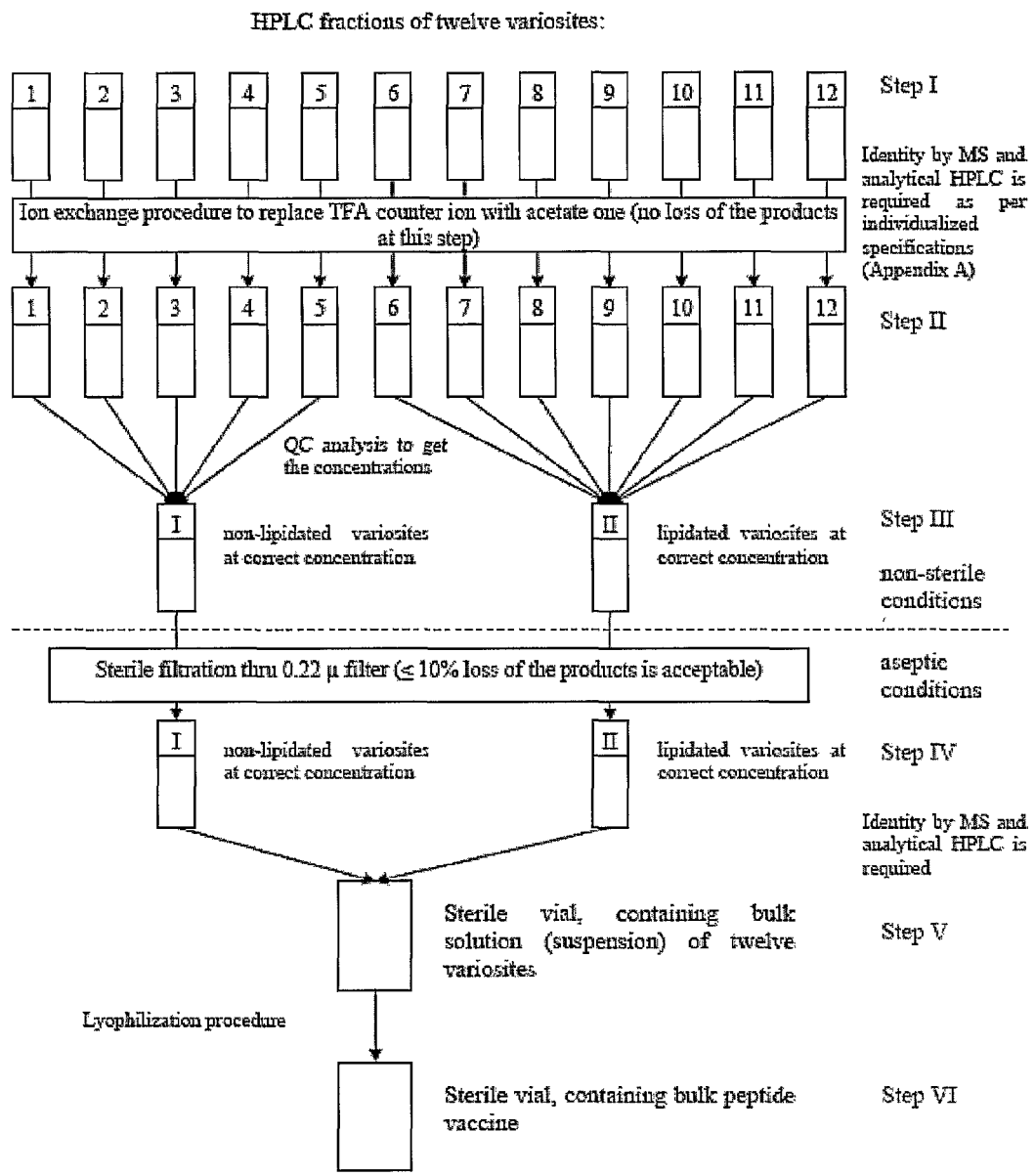
FIG. 1 illustrates a method by which the vaccine is assembled.

Generally, the invention relates to a vaccine composition, and more specifically to an anti-HIV vaccine composition comprising mixtures of isolated peptides, said mixtures being formulated on the basis of at least two HIV proteins having a hypervariable region, said isolated peptide mixtures representing variants of a hypervariable region of the HIV proteins, each of said hypervariable regions comprising a plurality of variable amino acid residues represented by two or more amino acids; in combination with a pharmaceutically acceptable carrier; wherein the composition comprises at least one of SEQ ID NO:1 to SEQ ID NO:176, or peptide analogues thereof. The peptides may or may not have a conservative substitution therein. Advantageously, the HIV vaccine composition prepared according to the invention elicits a broadly reactive cellular immunity, targeting only hypervariable epitopes of HIV-1.

The plurality of variable amino acid residues may comprise three or more residues. At least one of said HIV proteins is an envelope protein or HIV-1 gp120.

The isolated peptides are lipidated peptides SEQ ID NO:81 to SEQ ID NO:176, or peptide analogues thereof. They may comprise at least two of the following mixtures of isolated peptides: (a) eight or more of SEQ ID NO:1 to SEQ ID NO:16, or peptide analogues thereof; (b) eight or more of SEQ ID NO:17 to SEQ ID NO:32, or peptide analogues thereof; (c) eight or more of SEQ ID NO:33 to SEQ ID NO:48, or peptide analogues thereof; (d) eight or more of SEQ ID NO:49 to SEQ ID NO:64, or peptide analogues thereof; or (e) eight or more of SEQ ID NO:65 to SEQ ID NO:80, or peptide analogues thereof.

Optionally, at least one of said mixtures of isolated peptides represents a hypervariable region of HIV-1 Gag protein. The peptides within said mixture of isolated peptides may represent a hypervariable region of HIV-1 Gag protein which comprises SEQ ID NO:161 to SEQ ID NO:176, or peptide analogues thereof.

The anti-HIV vaccine composition may comprise the following isolated peptides: (a) SEQ ID NO:161 to SEQ ID NO:168, or peptide analogues thereof; (b) SEQ ID NO:169 to SEQ ID NO:176, or peptide analogues thereof, or (c) SEQ ID NO:1 to SEQ ID NO: 176. Typically, the composition comprises at least one of SEQ ID NO:1 to SEQ ID NO: 176, or peptide analogues thereof, in combination with a pharmaceutically acceptable carrier.

The composition can be formulated using oligonucleotides encoding the isolated peptides, or peptide analogues thereof. For example, the oligonucleotides can be delivered in viral or non-viral vectors.

When the anti-HIV vaccine composition comprises lipidated peptides a lipidated oligopeptide spacer may be attached thereto. The spacer can comprise 3 (a tripeptide) or fewer amino acids. In one example, the spacer comprises Lys-Ser-Ser wherein the Lys residue is lipidated. The spacer can be attached to the N-terminal residue of the isolated peptide. Alternatively, the lipidated peptides are lipidated at the N-terminal or C-terminal amino acid residue.

As used in the present invention, the term "hypervariable region" refers to a portion of the HIV protein which shows a high degree of amino acid variation from molecule to molecule. This is likely different from a hypervariable nucleotide region, which may or may not result in amino acid variation. As would be understood in the art, a hypervariable region can be determined in situations where a particular amino acid is present at a given position in less than or equal to a predetermined percentage of sequences. For example, if the predetermined percentage is 90%, then this means that a particular amino acid is present at a given position in less than or equal to 90% of the sequences analyzed in a typical sequence database. In the present invention, the isolated peptide mixtures represent variants of a hypervariable region of the HIV proteins. Each of the hypervariable regions comprises a plurality of variable amino acid residues represented by two or more amino acids. The plurality of peptides as referred to herein may comprise three or more residues.

As used in the present invention, a "conservative substitution" means a substitution of an individual residue with another residue, as would be readily understood by the person of ordinary skill in the art. For the peptides prepared according to the invention, it may be appropriate to substitute at individual residues other amino acids that are related in structure, such as sulfur-containing amino acids, negatively charged amino acids, etc. Exemplary substitutions include, but are not limited to, Arg-Lys, Glu-Asp, Gln-Asn, Thr-Ser, Phe-Tyr, or Leu-Ile. In this way, the replacement of an amino acid with a conservative substitution would be considered equivalent. Reference is made to such substitution matrices as PAM250 and BLOSUM62, which show, for example that replacement of lysine by arginine, or valine with isoleucine are considered conservative substitutions.

As used in the present invention, a "peptide analogue" refers to a peptide of the present invention which comprises a conservative substitution as described above, a deletion of an amino acid, or an insertion of an amino acid, such that the conservative substitution, deletion or insertion has no material effect on the function of the peptide.

According to an embodiment of the invention, there is provided an anti-HIV vaccine composition comprising mixtures of isolated peptides. The mixtures are formulated on the basis of at least two HIV proteins, each of which has a hypervariable region. The composition comprises at least one of SEQ ID NO:1 to SEQ ID NO:176 or peptide analogues thereof (which may or may not have a conservative substitution therein). It would be understood that peptides of any length could be used in the composition of the present invention. Ideally, peptides having 15 or more residues are used, but fragments of any length, particularly shorter than those presented herein, may also be used. Further, any number of these peptides could be included in the vaccine composition of the present invention. The peptide mixtures are formulated in combination with a pharmaceutically acceptable carrier.

At least one of the HIV proteins may be an envelope protein. Optionally, one of the HIV proteins is HIV-1 gp120, in which case the isolated peptide mixtures may be selected from the group consisting of SEQ ID NO:1 to SEQ ID NO:160, or peptide analogues thereof.

A portion of said isolated peptides may be lipidated peptides, for example, those selected from the group consisting of SEQ ID NO:81 to SEQ ID NO:160, or peptide analogues thereof.

As a specific example, an anti-HIV vaccine composition comprises at least two of the following mixtures of isolated peptides:

(a) eight or more of SEQ ID NO:1 to SEQ ID NO:16, or peptide analogues thereof;

(b) eight or more of SEQ ID NO:17 to SEQ ID NO:32, or peptide analogues thereof;

(c) eight or more of SEQ ID NO:33 to SEQ ID NO:48, or peptide analogues thereof;

(d) eight or more of SEQ ID NO:49 to SEQ ID NO:64, or peptide analogues thereof; and (e) eight or more of SEQ ID NO:65 to SEQ ID NO:80, or peptide analogues thereof.

According to an embodiment of the invention, at least one of the mixtures of isolated peptides may represent a hypervariable region of HIV-1 Gag protein, in which case, the mixture of isolated peptides representing a hypervariable region of HIV-1 Gag protein may be selected from the group consisting of SEQ ID NO:161 to SEQ ID NO:176, or peptide analogues thereof, which may or may not be lipidated.

As a specific example, the anti-HIV vaccine may include the following isolated peptides: SEQ ID NO:161 to SEQ ID NO:168, or peptide analogues thereof; and SEQ ID NO:169 to SEQ ID NO:176, or peptide analogues thereof.

An exemplary anti-HIV composition may comprise SEQ ID NO:1 to SEQ ID NO: 176 or peptide analogues thereof, in combination with a pharmaceutically acceptable carrier.

The inventive composition, which is directed to multi-clade HIV immunity, and which targets only hypervariable HIV epitopes, elicits a broadly reactive CTL and T-helper cell response.

SEQ ID NO:1 to SEQ ID NO:176 are peptides which may be used in combination according to an aspect of the invention. Although all peptides of SEQ ID NO:1 to SEQ ID NO:176 may be used in combination as the vaccine formulation, sub-groups of these peptides could be used together according to the invention.

Conservative substitution of amino acid residues within any of the peptides shown in SEQ ID NO:1 to SEQ ID NO:176 may also be used according to the invention.

Preparation of the Vaccine Composition: The vaccine may be prepared according to the methodology described by Torres in U.S. patent application Ser. No. 10/072,084 (publication number 2002/0183484), or by any alternative methodology acceptable to one skilled in the art. For example, oligonucleotides encoding these peptides may be inserted in viral or non-viral vectors for delivery. Peptides may be synthesized individually in and mixed together to accomplish an acceptable composition. Any variety of different modes by which these peptide antigens may be prepared is acceptable for use with the invention.

In selection of the proteins from which hypervariable isotopes are to be assessed, according to an embodiment of the invention, selection of more than one viral gene product (protein) may have the advantage that different types of responses will be induced by the vaccine. For example, a cytoplasmic protein and an envelope protein may be selected. In the case that two or more viral gene products are selected from which a hypervariable epitope is represented, a broad based reactivity can be accomplished. From each of the proteins chosen, one or more hypervariable epitope regions can be targeted, for example, two hypervariable epitope regions from each protein, to arrive at the peptide mixture. From each hypervariable epitope region, the peptide length is selected, and within the peptide, a plurality of variable residues are selected. Each variable residue having at least two optional amino acids, found naturally occurring in sequenced versions of the virus.

In this way, a high degree of variability is represented. For example, three or four variable residues may be represented in the mixture of peptides, each having two or more different amino acids represented in the sequenced database records for HIV variants. If two variable residues are indicated in a hypervariable region, $2^2$ different peptides would be used in the mixture representing that particular region. If three or four variable residues are indicated in a hypervariable region, the number of peptides in the resulting mixture would be $2^3$ and $2^4$, respectively, and so on.

Once the proteins, hypervariable regions, peptide lengths, and variable residues are selected, the synthesis of the peptide mixtures occurs, according to any acceptable method of peptide synthesis.

According to the synthesis disclosed by Torres in U.S. patent application Ser. No. 10/072,084 (publication number 2002/0183484), peptide mixtures are synthesized with each different peptide sequence represented in roughly equimolar quantities. However, there is no requirement to provide equimolar quantities of the individual peptides.

The peptides can be lipidated by any conventional or acceptable method known in the art to introduce lipids to the vaccine. This can be achieved by attaching one or more lipid moities to the peptides of the vaccine composition. There are several ways for introducing lipids. The lipids can be attached via an oligopeptide spacer at either the N- or C-terminus of the vaccine peptides between the peptide and the lipid moiety. The oligopeptide can comprise any number of amino acid residues and the lipid moiety can be attached to any of the amino acid residues in the oligopeptide. Typically, the lipid moiety is bulky and is added to the N-terminus end of the oligopeptide such that it is separated from the amino acids of the vaccine peptide to prevent any possible interference with functional portions, for example, of the amino acids in the vaccine peptides. A suitable spacer is selected for the particular application used. Usually, the spacer comprises no more than 3 amino acids which are relatively simple in structure (such as, but not limited to, serine, glycine or asparagine, for example). Serine is suitable as it increases the solubility of lipidated peptides in water. Also, it is advantageous to include lysine in the oligopeptide, which permits the addition of two lipid moieties. Alternatively, the vaccine peptides can be lipidated directly without using a spacer at all. In this way, either the N- or C-terminal amino acid residue of the vaccine peptide is itself lipidated. Finally, the vaccine peptide can undergo total lipidation, i.e., one or more residues of the peptide can be lipidated. One advantage of total lipidation is that the vaccine peptides can be purified first, then lipidated. This overcomes some of the problems associated with the purification of lipidated peptides.

Peptides need not be lipidated, but it may be advantageous for certain peptides to be lipidated with any acceptable lipid, such as palmitic acid, so as to allow a peptide to pass through lipid bilayer. Peptides incorporating lipidation may benefit from placement of a KSS motif at their N-termini. The peptides incorporating lipidation may contain 1 or more lipid moieties, for example, two lipid moieties per peptide. Lipidated peptides may move more easily through cytoplasm and lipid bilayer, and may result in an enhanced CTL response.

In order to formulate a vaccine that is clade-specific, the proteins selected may contain hypervariable regions with selected variable amino acids that are characteristic of the variability found within the clade of interest. This allows the vaccine to take advantage of regional variability while targeting regional distinctiveness. To formulate a vaccine that has less regional distinctiveness, the variable residues selected for the peptides in the mixtures may be representative of a broader base of variability from a variety of different regions. For example, a vaccine formulated to provide in India would target variable residues particular to clade C sequences. A vaccine formulated to provide in South East Asia could target variable residues characteristic of clade E sequences.

EXAMPLES

Example 1

Anti HIV-1 Peptide Composition

The vaccine composition is based on 12 peptide-based components in combination with an adjuvant and a buffer. The exact composition of the 12 components is detailed below. Two different proteins were used in formulation of the composition, specifically: gp120, an envelope protein, and Gag protein. Peptides mixtures used for this embodiment of the invention were determined by analysing HIV clades from around the world, (clades A, B, C, D and E), and arriving at hypervariable regions common to different clades. Clade B, which is the predominant clade found in North America, is most highly characterized, and is well-represented in the selected hypervariable regions of this example. however, equal weight was given to data from all clades when selecting hypervariable regions. Briefly, once the proteins and hypervariable regions were selected for the vaccine, the method of Torres described in co-owned U.S. patent application Ser. No. 10/072,084 (publication number 2002/0183484), was used to arrive at individual peptide mixtures.

The 12 peptide-based components are as follows: 5 non-lipidated formulations, each comprised of 16 unique species (V1-V5); 5 formulations that are the same as the non-lipidated formulations, but each having a lipid tail added (V6-V10); and 2 additional lipidated formulations, each with 8 unique variants (V11-V12). Formulations V1-V10 are derived from 5 hypervariable regions in the gp120 envelope protein, while formulations V11 and V12 are from variable regions in a Gag protein. According to this example, the vaccine is the combination of all these components. The peptide compositions V1 to V12 are prepared using any possible peptide synthesis, and may be prepared using the method described in co-owned U.S. patent application Ser. No. 10/072,084 (publication number 2002/0183484), herein incorporated by reference. The composition of the 12 components V1 to V12 is detailed below.

FIG. 1 provides a diagrammatic representation of a method by which the vaccine can be assembled, once the crude peptide-based components have been prepared. Briefly, HPLC purified fractions of twelve components or "variosites" V1 to V12 are subjected individually to an ion exchange procedure to replace a TFA counter ion with an acetate ion. No loss of the peptide products is seen at this step. Identification by MS and analytical HPLC may be conducted to ensure identification of V1 to V12. Components V1 to V5 are subjected to QC analysis and concentrated. These non-lipidated peptides are pooled into a non-lipidated mixture. Components V6 to V12 are pooled to form a lipidated mixture. These procedures may be conducted under non-sterile conditions. Both of the pooled mixtures are then sterile filtered, for example through a 0.22 micron filter, and a loss of up to about 10% of the product may be experienced at this stage. The remaining procedure is conducted under aseptic conditions. The lipidated and non-lipidated mixtures are then pooled, and identity can be conducted using MS and analytical HPLC. A sterile solution (or suspension) is formed containing the twelve variosite mixtures. The solution is then lyophilized to produce a sterile vial of sterile lyophilized peptide vaccine. This bulk product may be stored frozen at −20° C. or below.

A lipidated oligopeptide was used for lipidating the isolated vaccine polypeptides in this example. The peptides were lipidated at their N-termini. A lysine-serine-serine (Lys-Ser-Ser) tripeptide was covalently attached to the N-terminus of the peptides of SEQ ID NOs: 1 to 80, where the Lys residue was lipidated. The resulting lipidated peptides are SEQ ID NOs: 81 to 160.

For lipidation using a lipidated peptide, any known protocol can be used. In the example of the present invention, lipidation is performed as follows. Upon completion of the synthesis of a mixed peptide composition (V6-V12) on the synthesiser, the resin is removed from the column and placed into a vial. Dissolve 10 eq. of the Palmitic Acid, 10 eq. of TBTU and 10 eq. HOBT (all relative to the resin) in DMF (10 ml/0.1 mmol resin). Add the solution to the peptidyl resin in the vial. Add 20 eq. (relative to the resin) of the DIPEA. Adjust pH to 8-9 by adding DIPEA drop-wise. Seal the vial with a screw cap and shake the mixture overnight (at least 12 hours).

To formulate the vaccine for injection, three sterile components are used. The sterile peptide vaccine (100 µg), containing an equal amount (8.333 µg) of each of V1 to V12, is combined with Montanide™ adjuvant (500 µL) as Montanide ISA 51 (Seppic) emulsion, which has been sterile sealed and with phosphate buffered saline (PBS) pH 7.4, in an amount of 500 µL of a sterile injectable quality.

FIG. 2 depicts the 16 peptides found in V1, along with the molecular weights of each peptide. In this figure, as with other figures depicting the peptides in V2 to V12, "*" denotes a variable site at which more than one amino acid is used in the peptide formulation. These 16 peptides are listed as SEQ ID NO:1 to SEQ ID NO:16, respectively. As shown in FIG. 2, sixteen peptides are found in this peptide mixture. roughly in equimolar quantities. Each of the 16 peptides contains 27 amino acids. At residues 2, 4, 6 and 20, variable amino acids may be present, according to the sequences found in databases representing variants of HIV. All of the combinations of peptides are represented. Thus, $2^4$ (16) variants of this hypervariable residue are found in the mixture V1. FIG. 3 illustrates the amount of each amino acid present in V1.

FIG. 4 provides characterizing details of V1, such as molecular weight, protein, counter ion and lipid content.

FIG. 5 depicts the 16 peptides found in V2, along with the molecular weights of each peptide. These 16 peptides are listed as SEQ ID NO:17 to SEQ ID NO:32, respectively. FIG. 6 illustrates the amount of each amino acid present in V2. FIG. 7 provides characterizing details of V2.

FIG. 8 depicts the 16 peptides found in V3, along with the molecular weights of each peptide. These 16 peptides are listed as SEQ ID NO:33 to SEQ ID NO:48, respectively. FIG. 9 illustrates the amount of each amino acid present in V3. FIG. 10 provides characterizing details of V3.

FIG. 11 depicts the 16 peptides found in V4, along with the molecular weights of each peptide. These 16 peptides are listed as SEQ ID NO:49 to SEQ ID NO:64, respectively. FIG. 12 illustrates the amount of each amino acid present in V4. FIG. 13 provides characterizing details of V4.

FIG. 14 depicts the 16 peptides found in V5, along with the molecular weights of each peptide. These 16 peptides are listed as SEQ ID NO:65 to SEQ ID NO:80, respectively. FIG. 15 illustrates the amount of each amino acid present in V5. FIG. 16 provides characterizing details of V5.

FIG. 17 depicts the 16 peptides found in V6, along with the molecular weights of each peptide. These 16 peptides are listed as SEQ ID NO:81 to SEQ ID NO:96, respectively. These peptides are lipidated. FIG. 18 illustrates the amount of each amino acid present in V6. FIG. 19 provides characterizing details of V6.

FIG. 20 depicts the 16 peptides found in V7, along with the molecular weights of each peptide. These 16 peptides are listed as SEQ ID NO:97 to SEQ ID NO:112, respectively. These peptides are lipidated. FIG. 21 illustrates the amount of each amino acid present in V7. FIG. 22 provides characterizing details of V7.

FIG. 23 depicts the 16 peptides found in V8, along with the molecular weights of each peptide. These 16 peptides are listed as SEQ ID NO:113 to SEQ ID NO:128, respectively. These peptides are lipidated. FIG. 24 illustrates the amount of each amino acid present in V8. FIG. 25 provides characterizing details of V8.

FIG. 26 depicts the 16 peptides found in V9, along with the molecular weights of each peptide. These 16 peptides are listed as SEQ ID NO:129 to SEQ ID NO:144, respectively. These peptides are lipidated. FIG. 27 illustrates the amount of each amino acid present in V9. FIG. 28 provides characterizing details of V9.

FIG. 29 depicts the 16 peptides found in V10, along with the molecular weights of each peptide. These 16 peptides are listed as SEQ ID NO:145 to SEQ ID NO:160, respectively. These peptides are lipidated. FIG. 30 illustrates the amount of each amino acid present in V10. FIG. 31 provides characterizing details of V10.

FIG. 32 depicts the 8 peptides found in V11, along with the molecular weights of each peptide. These 8 peptides which may or may not be lipidated are listed as SEQ ID NO:161 to SEQ ID NO:168, respectively. FIG. 33 illustrates the amount of each amino acid present in V11. FIG. 34 provides characterizing details of V11.

FIG. 35 depicts the 8 peptides found in V12, along with the molecular weights of each peptide. These 8 peptides which may or may not be lipidated are listed as SEQ ID NO:169 to SEQ ID NO:176, respectively. FIG. 36 illustrates the amount of each amino acid present in V12. FIG. 37 provides characterizing details of V12.

Figure 38:
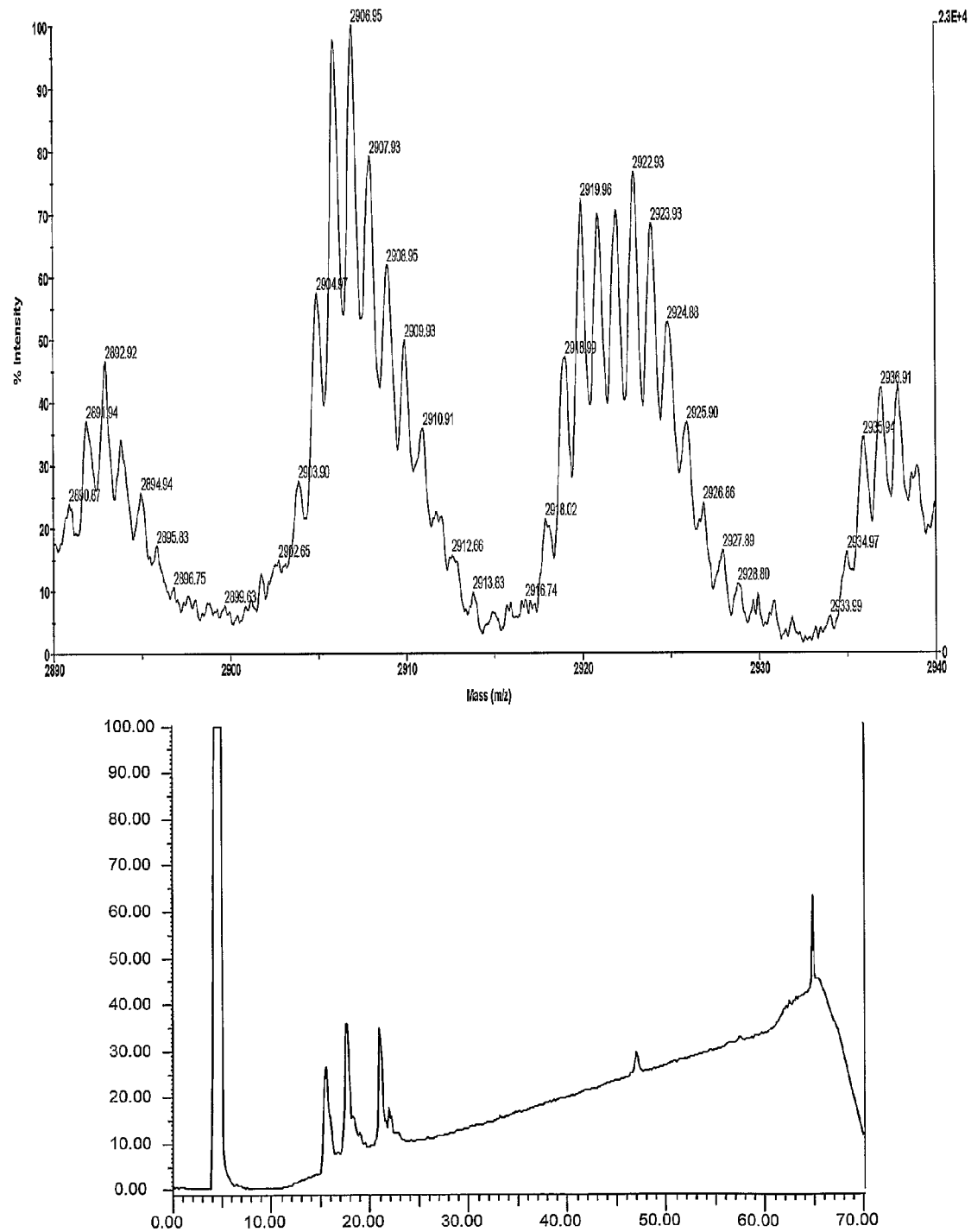
FIG. 38 depicts MALDI mass spec and analytical HPLC of V1.

FIG. 38 depicts the MALDI mass spectrum and an analytical HPLC spectrum of the crude peptide mixture V1.

Figure 39:
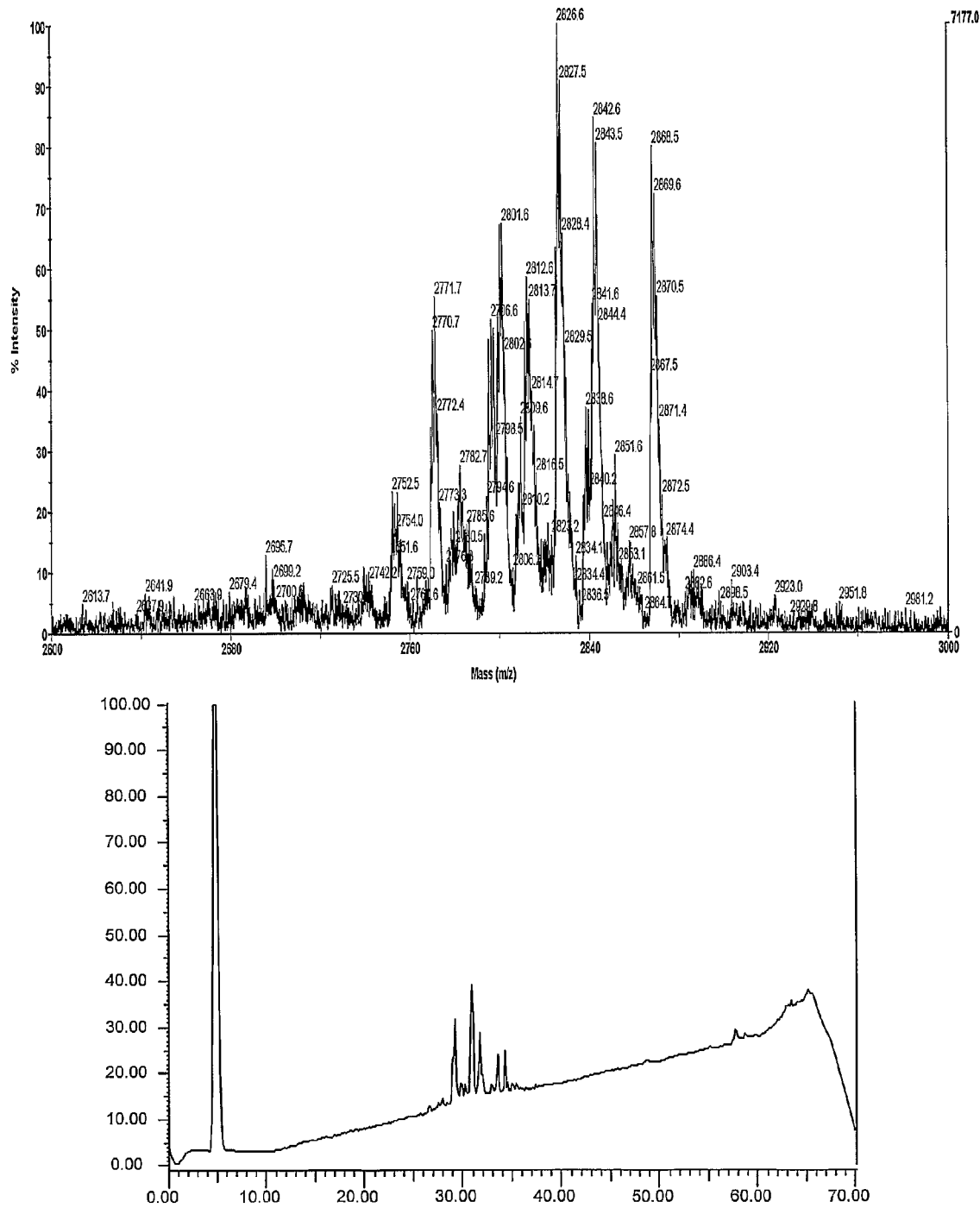
FIG. 39 depicts MALDI mass spec and analytical HPLC of V2.

FIG. 39 depicts the MALDI mass spectrum and an analytical HPLC spectrum of the crude peptide mixture V2.

Figure 40:
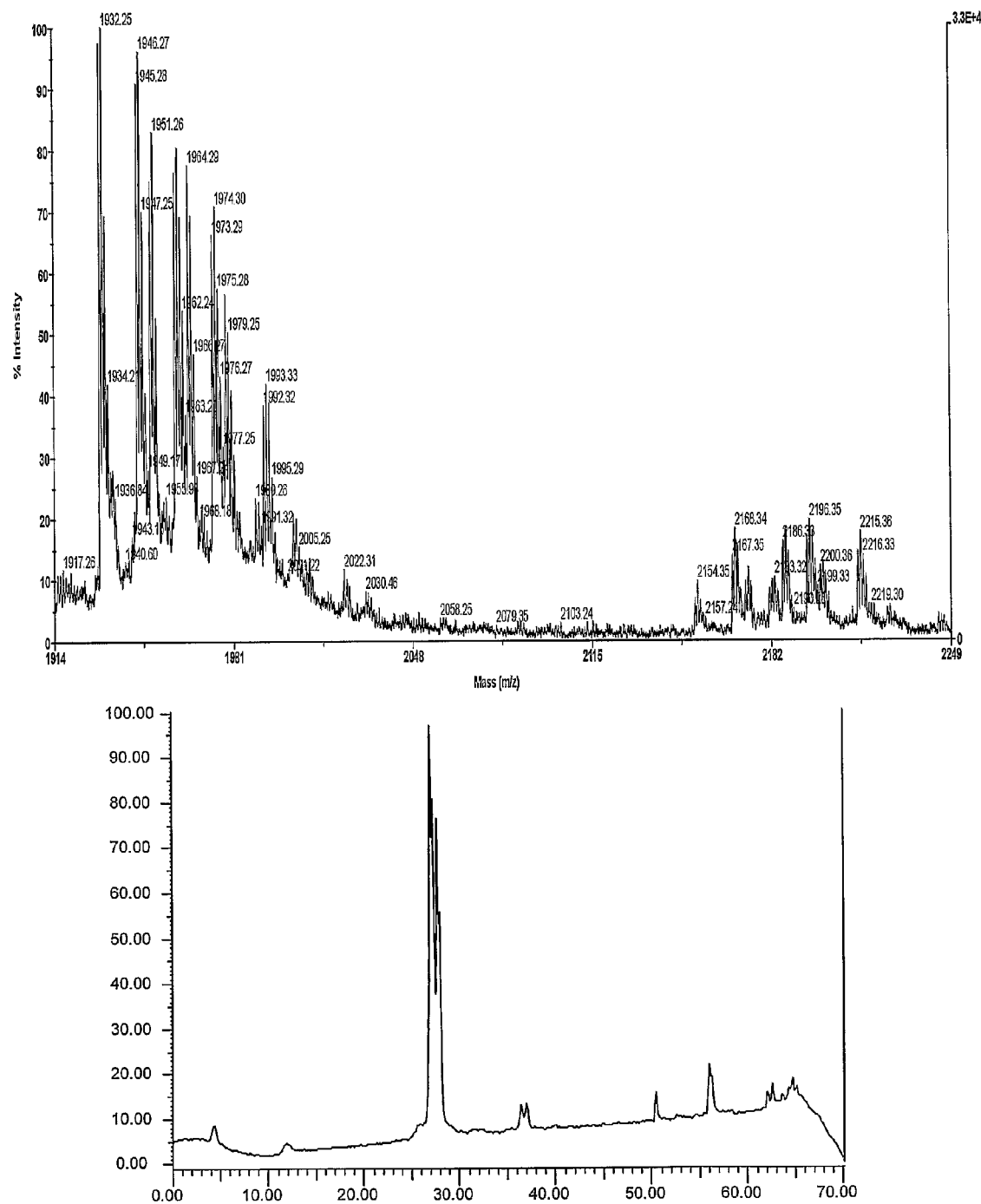
FIG. 40 depicts MALDI mass spec and analytical HPLC of V3.

FIG. 40 depicts the MALDI mass spectrum and an analytical HPLC spectrum of the crude peptide mixture V3.

Figure 41:
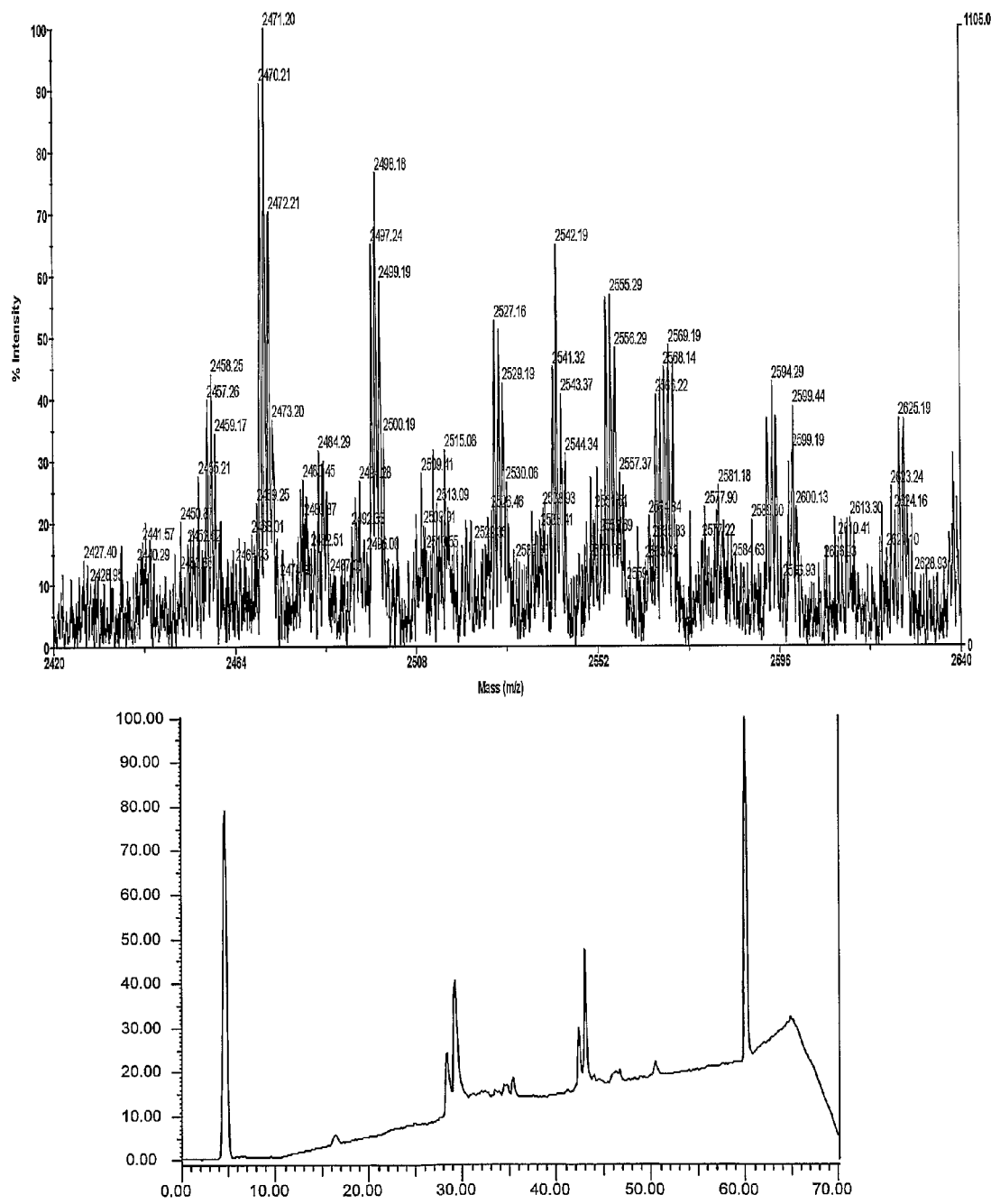
FIG. 41 depicts MALDI mass spec and analytical HPLC of V4.

FIG. 41 depicts the MALDI mass spectrum and an analytical HPLC spectrum of the crude peptide mixture V4.

Figure 42:
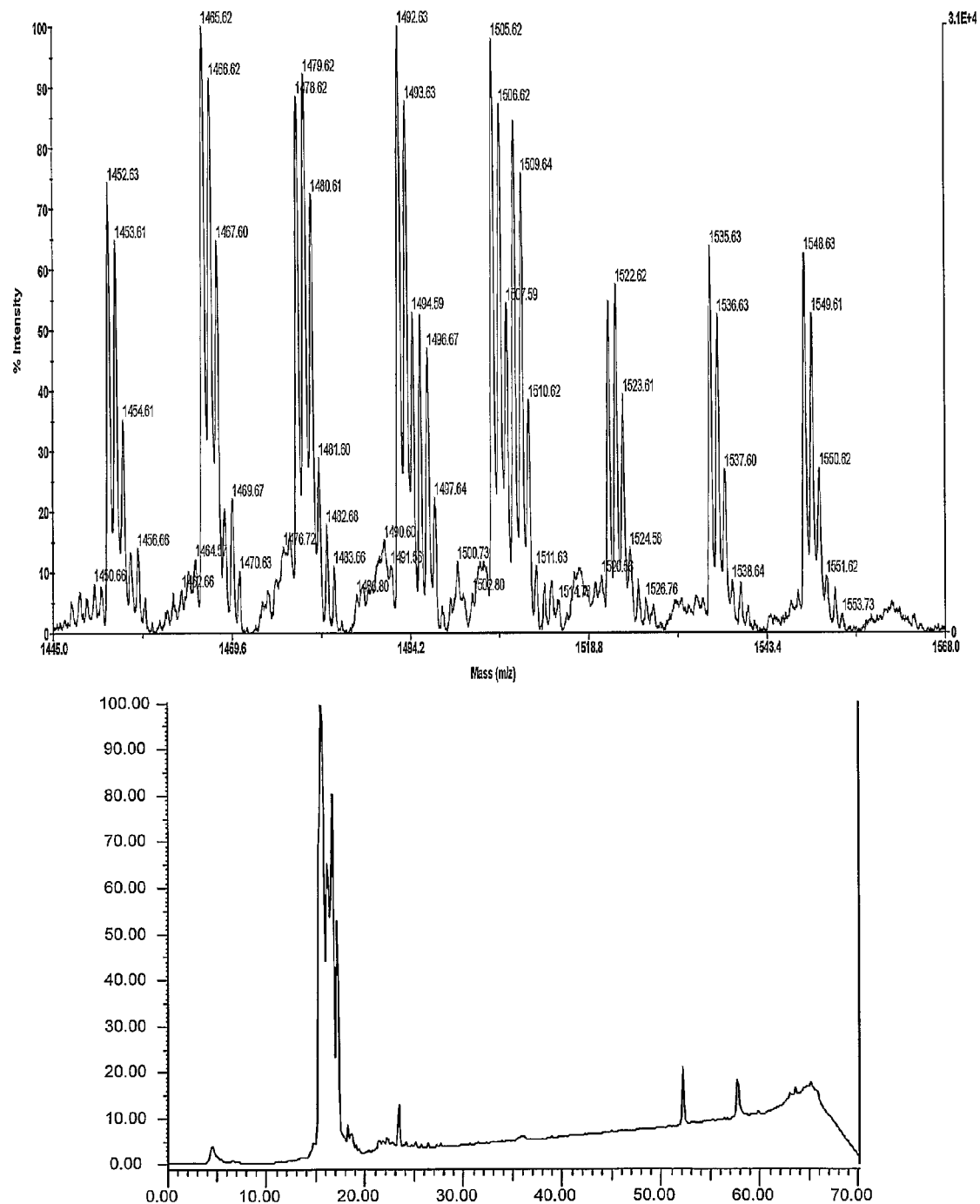
FIG. 42 depicts MALDI mass spec and analytical HPLC of V5.

FIG. 42 depicts the MALDI mass spectrum and an analytical HPLC spectrum of the crude peptide mixture V5.

Figure 43:
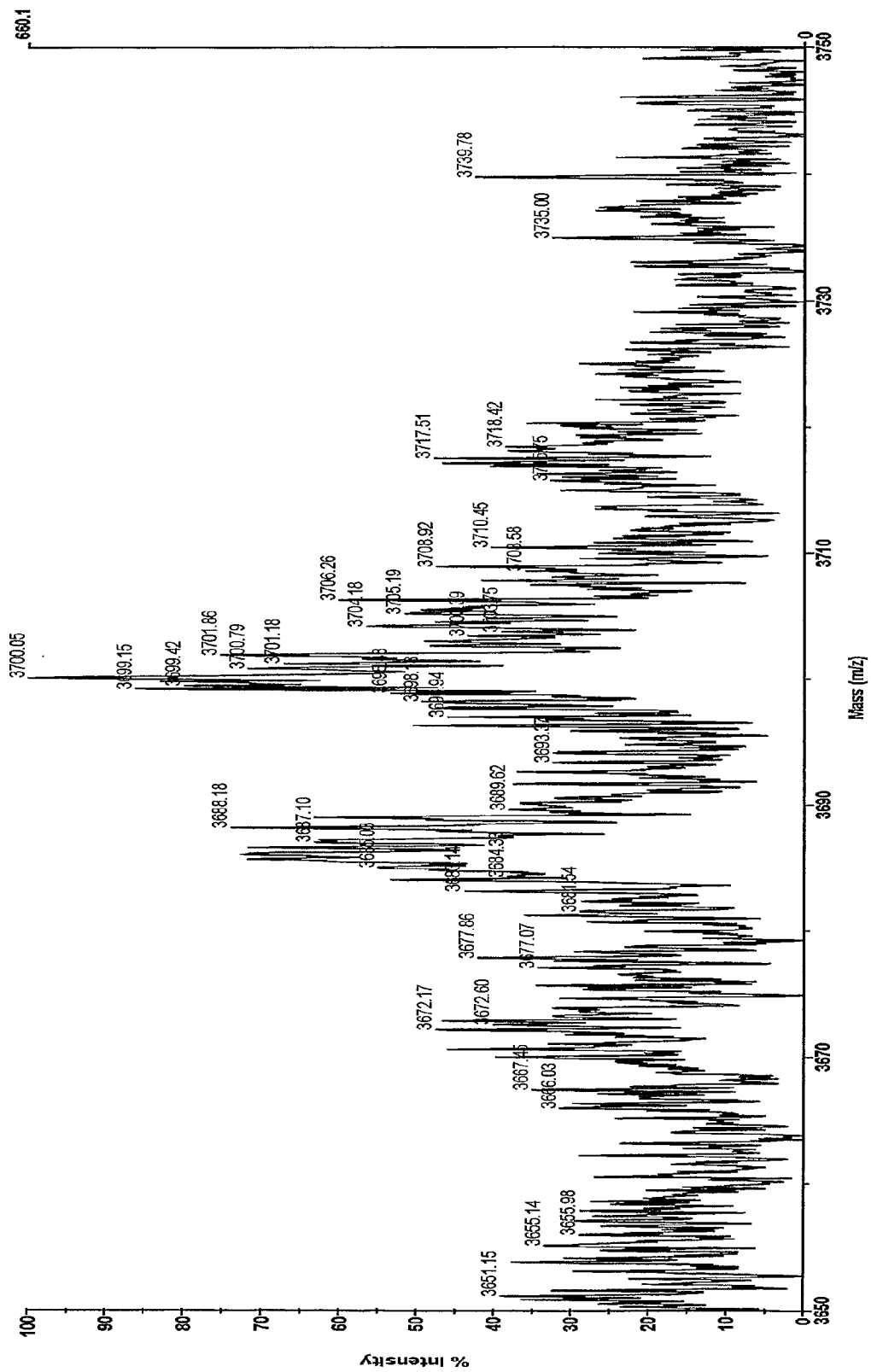
FIG. 43 depicts the MALDI mass spec of V6.

FIG. 43 depicts the MALDI mass spectrum of crude peptide mixture V6.

Figure 44:
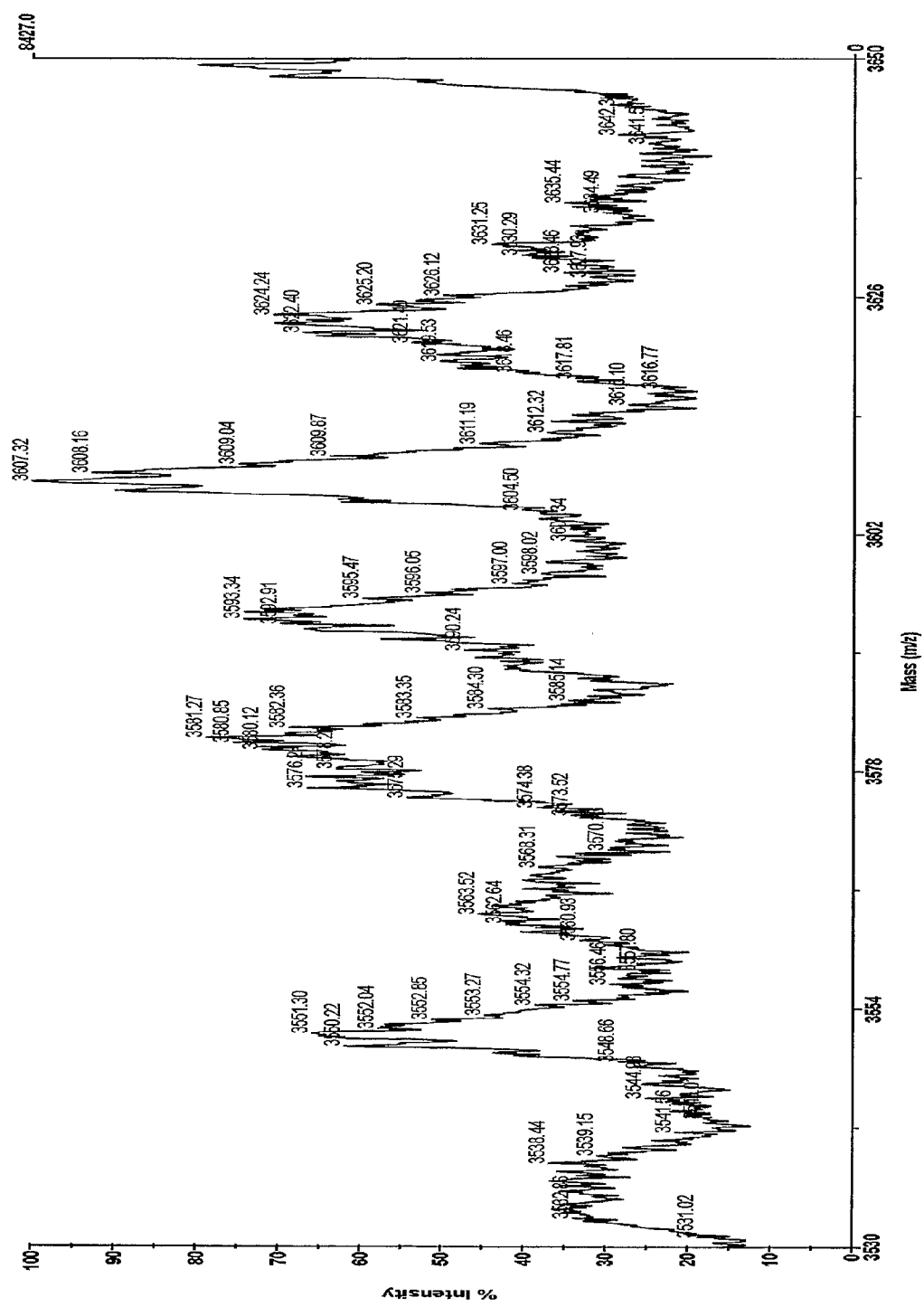
FIG. 44 depicts the MALDI mass spec of V7.

FIG. 44 depicts the MALDI mass spectrum of crude peptide mixture V7.

Figure 45:
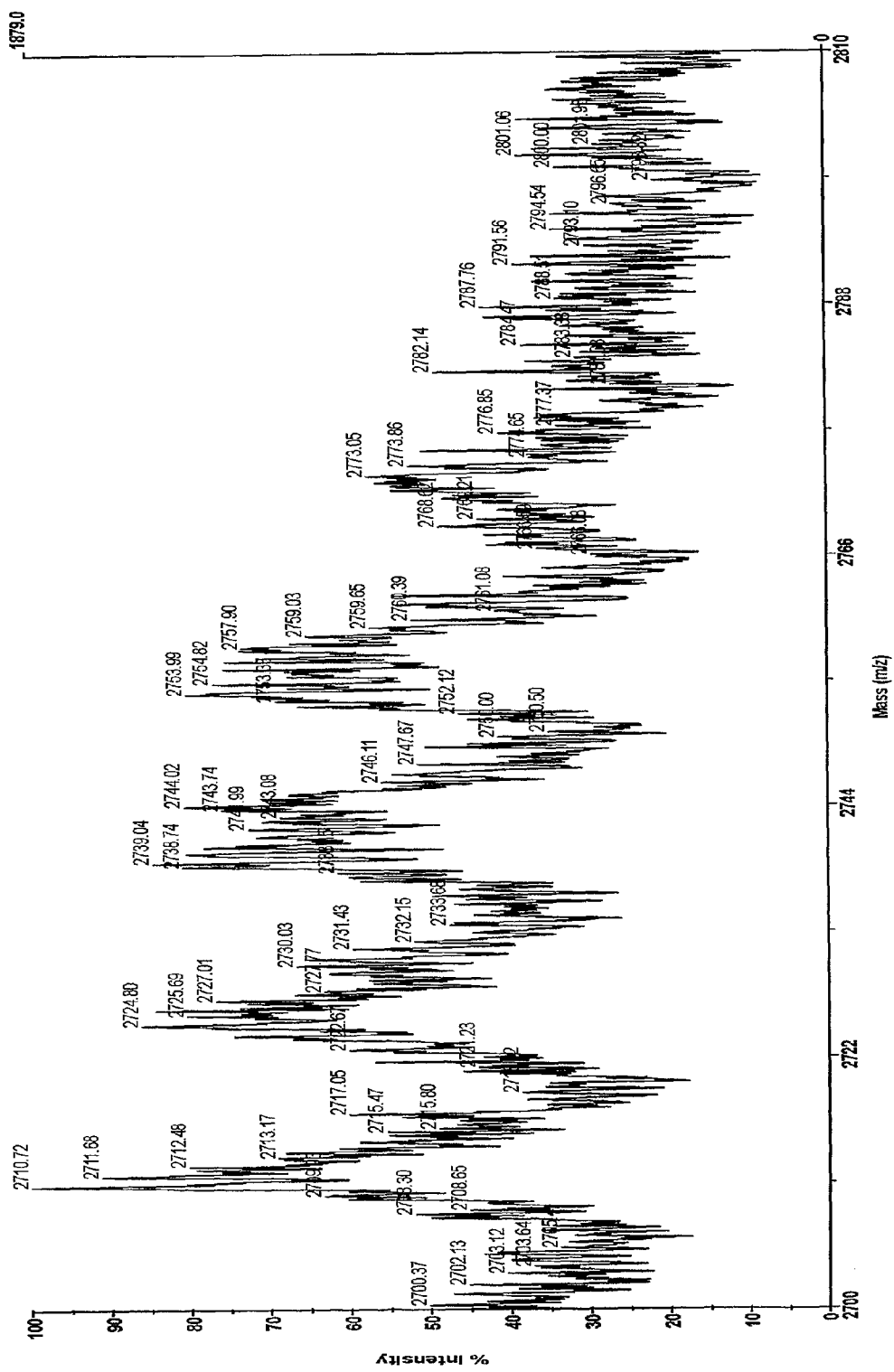
FIG. 45 depicts the MALDI mass spec of V8.

FIG. 45 depicts the MALDI mass spectrum of crude peptide mixture V8.

Figure 46:
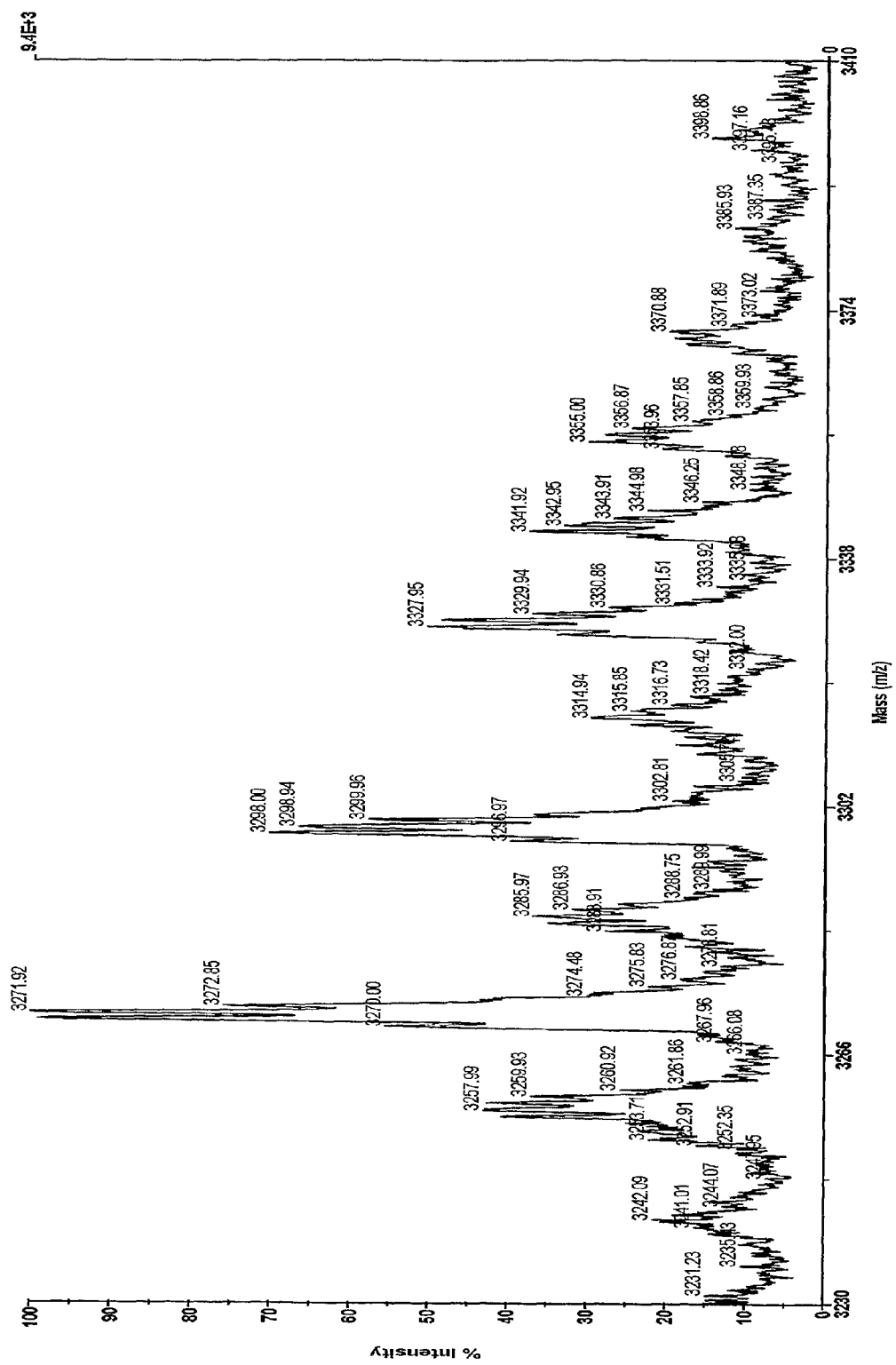
FIG. 46 depicts the MALDI mass spec of V9.

FIG. 46 depicts the MALDI mass spectrum of crude peptide mixture V9.

Figure 47:
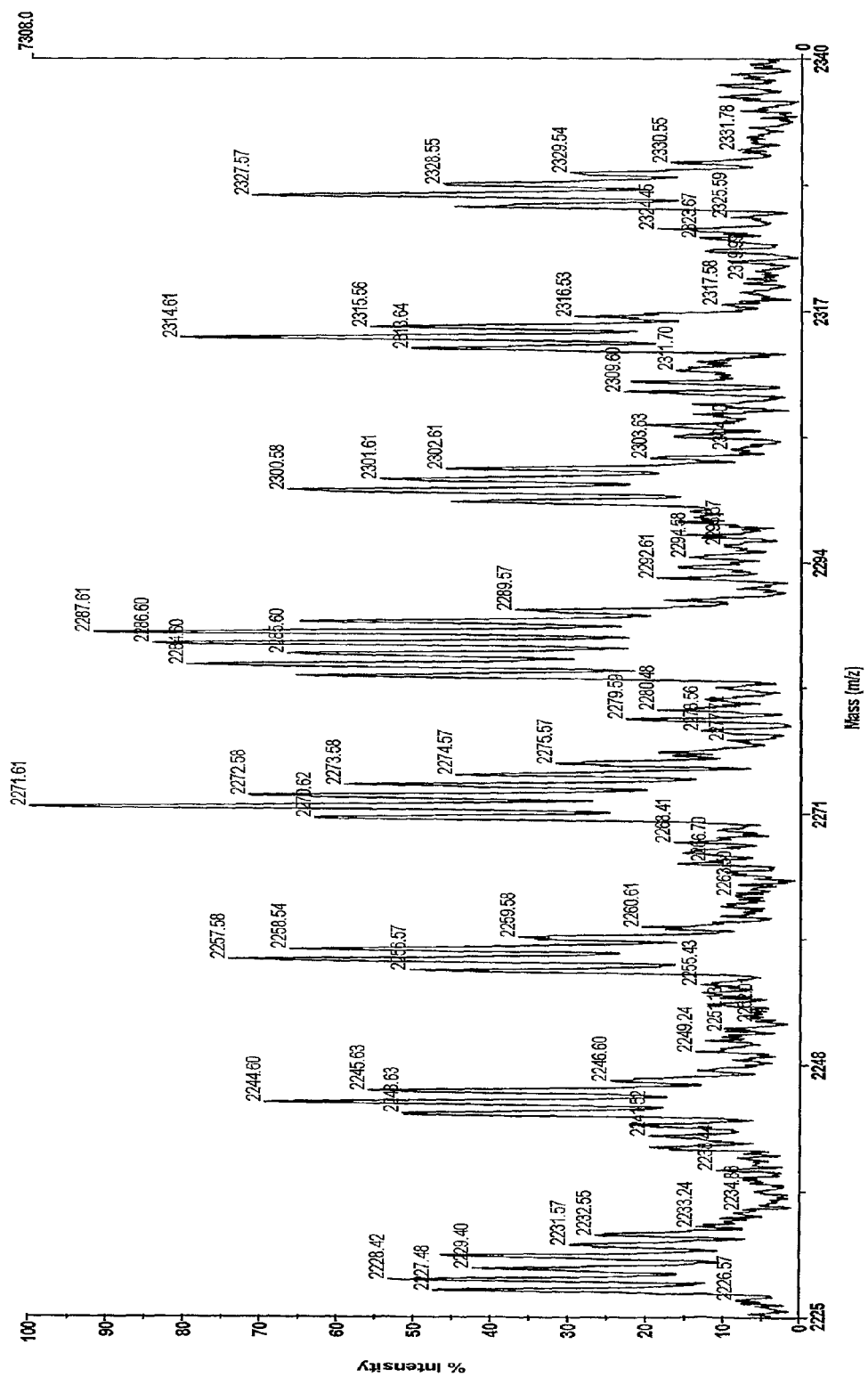
FIG. 47 depicts the MALDI mass spec of V10.

FIG. 47 depicts the MALDI mass spectrum of crude peptide mixture V10.

Figure 48:
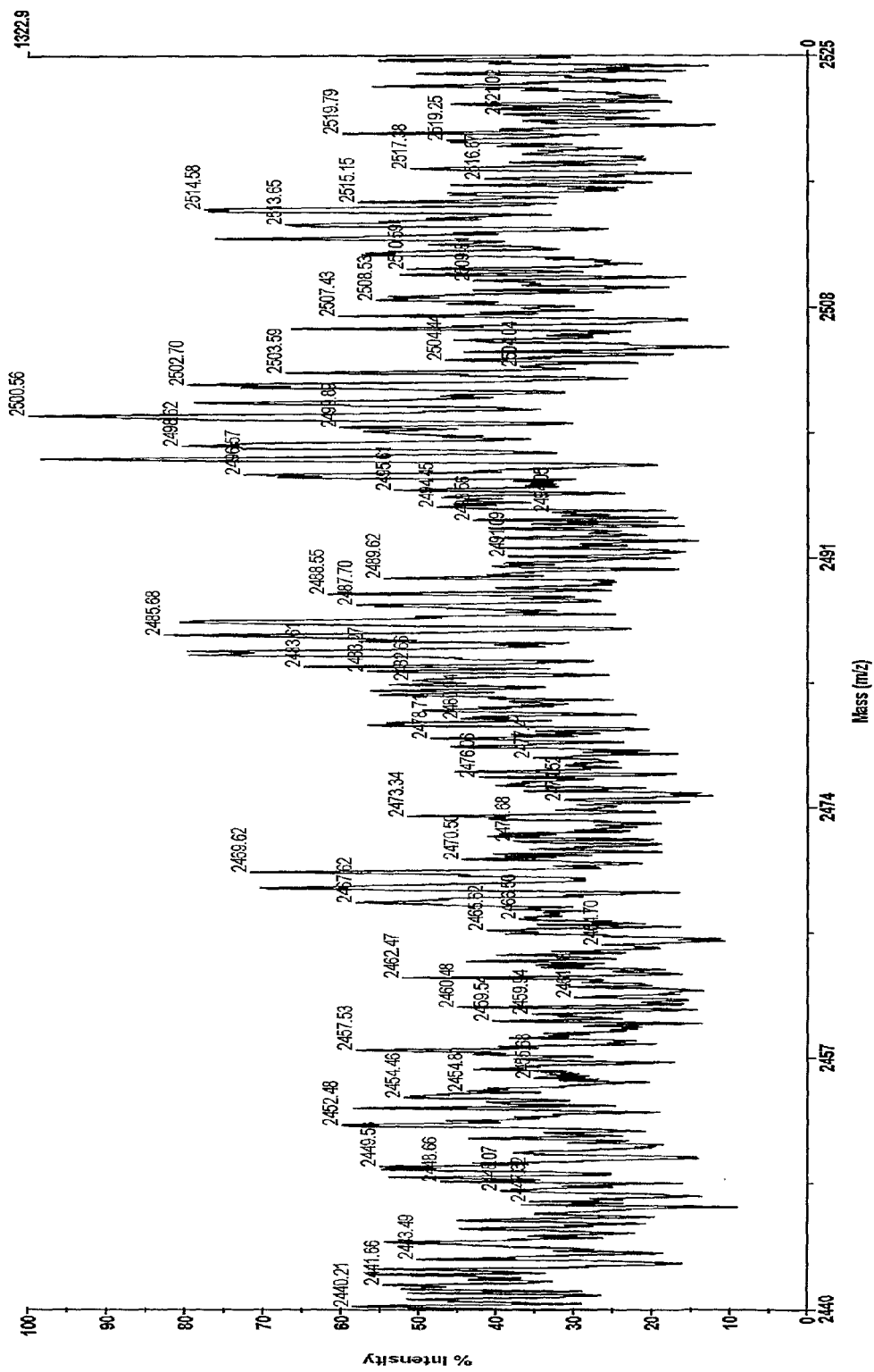
FIG. 48 depicts the MALDI mass spec of V11.

FIG. 48 depicts the MALDI mass spectrum of crude peptide mixture V1.

Figure 49:
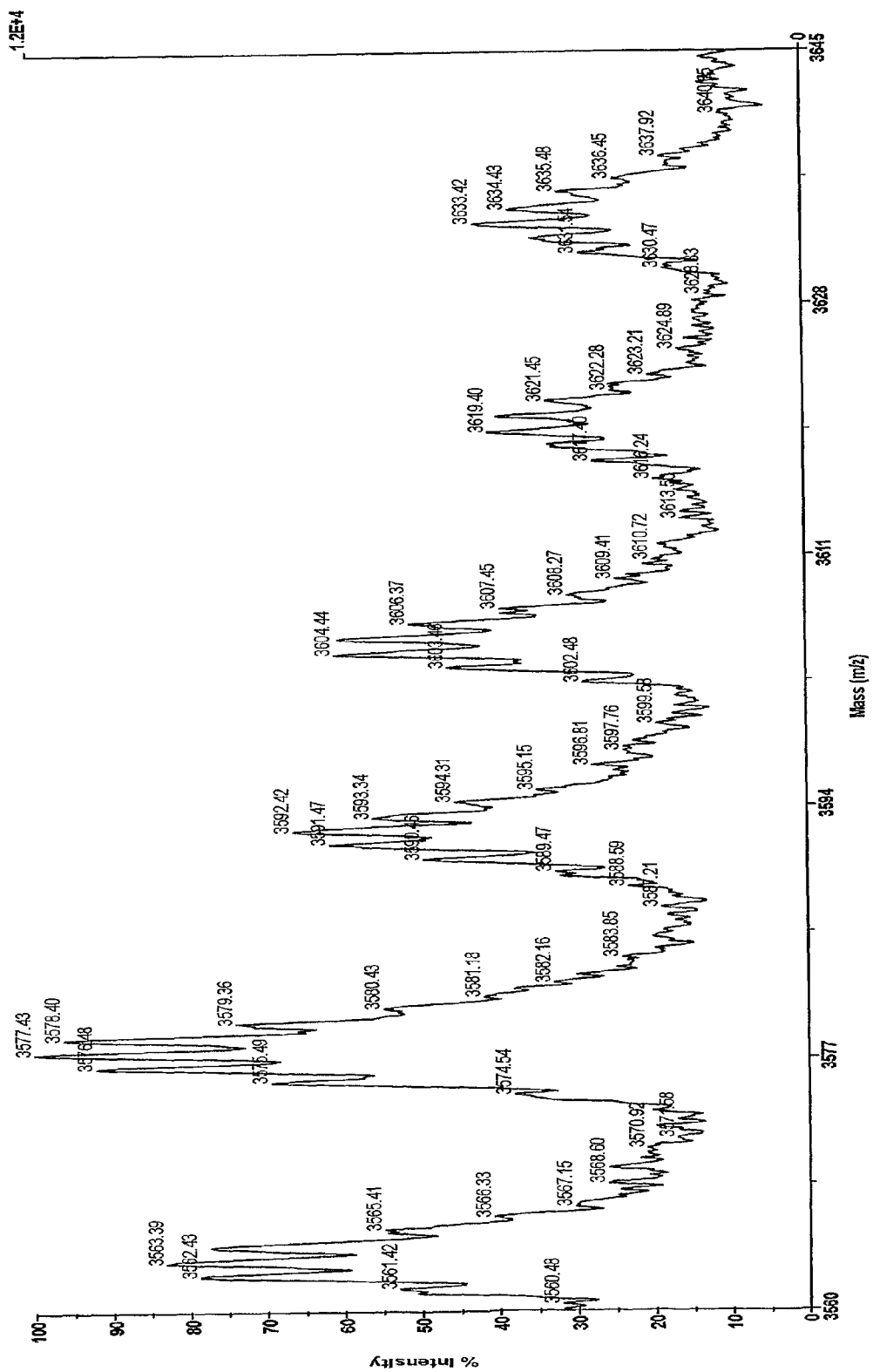
FIG. 49 depicts the MALDI mass spec of V12.

FIG. 49 depicts the MALDI mass spectrum of crude peptide mixture V12.

The final vaccine composition comprises 80 different peptides (SEQ ID NOs: 1 to 80) that represent frequently occurring and predicted sequences present in five hypervariable regions of the HIV-1 gp120, as well lipidated versions of these 80 peptides (SEQ ID NOs: 81 to 160), and 16 additional peptides (SEQ ID NOs: 161 to 176) which may or may not be lipidated and based on two variable regions in the HIV-1 Gag protein (176 peptides in total), in combination with an adjuvant and a buffer.

A group of 6 cynomolgus macaques were immunized simultaneously with 0.1 mg of the final vaccine composition. This procedure was used instead of employ a prime-boost immunization schedule.

Animals received four subcutaneous immunizations. Data indicate that the animals have robust virus-specific CTL responses (measured using an IFN-g ELISPOT assay) against recombinant vaccinia constructs expressing HIV antigens from six HIV clades (A, B, C, D, E, F) as well as four clade B variants. Similarly, T helper cell proliferative responses have been observed against recombinant envelope proteins derived from multiple clades of virus (Clades B, C, and E). IgG Binding antibodies against gp120 were detected at high serum dilutions (>1:10,000). IgA antibodies against gp120 were also detected in saliva at lower titers. Induction of neutralizing antibodies is currently being evaluated. The vaccine elicits balanced, broadly reactive immunity against many HIV clades and variants.

Figure 50:
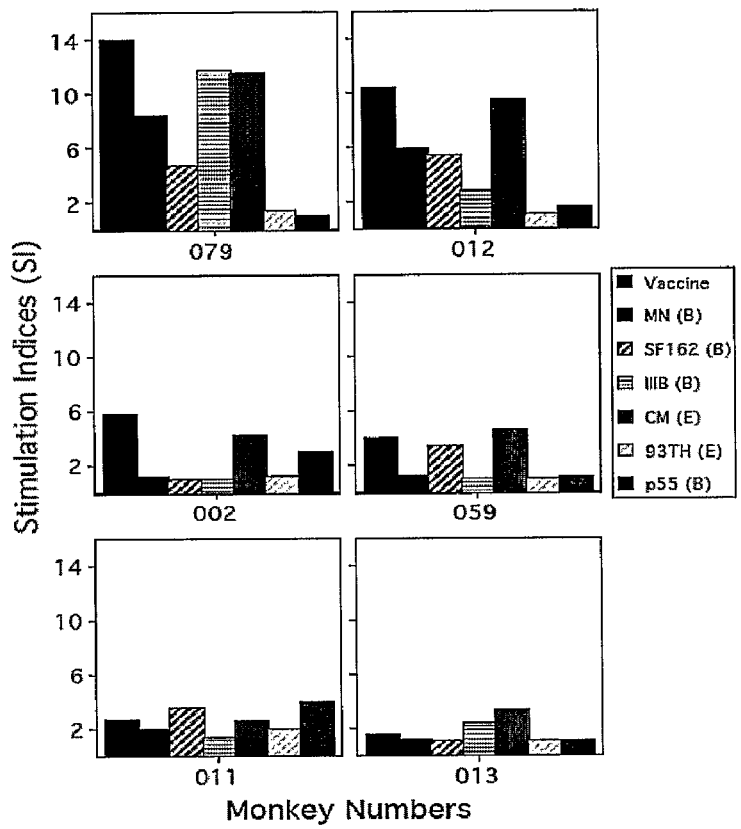
FIG. 50 illustrates stimulation indices (SI) for vaccinated monkeys.

FIG. 50 illustrates the Stimulation Indices (SI) for the six monkeys. Six different monkeys were assessed for stimulation indices of peripheral blood mononuclear cells (PBMC) after exposure to a variety of antigens. The legend illustrates "vaccine" as one of the antigens, in this case meaning non-lipidated peptide compositions V1 to V5 (representing hypervariable regions of envelop proteins). The remaining antigens shown are recombinant proteins representing envelope proteins from which the vaccine of this example is derived. The clade from which the protein is derived is listed parenthetically beside the named protein in the legend. The final antigen of the legend p55 (B) is derived from Gag, while all others shown are from Gp 120. Briefly, stimulation indices are a measurement of proliferation conducted with $^3$H-thymidine added at day 5 post-isolation. Harvesting was done at day 6. These data indicate that the vaccine elicits response in the animals.

Figure 51:
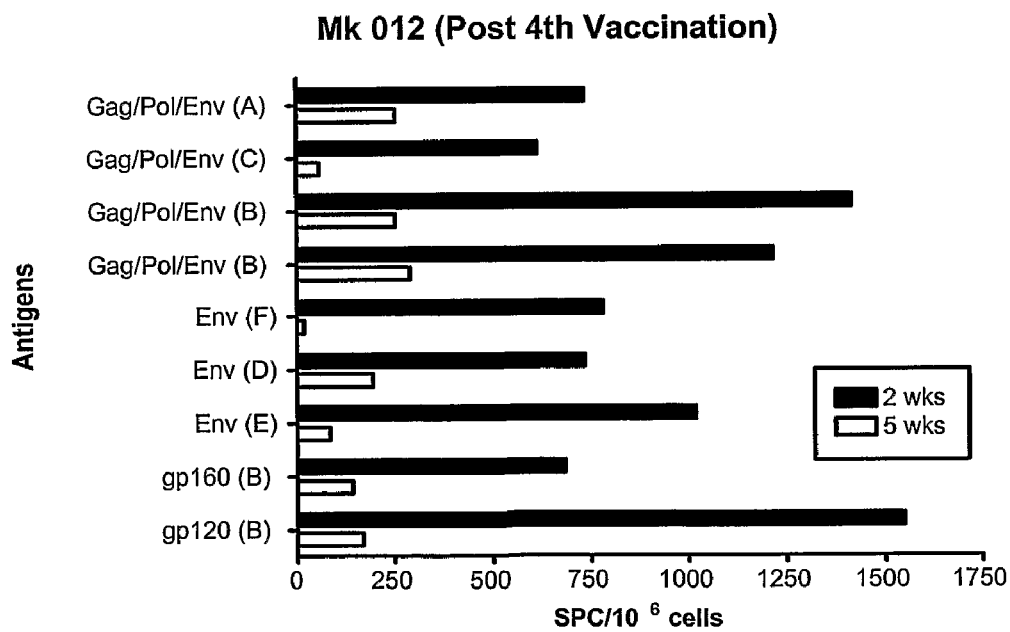
FIG. 51 illustrates a CTL response at 2 and 5 weeks post vaccination.

FIG. 51 shows a CTL response for one of the monkeys at 2 weeks and 5 weeks after delivery of the 4 vaccinations. These data illustrate the induction of CTL response using an EliSpot™ assay, and "SPC" means spot forming cells. Briefly, PBMCs are infected with different vectors expressing viral proteins of interest. The antigens used are shown with the clade from which each is derived listed parenthetically. Data illustrate response at both 2 weeks and 5 weeks post vaccination. Although the response is more pronounced at 2 weeks, the 5 week response shows a lasting effect to be detectable, although decayed from the high 2 week response. Thus, the vaccine is broadly reactive, as shown by the high response to the panel multiple variants used. Notably, representation from clades A to F is provided in the panel of antigens tested, and in each case, reactivity is illustrated. Thus, the vaccine induces a broadly reactive response. It is also illustrated from the lasting response seen even at 5 weeks, that an immunological memory can be achieved, lasting beyond 5 weeks post vaccination.

Figure 52:
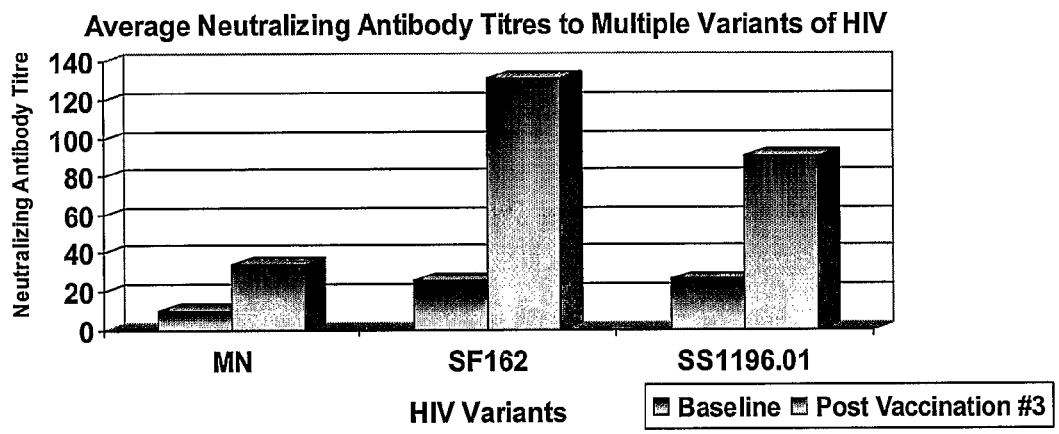
FIG. 52 illustrates the effect of the invention for multiple variants of HIV.

FIG. 52 illustrates the average neutralizing antibody titres to multiple variants of HIV, clade B strains. The first bar shows a baseline titre, while the second bar illustrates the greatly increased response illustrated after the third vaccination. Neutralization was conducted in TZM-b1 cells. Virus stocks used were: HIV-1 MN (H9-grown, 11-01-02); SF162 (PBMC-grown, 03-13-03); SS1196.01 (293T-transfection, 03-04-04).

Figure 53:
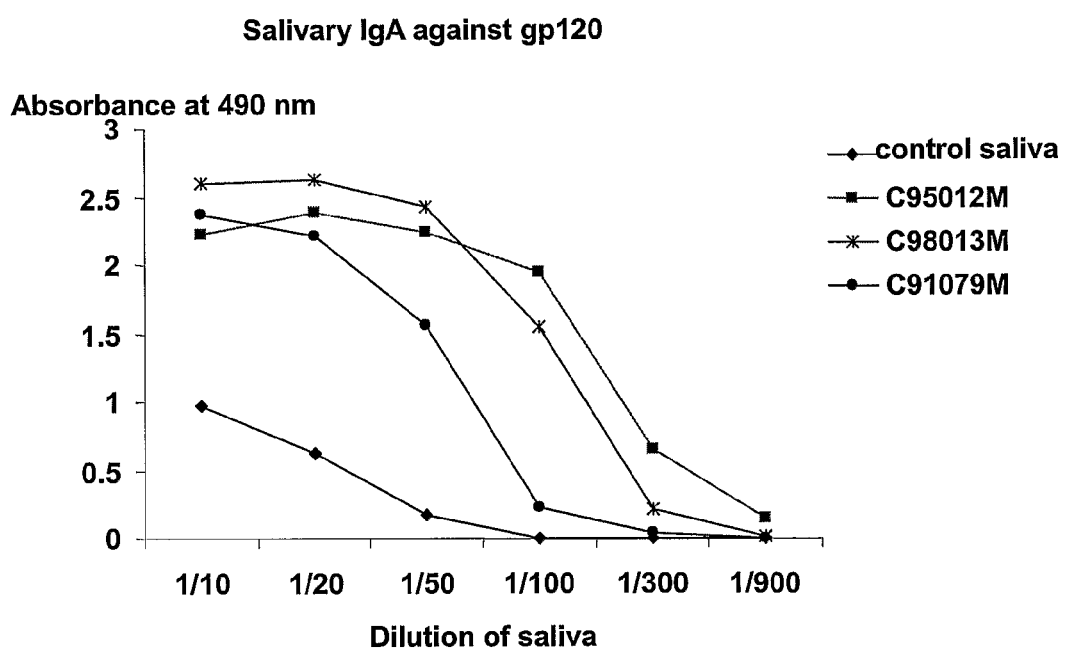
FIG. 53 shows mucosal immunity developed by vaccinated monkeys.

FIG. 53 shows the mucosal immunity developed by monkeys, characterized by anti-HIV-1 IgA, after immunization with the vaccine outlined above. Salivary samples were collected from anesthetized adult cynomolgous monkeys two weeks after the third immunization with the vaccine. Saliva was collected by using sterile 3-ml plastic transfer pipettes. Immediately, EDTA was added to a final concentration of 5 mM to prevent formation of heterotypic calcium ion-dependent immunoglobulin-mucin complexes and to inhibit the IgA1 protease activity in the saliva. The saliva samples were held at −80° C. after filtration through a 0.22 micron Millipore™ filter until assay.

ELISA to detect IgA antibodies in saliva was conducted as follows. Immulo™-2 plates (Dynatech, Chantilly, Va.) were coated overnight with recombinant HIV-1 gp120 at a concentration of 5 µg/ml in 0.05 M carbonate buffer (pH 9.6). Unbound protein was washed from the wells that were then blocked with phosphate-buffered saline (PBS; pH 8.0) containing 0.1% BSA. After the wells were washed, dilutions of saliva samples from each monkey were added in duplicate and incubated overnight with shaking. After the diluted saliva was washed out, a biotinylated affinity-purified polyclonal goat anti-monkey a chain antibody at 2.0 µg/ml was used to detect bound SIgA antibodies. After being washed, streptavidin conjugated with horseradish peroxidase (SA-HRP; Bio-Source International, Camarillo, Calif.) at 0.1 µg/ml was added to the wells to detect the biotinylated antibodies. The wells were washed again, and o-phenylenediamine (1 mg/ml) in citrate-phosphate buffer (pH 4.5) containing 0.012% hydrogen peroxide was added to each well. The optical density at 450 nm was measured with an automated microplate reader (Tecan U.S., Inc., Research Triangle Park, N.C.). As negative control, non-vaccinated monkey saliva was tested as describe previously.

These data show high salivary IgA relative to the control, and serve to illustrate development of mucosal immunity induced by the vaccine.

Figure 54:
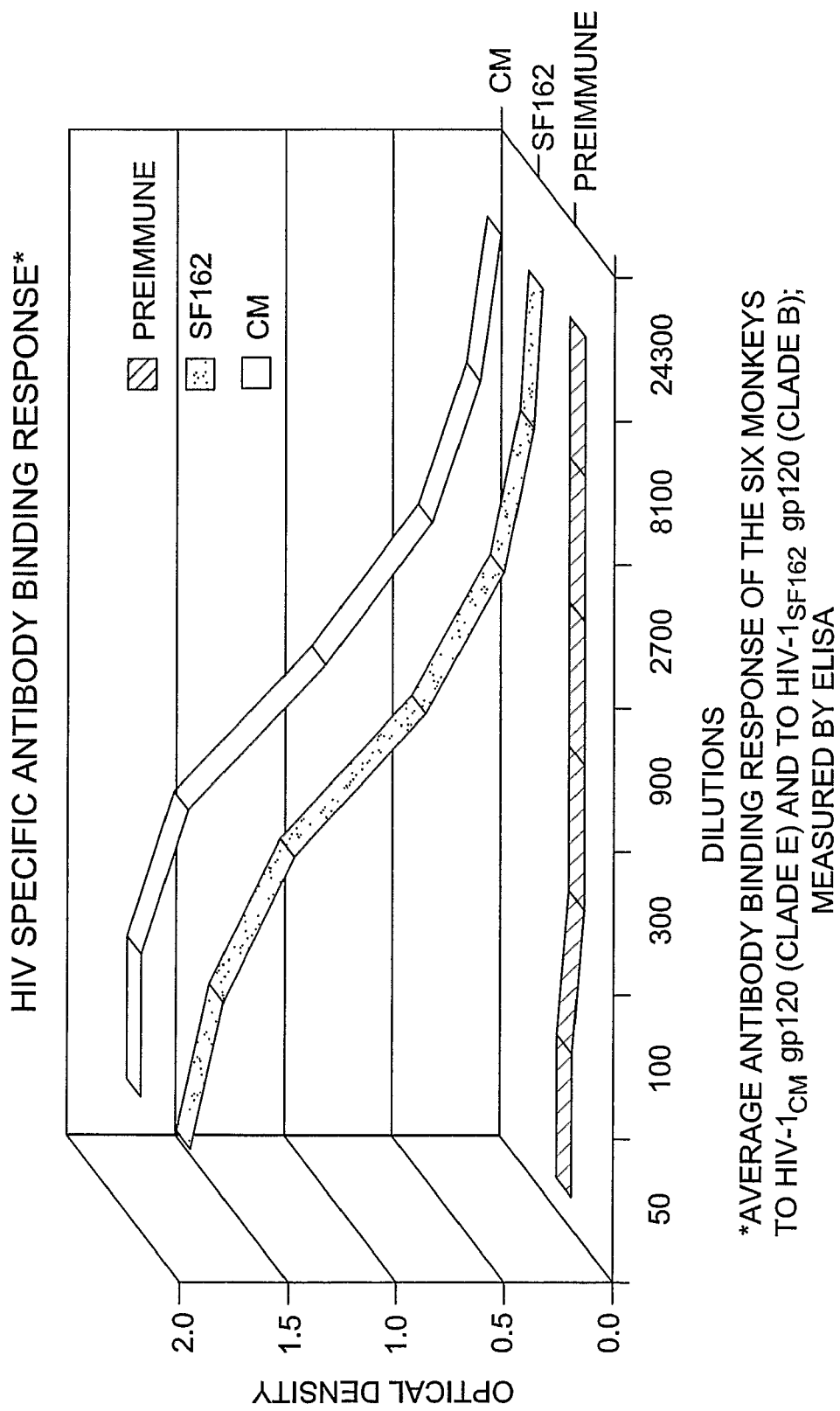
FIG. 54 shows induction of antibody binding response.

FIG. 54 summarizes the HIV specific antibody binding response of the vaccinated monkeys to two divergent strains of HIV. SF162 is a clade B virus (common in North America), and is known among experts to be a difficult strain to elicit antibodies against. CM is a clade E virus, which is common to South-East Asia. ELISA (enzyme linked immunosorbent assay) allows for the determination of the quantity of antibodies in the blood of the monkeys that are specific to Gp120, the envelope protein of HIV. This graph shows the relative concentration of HIV-specific binding antibodies (as measured by optical density) over several dilution points. This graph gives a positive indication that binding antibodies specific to HIV are present after just three immunizations.

Example 2

Vaccine Synthesis, Analysis, and Purification

HIV-1 amino acid sequence data was obtained from the Los Alamos Database and aligned. Twenty-one subtype A, 128 subtype B, 51 subtype C, 17 subtype D, and 33 subtype E sequences were examined in one embodiment of the vaccine formulation of the present invention. Vaccine formulations were based on 5 variable epitopes in the HIV-1 envelope protein and two variable epitopes in the Gag protein (amino acids 131-154, 159-185, 307-324, 388-410, and 456-471 in Env, and amino acids 369-384 and 470-498 in Gag, based on the B.US.SF2 gp120 sequence). During solid phase peptide synthesis using standard Fmoc chemistry, mixtures of two amino acids were added at multiple positions in order to reflect amino acid variability present within an epitope. This mixed addition of amino acid residues produces peptides that are similar to each other, but have defined variability at positions of interest. At completion of each synthesis reaction, either 8 or 16 unique peptide variants of same length were expected to be present.

Seven of the 12 preparations were lipidated in order to promote CTL responses. The lipidated peptides contain two palmitic acid moieties attached to each peptide variant via a Lys containing tripeptide spacer. Lipidated forms of the peptides were synthesized on the solid phase from non-lipidated precursors by the simple elongation of the peptide chains with the tripeptide spacer, Lys-Ser-Ser, followed by one-step double lipidation of Lys at its two free amino groups.

For purification of the non-lipidated peptide mixtures, C18 RP HPLC was used. Lipopeptides were isolated by size-exclusion chromatography on LH-20 Sephadex column in DMSO as a solvent. Solutions of the purified peptide mixtures were afterwards concentrated and then finally lyophilized. All synthesized peptide mixtures were characterized using MALDI-TOF mass spectrometry. The presence of all expected peptide analogs (either 8 or 16) was clearly detected by identifying their unique molecular weights on the corresponding mass spectrum.

Immunization

Six cynomolgus macaques serologically negative for simian immunodeficiency virus (SIV) were obtained from Health Canada. Fifty micrograms of each of the five non-lipidated and seven lipidated formulations were resuspended in sterile saline and mixed at a 1:1 ratio with Montanide ISA-51 adjuvant. The vaccine was injected subcutaneously approximately 2 cm from the inguinal area in the anterior aspect of the thigh, close to the draining inguinal lymph nodes. Animals were vaccinated at months 0, 1, 3, 7, and 10.

Proliferation Assays

Peripheral blood mononuclear cells (PBMCs) were obtained from blood after density gradient centrifugation of Ficoll using standard methodologies. PBMCs ($2\times10^5$/well) were tested in triplicate against the following recombinant proteins: HIV-1 IIIB gp160 and HIV-1 MN gp120 (Advanced Biotechnologies, Inc., Columbia, Md.) and HIV-1 CM gp120 (Protein Sciences Corporation, Meriden, Conn.). The following reagents were obtained through the NIH Research and Reference Reagent Program, Division of AIDS, NIAID, NIH: HIV-$1_{96ZM651}$ gp120, HIV-$1_{93TH975}$ gp120, and HIV-$1_{SF162}$ gp120. Tritiated thymidine (1 µCi/well) was added to all wells at the end of day 5. Cells were harvested on a TOMTEC cell harvester the following day and counts were obtained on a WALLAC 1450 Microbeta Plus liquid scintillation counter. Stimulation indices are defined as the mean cpm value of an experimental condition divided by the mean cpm value obtained in wells incubated without antigen.

Elispot and Flow Cytometric Assays

PBMCs were infected for 90 minutes with 2 pfu of recombinant vaccinia vectors expressing Env or Gag/Pol/Env proteins from six subtypes of HIV-1 (A-F). $2.5\times10^5$ cells were then added to 96 well plates that were coated with anti-monkey IFN-γ antibody (Mabtech, Mariemont, Ohio). After 40 hrs incubation at 37C, cells were removed, washed with PBS+0.05% Tween 20, and incubated with 1 µg/ml of biotinylated anti-monkey IFN-γ antibody (Mabtech) for 2 hrs at room temperature. After washing, 100 µl/well of Streptavidin-ALP-PQ (Mabtech) in PBS+ 0.5% FCS was added and incubated for 1 hr at room temperature. Plates were washed as above and developed with 100 µl per well BCIP/NBT alkaline phosphatase (Moss Inc) for 30 minutes at room temperature. Rinsing the plates with tap water stopped the reaction. Quantitation was determined visually by two independent individuals in a blinded fashion. Responses to empty vector have been subtracted from all reported values. For quantitation of IFN-γ$^+$ and perforin$^+$ T cells, cells were washed and suspended in RPMI-10, then incubated for 16-18 hours in the presence of monensin (BD GolgiStop, BD Biosciences) and surface stained with anti-human CD3-PerCP-Cy 5.5 and CD4-R-PE or CD8-R-PE. Fixation and red blood cell lysis was performed using FACSLYSE buffer according to the manufacturer's instructions (BD Biosciences). PBMC were then permeabilized with Cytoperm (BD Biosciences) and incubated with anti-human perforin-FITC. All fluorochrome-labeled monoclonals were purchased from BD Biosciences. Paraformaldehyde-fixed cells were analyzed on a FACSCAN flow cytometer. Data analysis was performed using WinMIDI software.

Humoral Assays

Plasma collected in EDTA-coated tubes was shipped to Virologic, Inc. for determination of neutralizing activity. Positive neutralizing antibody responses were determined relative to neutralizing activity against a non-HIV-1 virus and to activity present in pre-immunization plasma for each animal. Virus-specific IgA-titers were determined by ELISA. Recombinant proteins (MN, IIIB, CM) or non-lipidated vaccine formulations V1-V5 were adsorbed onto EIA/RIA™ Stripwell plates (Corning Incorporated, USA) at a concentration of 0.3 µg/well. The plates were washed six times with 0.5% Tween-20/PBS, and blocked with 1% BSA (FractionV)/PBS. Serial dilutions (1/10 to 1/8100) of cynomolgus saliva in 1% BSA (FractionV)/PBS were incubated overnight at 4° C. Plates were washed before the addition of a 1/2000 dilution of peroxidase-labeled affinity purified goat antibody to monkey IgA (Kirkegaard & Perry Laboratories, UK). The signal was detected using an o-phenylenediamine (OPD) dihydrochloride (Sigma) substrate and color development was measured at 490 nm on a Biorad plate reader using Microplate Manager software. Endpoint titers were defined as the greatest dilution of a sample with an optical density at least twice that of the mean value of three samples obtained from unimmunized animals.

Challenge Study

HLA-2.1 mice from Jackson Laboratories where immunized 4 times with 12 µg of vaccine ($1/50^{th}$ the dose given to the macaques) or adjuvant alone (PBS and saline) injected subcutaneously at the base of the tail in a total volume of 100 µl (1:1 ratio of ISA-51 adjuvant:PBS). Four weeks after the last immunization, mice were challenged intraperitoneally with $2\times10^7$ pfu of a recombinant vaccinia virus containing expressing Gag/Pol/Env proteins from a subtype E variant of HIV-1. Mice were placed in a biohazard level II facility for 10 days and monitored for sickness and abnormalities over the period of experiment. On day 10, they were euthanized with $CO_2$ gas and the ovaries, the right lung and spleens were dissected and placed in ice-cold PBS. The ovaries and lungs were homogenated separately using a glass Teflon homogenizer, centrifuged, and the supernatant was collected and kept at −80° C. A plaque assay was performed the following day. Serial 10-fold dilutions were prepared in serum free IMDM for each homogenate obtained from the ovaries of each mouse. Homogenate dilutions were used to inoculate previously cultured Hela cells on a 12-well plate and incubated at 37° C. for 3 hours. The media was then removed from the cells were washed once and covered with 2 ml of complete IMDM containing 10% FCS and 0.5% agarose. The plates were left at room temperature for half an hour to let the media solidify and transferred to a 37° C. incubator for 7 days. Plates were fixed over night with 4% paraformaldehyde at room temperature, stained with 0.05% neutral red in PBS for at least 1 hour, rinsed with tap water and left inverted at room temperature to dry prior to counting.

Results

Vaccine Design and Synthesis

Figure 55:
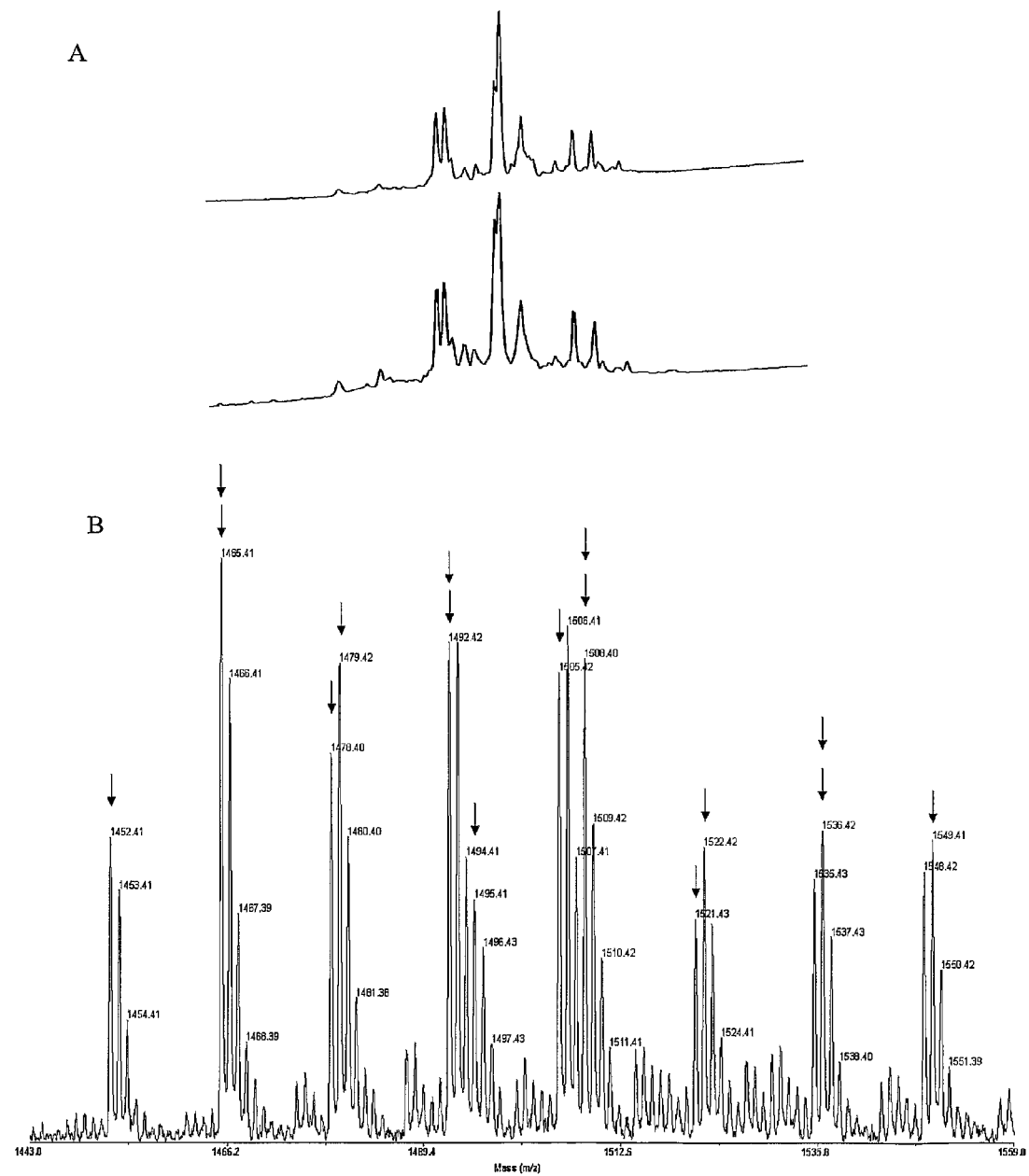
FIG. 55 shows (a) HPLC chromatograms and (b) mass spectra of an exemplary vaccine formulation of the present invention.

As exemplified by HPLC chromatograms, remarkable batch consistency was observed in the manufacturing of the vaccine (FIG. 55A). Moreover, using mass spectrometry the appropriate number of unique peptide species were identified with their anticipated molecular weights (FIG. 55B).

After completion of the synthesis of peptide mixtures, a portion of each of seven mixtures was lipidated using palmitic acid and standard methodology. Two of the peptide mixtures, which represent variable epitopes located in the Gag protein, were lipidated entirely. The lipidated form of the peptide variants served two functions: to elicit CTL responses and to activate innate immunity during vaccination.

Induction of Cross-Subtype Cellular Immunity

Six cynomolgus macaques were immunized 5 times with the vaccine. It was well tolerated by all animals, with minimal redness and swelling of ipsilateral inguinal lymph nodes, and no significant changes in animal behavior, lymphocyte ratios or blood chemistry. There was a no evidence of vaccine-induced autoimmunity.

Figure 56:
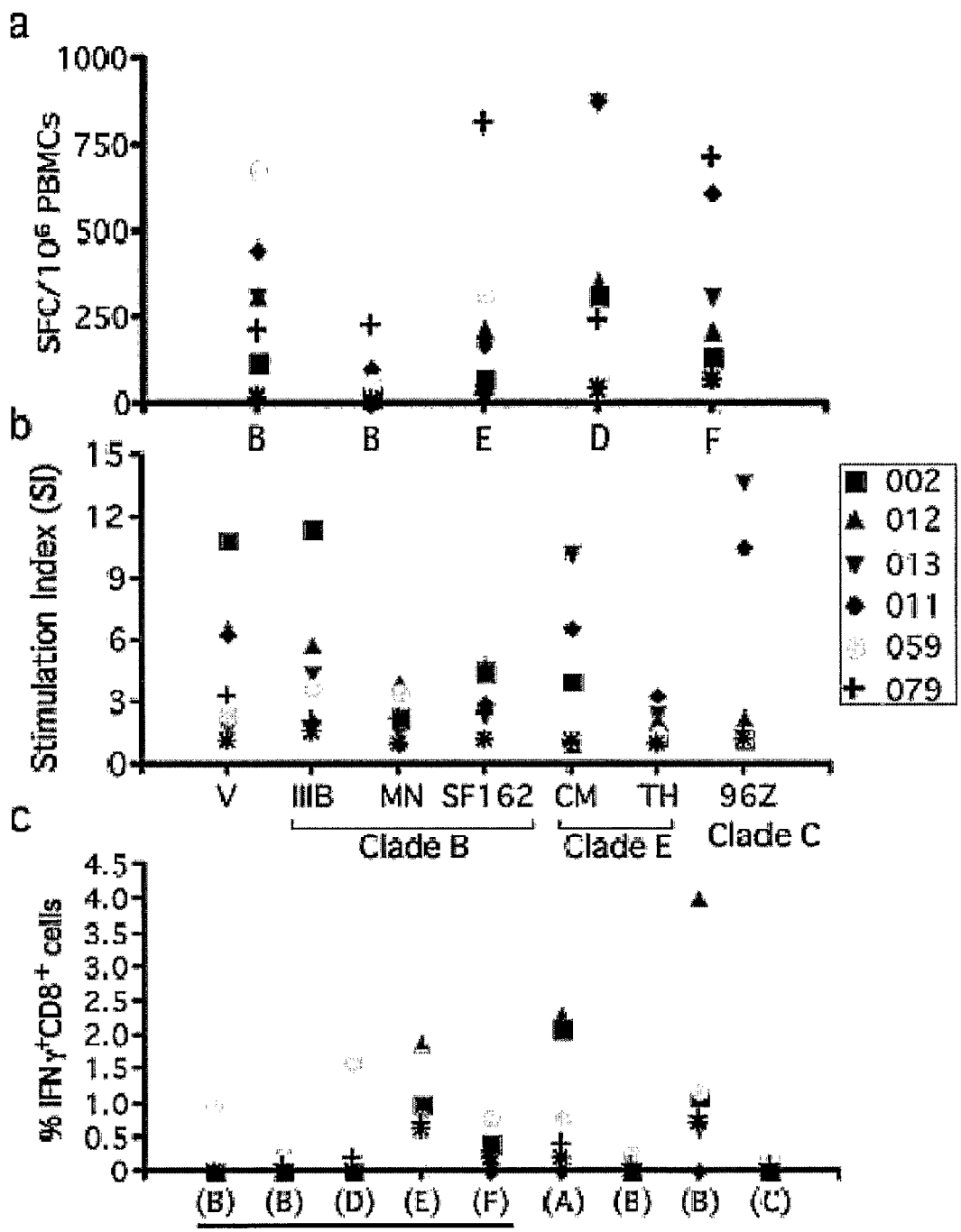
FIG. 56 illustrates induction of reactive cellular immunity of the vaccine of the present invention.

To evaluate the ability of the vaccine to expand a pool of broadly reactive T cells, we used Elispot to measure the frequency of IFN-γ-secreting T cells among PBMCs after brief infection (90 minutes) with recombinant vaccinia vectors expressing envelope proteins from 5 distinct variants of HIV-1, representing subtypes B, D, E, and F. Using this assay we ensured that vaccine-induced T cells were capable of recognizing naturally processed viral antigen. FIG. 56 shows the results of the vaccine to induce cellular immunity. FIG. 56A illustrates the frequency of IFN-γ-secreting T cells responding to a panel of recombinant vaccinia virus vectors expressing Env proteins from multiple subtypes (indicated parenthetically) of HIV-1. Responses to empty vaccinia vector have been subtracted from all values. The average frequency of spot forming cells (SFC) among 4 unimmunized animals to each vector is indicated with an asterisk. FIG. 56B shows T cell proliferative responses measured against the non-lipidated component of the vaccine (V), and against recombinant envelope proteins from 3 distinct subtype B, 2 subtype E, and 1 subtype C HIV-1 viruses. The average stimulation index (SI) of 4 unimmunized animals to each antigen is indicated with an asterisk. FIG. 56C shows the frequency of IFN-γ-secreting CD8$^+$ T cells measured by flow cytometry responding to a panel of recombinant vaccinia virus vectors expressing Env (indicated with bold underline) or Gag/Pol/Env proteins from multiple HIV-1 subtypes (indicated parenthetically). Responses to Env-expressing vectors are indicated with a bold line. The average frequency of IFN-γ-secreting CD8$^+$ T cells from 3 unimmunized animals to each vector is indicated with an asterisk. Animals 079 and 011 responded to every variant tested while animal 012 recognized variants from all of the subtypes of virus tested (FIG. 56A). Animals 059, 013, and 002 responded to a subtype B variant and one additional non-clade B variant.

Given the importance of T helper cells in maintenance of functional CTLs during chronic viral infections, the vaccine of the present invention was designed to elicit a broadly reactive repertoire of T helper cells. To assess the ability of the vaccine to elicit a T helper cell repertoire that could recognize widely divergent strains of HIV-1, proliferative responses to recombinant envelope proteins derived from 3 subtype B variants, 2 clade E variants, and a single clade C variant, were evaluated. Proliferative responses of PBMCs obtained from vaccinated and unimmunized control animals after the third, fourth, and fifth immunizations of the vaccine were evaluated. Proliferative responses after three immunizations in 4/6 animals to multiple subtypes (data not shown) were detected, which increased in strength and breadth over time. When assessed 6 weeks after the fifth immunization, 2 animals (013 and 011) responded to variants from all three subtypes tested while another animal (002) responded to variants from subtypes B and E (FIG. 56B). Two additional animals (012 and 059) responded to multiple subtype B variants. Animal 079 failed to respond to any of the envelope proteins tested at this time point, but did respond to subtypes B and E when assessed at an earlier time point (6 weeks after the third immunization, data not shown).

To formally demonstrate that the vaccine expanded virus-specific CD8$^+$ T cells, PBMCs were similarly infected with recombinant vaccinia vectors expressing Env or Gag/Pol/Env proteins from subtypes A, B, C, D, E, and F. High frequencies of IFN-γ-secreting CD8$^+$ T cells in animals 002, 012, and 059 that recognized three or more subtypes of HIV-1, were detected (FIG. 56C). IFN-γ-secreting CD8$^+$ T cells directed against subtypes B and E were present in animals 013 and 079. Somewhat surprisingly, IFN-γ-secreting CD8$^+$ T cells to any viral variants in animal 011 were not detected, despite the clear ability to detect virus-specific cellular immunity using the other assays.

Figure 57:
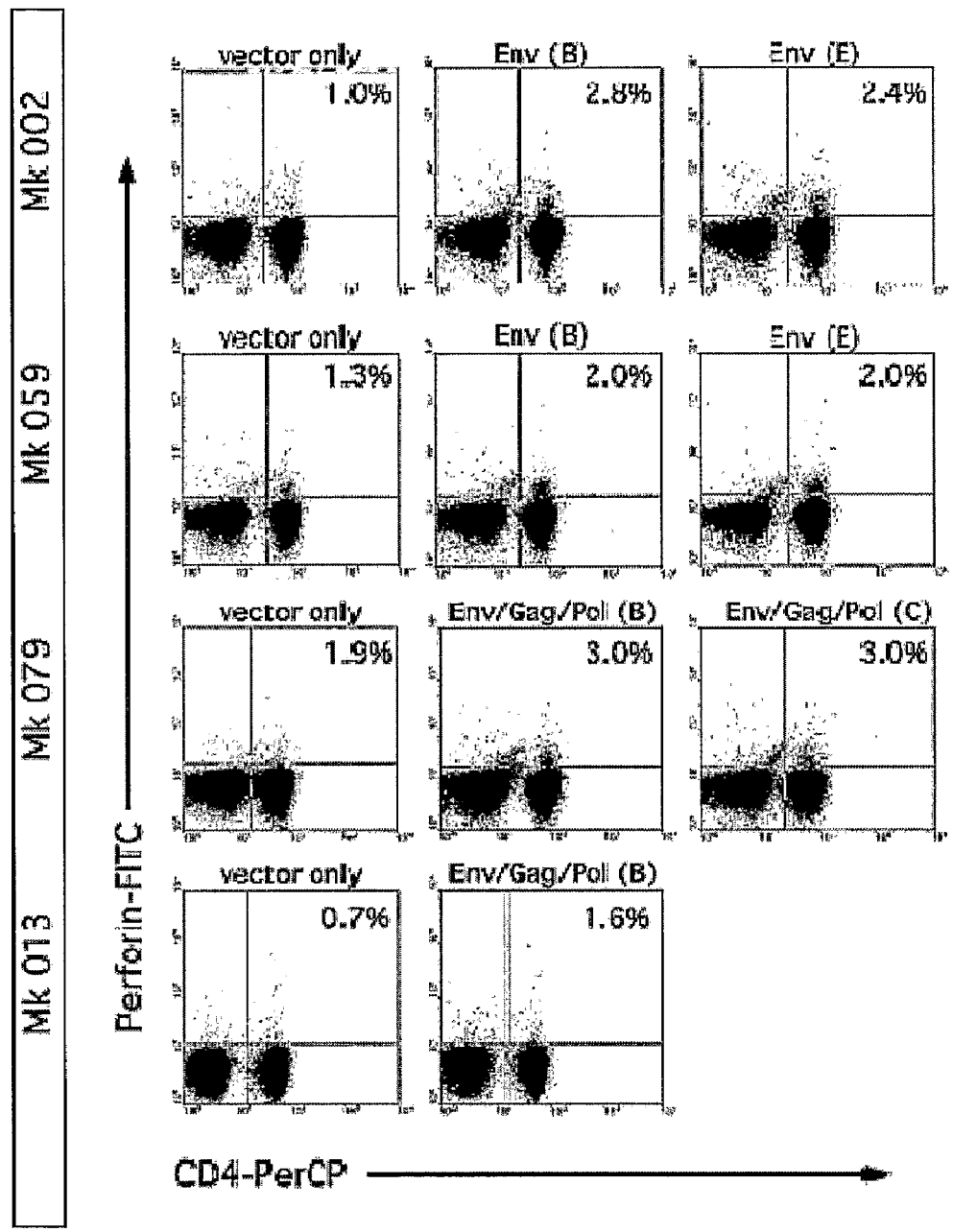
FIG. 57 illustrates the expansion of cytotoxic $CD4^+$ T cells in vaccinated animals.

It has previously been shown that CD4$^+$ T cells with cytotoxic activity are expanded during chronic viral infections (Appay, V., et al. *J Immunol* (2002), 168(11), 5954-5958), and can be induced with vaccination (Cooper, D., et al. *Vaccine* 2004, 23(2), 236-246). Similar to the conditions used for the Elispot assays, PBMCs were briefly infected with recombinant vaccinia vectors to determine the ability to expand virus-specific T helper cells. CD4$^+$perforin$^+$ T cells were quantitated by flow cytometric analysis 16 hours after infection of PBMCs with recombinant vaccinia virus vectors expressing the indicated HIV-1 proteins. The clade of virus to which each variant belongs is indicated parenthetically. The frequency of perforin$^+$ cells among CD4$^+$ T cells is indicated in each panel. After 24 hours, cultures were assessed for the presence of CD4$^+$perforin$^+$ T cells (FIG. 57). When assessed 2 weeks after the fifth immunization, high frequencies of HIV-specific CD4$^+$perforin$^+$ T cells were detected in 4 of the 6 vaccinated animals. These cells were not detected at the later 6 week time point, consistent with the notion that these cells are a terminally differentiated, effector population of T helper cells that are lost over time (Appay, supra).

Induction of Cross-Subtype Humoral Immunity

All vaccinated animals developed antibodies capable of binding to the 5 individual vaccine components that represent the 5 hypervariable regions of the gp120 envelope protein, in addition to a panel of clade B and E HIV-1 envelope proteins (data not shown). To determine if any of these antibodies had functional, biologically relevant neutralizing activity, sera from the vaccinated animals were assessed for their ability to neutralize a panel of primary isolates of HIV-1. Neutralizing antibody activity was evaluated using sera obtained 6 weeks after the 5$^{th}$ vaccination against a total of 24 primary isolates of HIV-1 from 5 clades (A-E), with 13/24 of the isolates T cell tropic and the remainder tropic for macrophages or both macrophages and T cells. Of considerable interest, one of the animals (Mk 013) had antibodies that neutralized 4/13 T cell tropic HIV-1 isolates from both clades D and E; the sera failed to neutralize any of the 11 macrophage or dually tropic isolates (Table 1). More specifically, IC$_{50}$ titers of Mk 013 sera against 3 T cell tropic clade D variants were 1:19, 1:53, and 1:11, with IC$_{50}$ titers of reference HIV-1$^+$ plasma against the same 3 variants of 1:87, 1:67, and 1:35, respectively.

Given that mucosal surfaces are a major portal of entry for HIV infection, mucosal responses present in the vaccinated animals was evaluated. HIV-specific IgA titers in saliva were determined using envelope proteins from two clade B viruses (IIIB and MN) and a clade E variant (CM). Monkeys 012, 059, and 013 had titers ranging from 1:50-1:300 against at least one envelope protein; monkeys 012 and 059 had titers against both clade B and clade E envelope proteins.

TABLE 1

Neutralizing antibodies against T cell tropic strains of HIV-1. Sera from Mk 013 obtained 6 weeks after a 5$^{th}$ vaccination were tested for neutralizing activity against primary isolates of HIV-1 with tropism for T cells (X4), macrophage (R5), or both cell types (dual). Positive antibody activity is denoted with shading.

| | X4 | DUAL | R5 |
|---|---|---|---|
| Clade A | | 92RW009 | 92RW008 |
| Clade B | | 91US054 | 91US723 |
| | | 91US056 | |
| | | 92US005 | |
| | | 92US712 | |
| Clade C | | | 97ZA009 |
| | | | 98IN026 |
| Clade D | 92UG021 | 93UG067 | |
| | 92UG024 | | |
| | 92UG038 | | |
| | 92UG046 | | |
| | 93UG053 | | |
| | 93UG059 | | |
| | 93UG065 | | |
| | 93UG070 | | |
| | 94UG105 | | |
| | 94UG117 | | |
| Clade E | 93TH053 | | 93TH069A |
| | CMU02 | | |
| | CMU08 | | |

Challenge of HLA Transgenic Mice

The exemplified vaccine of the present invention was designed to elicit CTL responses to multiple, antigenically variable regions in both the Env and Gag proteins of HIV-1. However, SHIV viruses that could be used to challenge the presently vaccinated animals express SIV-derived Gag protein, thereby precluding the potential efficacy of vaccine-induced cellular immunity against the epitopes in this protein. Moreover, the utility of SHIV challenge in the species of macaques used in this study is of questionable value given the relatively poor viral replication relative to that in rhesus macaques (Reimann, K. A., et al., *J Virol* (2005), 79(14), 8878-8885).

Figure 58:
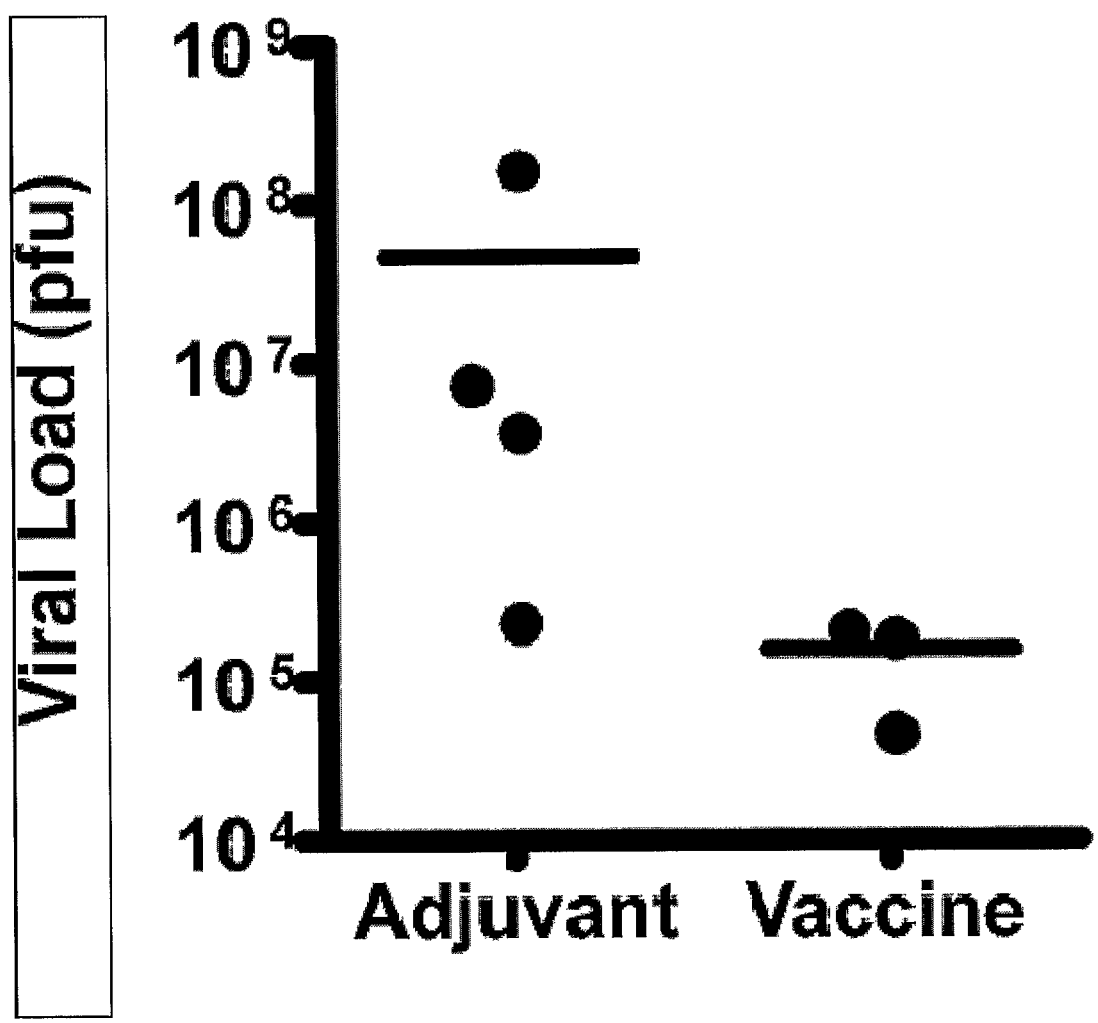
FIG. 58 illustrates the efficacy of a vaccine of the present invention in HLA transgenic mice.

In an effort to evaluate vaccine-induced efficacy, HLA A*0201 transgenic mice were immunized with an exemplary vaccine of the present invention and then challenged them with recombinant vaccinia virus expressing Gag/Pol/Env proteins from a clade E strain of HIV-1. This challenge system allowed the assessment of the impact of both humoral and cellular responses against both the HIV-1 Gag and Env proteins. HLA A*0201 transgenic mice were immunized with the vaccine and challenged 1 month after the final vaccination with a recombinant vaccinia vector expressing HIV-1 viral proteins from a clade E strain of virus. Viral loads were significantly lower 10 days after challenge in vaccinated mice (p<0.05). An approximately 2-log reduction in virus (measured by plaque assay) was observed in the vaccinated mice compared to control (p<0.05) (FIG. 58). The data indicate that vaccine-induced immunity was able to recognize and eliminate processed viral antigens in vivo.

The above-described embodiments of the present invention are intended to be examples only. Alterations, modifications and variations may be effected to the particular embodiments by those of skill in the art without departing from the scope of the invention, which is defined solely by the claims appended hereto. All publications noted herein are incorporated by reference in their entirety.

The invention claimed is:

1. An anti-human immunodeficiency virus (HIV) immunogenic composition comprising isolated peptides:
   SEQ ID NO: 1 to SEQ ID NO: 176, wherein isolated peptides SEQ ID NO: 81 to SEQ ID NO: 160 are lipidated peptides; and
   a pharmaceutically acceptable carrier.

2. The anti-HIV immunogenic composition according to claim 1, wherein isolated peptides SEQ ID NO: 161 to SEQ ID NO: 176 are lipidated peptides.

3. The anti-HIV immunogenic composition according to claim 2, wherein the lipidated peptides comprise a lipidated oligopeptide spacer attached thereto.

4. The anti-HIV immunogenic composition according to claim 3 wherein the spacer comprises 3 or fewer amino acids.

5. The anti-HIV immunogenic composition according to claim 3 wherein the spacer is a tripeptide.

6. The anti-HIV immunogenic composition according to claim 3 wherein the spacer comprises Lys-Ser-Ser.

7. The anti-HIV immunogenic composition according to claim 6 wherein the Lys residue of the spacer is lipidated.

8. The anti-HIV immunogenic composition according to claim 3 wherein the spacer is attached to the N-terminal residue of the isolated peptide.

9. The anti-HIV immunogenic composition according to claim 2, wherein the lipidated peptides are lipidated at the N-terminal or C-terminal amino acid residue.

* * * * *